United States Patent [19]
Kabasawa et al.

[11] Patent Number: 5,478,839
[45] Date of Patent: Dec. 26, 1995

[54] CYCLOHEXANE DERIVATIVES

[75] Inventors: Yasuhiro Kabasawa, Tsukuba; Fumihiro Ozaki, Ushiku; Keiji Ishibashi, Tsukuba; Takashi Hasegawa, Tsukuba; Hitoshi Oinuma, Tsukuba; Manabu Shirato, Tsukaba; Katsuhiro Moriya, Tsukuba; Toshiaki Ogawa, Tokyo; Satoshi Katayama, Tsukuba; Shigeru Souda, Ushiku, all of Japan

[73] Assignee: Eisai Co., Ltd., Tokyo, Japan

[21] Appl. No.: 300,201

[22] Filed: Sep. 2, 1994

[30] Foreign Application Priority Data

Sep. 21, 1993 [JP] Japan .................. 5-234538

[51] Int. Cl.⁶ ............... A61K 31/435; C07D 471/04
[52] U.S. Cl. ................ 514/300; 546/118; 546/121; 560/13
[58] Field of Search ................ 546/121, 118, 546/331; 564/74; 514/300, 303

[56] References Cited

U.S. PATENT DOCUMENTS 5,342,848   8/1994   Hart et al. .................. 546/331

FOREIGN PATENT DOCUMENTS

0609442A1   8/1994   European Pat. Off. .
WO91/10652  7/1991   WIPO .
WO93/08168  4/1993   WIPO .

OTHER PUBLICATIONS

*J. Med. Chem.*, 1993, 36 1604–1612 Brown et al "Syntheses and Biological Activities of Potent Potassium . . . Channel Openers".

*Primary Examiner*—Bernard Dentz
*Attorney, Agent, or Firm*—Nixon & Vanderhye

[57] ABSTRACT

To provide a cyclohexane derivative defined by the formula (I) or a pharmacologically acceptable salt thereof:

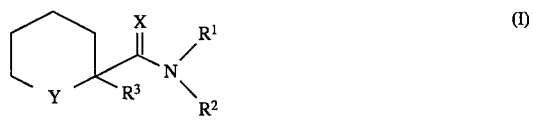

(wherein $R^1$ and $R^2$ may be the same or different from each other and each represents hydrogen or lower alkyl; $R^3$ represents optionally substituted aryl or optionally substituted heteroaryl; X represents oxygen or sulfur; and Y represents a group represented by the formula:

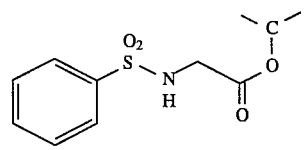

or the like). The compound of the present invention is useful as a preventive and therapeutic agent for diseases against which a potassium channel opening action is efficacious.

9 Claims, No Drawings

CYCLOHEXANE DERIVATIVES

The present invention relates to a cyclohexane derivative useful as drugs. More particularly, it relates to a cyclohexane derivative exhibiting a potassium channel opening activity.

PRIOR ART

Asthma is a considerably long known disease which has paroxysmal dyspnea due to the reversible structure of the respiratory tract and stridor as main signs, but the cause thereof has not been elucidated as yet.

Asthma is generally classified depending upon disease type into atopic asthma, infectious asthma and combined asthma which is infection-exacerbated atopic asthma. However, these types of asthma are little different from each other in the symptoms and pneumo-physiological changes at attack, the therapy of attack or the like, and the frequency of the coexistence of hypersensitivity of the respiratory tract with allergy is too high to be regarded as accident. Therefore, doctors and research workers who participate in the treatment of asthma generally believe that various types of asthma result in one disease.

The methods for treating the above types of asthma is now roughly classified into three groups. One of the groups is so-called hyposensitization therapy, which is now regarded as the best one, but is disadvantageous in that it is generally inefficacious against infectious asthma.

Another of the groups is nonspecific therapy and representative examples thereof include the administration of a gold salt or γ-globulin and vaccination. However, most of these, therapeutic methods are disadvantageous in that the mechanism of action is not known.

The third group is symptomatic therapy, which refers mainly to medication, though it includes various methods. Examples of the drug to be used for this purpose include β-stimulants such as isoproterenol and salbutamol; stabilizers for mast cell membrane such as disodium cromoglicate; xanthine preparations such as theophylline and aminophylline; and steroid preparations. However, the β-stimulants cause side effects such as arrhythmia, hypertension and headache; the xanthine preparations cause side effects such as gastrointestinal diseases and neuropathy; and the steroid preparations cause potent side effects such as diabetes mellitus and osteoporosis. Therefore, care must be taken in the administration of these drugs. Further, the stabilizers for mast cell membrane are disadvantageous in that they can be administered only as an inhalant and therefore are difficult to administer to children and the aged, that they are inefficacious against serious asthma, that they lack in the rapidness of action and hence are usable only preventively, and that the availability is not constant, though they do not give any potent side effect. Accordingly, it can safely be said that the stabilizers leave room for improvement from the standpoint of easiness of use.

SUMMARY OF THE INVENTION

Under these circumstances, it is still expected to develop a preventive and therapeutic agent for asthma which exhibits a new mechanism of action and is improved in safeness and easiness of use.

The inventors of the present invention have made intensive studies for the purpose of developing such an agent. As a result of the studies, they have directed their attention to an ATP-sensitive potassium channel opening activity and then started further studies to find out a compound having such an activity.

As a result of the above studies, they have found that a cyclohexane derivative which will be described below can attain the above object. The present invention has been accomplished on the basis of this finding.

Although no preventive and therapeutic agent for asthma based on potassium channel opening action has been put on the market in Japan, U.S. Pat. No. 4,200,640, discloses a nitro ester of N-hydroxyalkylpyridinamide which has been put on the market as an antianginal agent based on potassium channel opening action. The compounds of the present invention are different from this nitro ester in the structures.

Additionally, compounds having a potassium channel opening activity are disclosed in JP-B 59150/1990, JP-A 63260/1991, 289543/1990, 286659/1990, 21566/1989, 273/1990, 308275/1989, 258760/1990 and so on, but are different from the compounds of the present invention in the structures.

The compound of the present invention is a cyclohexane derivative represented by the following general formula (I) or a pharmacologically acceptable salt thereof:

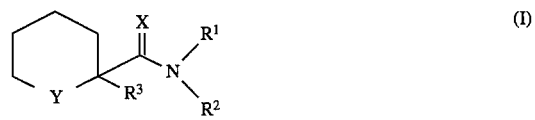

[wherein $R^1$ and $R^2$ may be the same or different from each other and each represents hydrogen or lower alkyl; $R^3$ represents optionally substituted aryl or optionally substituted heteroaryl; X represents oxygen or sulfur; and Y represents a group represented by the following formula (1):

{p is an integer of 0 or 1; and J represents a group represented by the following formula (2):

(wherein $R^4$ represents hydrogen or lower alkyl; $R^5$ represents optionally substituted aryl, optionally substituted arylalkyl, optionally substituted heteroaryl or optionally substituted heteroarylalkyl; $Z^1$ represents a group represented by formula —$SO_2$— or a group represented by formula —CO—; and $W^1$ represents a group represented by the following Formula (3):

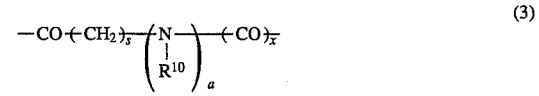

(wherein a and x are independent from each other and each an integer of 0 or 1; s is zero or an integer of 1 to 6; and $R^{10}$ represents hydrogen or lower alkyl), a group represented by the following formula (4):

(wherein $R^{11}$ represents hydrogen, lower alkyl, hydroxyalkyl, optionally substituted arylalkyl or optionally protected carboxyalkyl), or a group represented by the following formula (5):

 (5)

(wherein g is zero or an integer of 1 to 6))}; a group represented by the following formula (6):

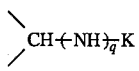 (6)

{wherein q is an integer of 0 or 1; and K represents a group represented by the following formula (7):

$$-W^2-N(R^6)-Z^2-R^7$$ (7)

(wherein $R^6$ represents hydrogen or lower alkyl; $R^7$ represents optionally substituted aryl, optionally substituted arylalkyl, optionally substituted heteroaryl or optionally substituted heteroarylalkyl; $Z^2$ represents a group represented by formula —$SO_2$— or a group represented by formula —CO—; and $W^2$ represents a group represented by the following formula (8):

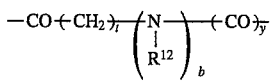 (8)

(wherein b and y are independent from each other and each an integer of 0 or 1; t is zero or an integer of 1 to 6; and $R^{12}$ represents hydrogen or lower alky), a group represented by the following formula (9):

 (9)

(wherein $R^{13}$ represents lower alkyl, hydroxyalkyl, optionally substituted arylalkyl or optionally protected carboxyalkyl), or a group represented by the following formula (10):

 (10)

(wherein h is zero or an integer of 1 to 6))}; or a group represented by the following formula (11):

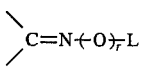 (11)

{wherein L represents a group represented by the following formula (12):

$$-W^3-N(R^8)-Z^3-R^9$$ (12)

(wherein $R^8$ represents hydrogen or lower alkyl; $R^9$ represents optionally substituted aryl, optionally substituted arylalkyl, optionally substituted heteroaryl or optionally substituted heteroarylalkyl; $Z^3$ represents a group represented by formula —$SO_2$— or a group represented by formula —CO—; and $W^3$ represents a group represented by the following formula (13):

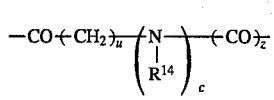 (13)

(wherein c and z are independent from each other and each an integer of 0 or 1; u is zero or an integer of 1 to 6; and $R^{14}$ represents hydrogen or lower alkyl), a group represented by the following formula (14):

 (14)

(wherein $R^{15}$ represents lower alkyl, hydroxyalkyl, optionally substituted arylalkyl or optionally protected carboxyalkyl), or a group represented by the following formula (15):

 (15)

(wherein i is zero or an integer of 1 to 6)); and r is 0 or 1}].

A preferable cyclohexane compound has the formula (I) in which R1 is hydrogen atom, R2 is a C1–C6 alkyl, R3 is imidazopyridyl, X is sulfur, Y is =CH—O—J and J is —COC2—NH—SO2-naphthyl. Another preferable cyclohexane compound has the formula (I) in which R1 is hydrogen atom, R2 is ethyl, R3 is imidazopyridyi, X is sulfur, Y is =CH—O—J and J is —COCH2—NH—SO2-naphthyl. A third preferable compound has the formula (I) in which R1 is hydrogen atom, R2 is ethyl, R3 is imidazopyridyl. X is sulfur, Y is =CH—O—J and J is —COCH2—NH—SO2-naphthyl. The below shown compounds (II) and (III) are more preferable.

The invention provides a pharmacological composition comprising a pharmacologically effective amount of the cyclohexane derivative or a pharmacologically acceptable salt thereof and a pharmacologically acceptable carrier and a method for preventing or treating a disease against which a potassium channel opening action is efficacious by administering a pharmacologically effective amount of the cyclohexane derivative or a pharmacologically acceptable salt thereof to a human subject who will suffer or suffers the disease.

In the above definition, the lower alkyl defined with respect to $R^1$, $R^2$, $R^4$, $R^6$, $R^8$, $R^{10}$, $R^{11}$, $R^{12}$, $R^{13}$, $R^{14}$ and $R^{15}$ is a linear or branched one having 1 to 6 carbon atoms, and examples thereof include methyl, ethyl, n-propyl, isopropyl, butyl, isobutyl, sec-butyl, tert-butyl, pentyl(amyl), isopentyl, neopentyl, tertpentyl, 1-methylbutyl, 2-methylbutyl, 3-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,1,2-trimethylpropyl, 1-ethyl-1-methylpropyl and 1-ethyl-2-methylpropyl, among which methyl, ethyl, n-propyl and isopropyl are preferable.

The hydroxyalkyl defined with respect to $R^{11}$, $R^{13}$ and $R^{15}$ is a lower alkyl as described above in which 1 to 3 hydroxyl groups are each bonded to any of the carbon atoms.

The aryl constituting the optionally substituted aryl defined with respect to $R^3$, $R^5$, $R^7$ and $R^9$ is phenyl, naphthyl, anthracenyl or the like. The substituent constituting it is halogen such as fluorine, chlorine, bromine or iodine; lower alkyl; halogenated lower alkyl such as trifluoromethyl; hydroxyalkyl; nitro; hydroxyl; lower alkoxy; cyano; lower alkylthio; amino; acylamino; alkylamino or the like.

In the above exemplification, the lower alkyl is the same as described above, and the lower alkoxy is one derived from the lower alkyl described above.

Further, the acyl constituting the acylamino given in the above exemplification include those derived from various carboxylic acids and particular examples thereof include those derived from aliphatic saturated monocarboxylic acids, such as formyl, acetyl and propionyl; those derived from aliphatic saturated dicarboxylic acids, such as oxalyl, malonyl, succinyl and glutaryl; those derived from aliphatic unsaturated carboxylic acids, such as acryloyl and propioloyl; those derived from carbocyclic carboxylic acids, such as benzoyl, toluoyl, naphthoyl and cinnamoyl; and those derived from heterocyclic carboxylic acids, such as furoyl, nicotinoyl and thenoyl. The aryl group may have 1 to 5 substituents selected from among those described above.

The heteroaryl constituting the optionally substituted heteroaryl defined with respect to $R^3$, $R^5$ $R^7$ and $R^9$ is a 5- to 7-membered ring or fused ring having 1 to 3 heteroatoms selected from among nitrogen, sulfur and oxygen. Representative examples thereof include thienyl, furyl, pyranyl, pyrrolyl, 2H-pyrrolyl, imidazolyl, isoxazolyl, pyridinyl, indolyl, thianthrenyl, chromenyl, isoquinolyl and phthalazinyl, though the heteroaryl is not limited to them. Further, the substituent constituting it is the same as described with respect to the arylalkyl.

The optionally substituted aryl constituting the optionally substituted arylalkyl defined with respect to $R^5$, $R^{11}$, $R^7$, $R^{13}$, $R^9$ and $R^{15}$ is the same as described above, while the alkyl constituting it is the same as described with respect to the lower alkyl.

The optionally substituted heteroaryl constituting the optionally substituted heteroarylalkyl defined with respect to $R^5$, $R^7$ and $R^9$ is the same as described above, while the alkyl constituting it is the same as described with respect to the lower alkyl. Further, the carboxy-protective group constituting the optionally protected carboxyalkyl defined with respect to $R^{11}$, $R^{13}$ and $R^{15}$ is preferably lower alkyl such as methyl or ethyl, arylalkyl, heteroarylalkyl or the like.

The aryl constituting the arylalkyl is the same as described above, while the alkyl constituting it is the same as described with respect to the lower alkyl. The optionally protected carboxyl group may be bonded to any of the carbon atoms of the alkyl. Representative examples of the arylalkyl include benzyl, tolylmethyl and naphthylethyl, though the arylalkyl is not limited to them. Further, representative examples of the heteroarylalkyl include pyridylmethyl furylethyl and thienylpropyl, though the heteroarylalkyl is not limited to them.

The pharmacologically acceptable salt according to the present invention includes inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as argininate, aspartate and glutamate.

Further, the derivative of the present invention may form a metal salt such as sodium, potassium, calcium or magnesium salt. The pharmacologically acceptable salt of the present invention includes these metal salts.

As appears from the structures, the compounds of the present invention may be present as various optical isomers. Further, they may be present also as various geometrical isomers depending upon the substituent. It is needless to say that the present invention include these isomers.

Among the compounds of the present invention, those represented by the following general formula (I') are preferable:

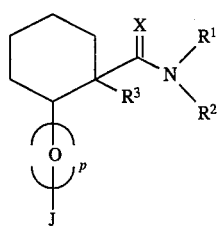
(I')

In the above general, formula (I'), $R^1$, $R^2$, $R^3$, X, J and p are each as defined above. The cases in which $R^1$, $R^2$, $R^3$, X, J and p are as follows are still preferable.

It is desirable that one of $R^1$ and $R^2$ be hydrogen and the other be lower alkyl, more desirably methyl, ethyl or propyl, most desirably methyl.

It is desirable that $R^3$ be optionally substituted heteroaryl, more desirably imidazopyridyl, most desirably imidazo[1,2-a]pyridin-6-yl.

Although J is a group represented by the formula (2):

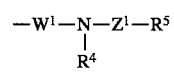
(2)

(wherein $W^1$, $R^4$, $R^5$ and $Z^1$ are each as defined above), it is desirable that $W^1$ be a group represented by the formula (4):

(4)

wherein $R^{11}$ is more desirably hydrogen or lower alkyl, most desirably hydrogen.

It is desirable that $R^4$ be hydrogen.

It is desirable that $R^5$ be optionally substituted aryl or optionally substituted heteroaryl, more desirably aryl, most desirably naphthyl. It is desirable that $Z^1$ be a group represented by formula $-SO_2-$.

Among the compounds represented by the general formula (I), the most desirable optical isomers are those represented by the following general formula (II):

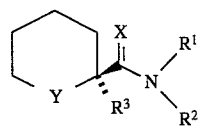
(II)

(wherein $R^1$, $R^2$, $R^3$, X and Y are each as defined above).

Accordingly, the most desirable compounds according to the present invention are those represented by the following general formula (III):

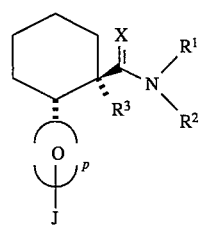
(III)

Main processes for the preparation of the compounds according to the present invention will now be described.

Preparation process 1
A compound represented by the general formula (I) wherein Y is a group represented by the formula (16):

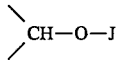
(16)

(wherein J is as defined above) can be prepared by the following process:

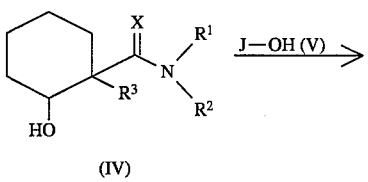
(IV)

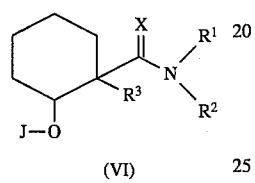
(VI)

According to this process, the objective compound (VI) can be prepared by condensing a compound represented by the general formula (IV) with a compound represented by the general formula (V) or a reactive derivative thereof in the conventional manner.

The reactive derivatives of the compound (V) includes acid halides and symmetric acid anhydrides thereof. When the compound (V) is used in the free form, the condensation is generally conducted in the presence of a condensing agent.

Although any conventional condensing agent can be used in the above reaction, preferable examples thereof include diphenylphosphorylamide, ethyl chloroformate, methanesulfonyl chloride, 1,3-dicyclohexylcarbodiimide, 1,1-carbonyldiimidazole, diethyl azodicarboxylate and dipyridyl disulfide.

According to this process, the reaction can sometimes be advanced by the coexistence of a base. Although any base can be used for this purpose, preferable examples thereof include organic bases such as diisoproloylethylamine, triethylamine; pyridine, picoline, lutidine, N,N-dimethylaniline and 4-dimethylaminopyridine; and inorganic bases such as potassium carbonate and sodium hydroxide.

Preferable examples of the solvent usable in the above reaction include alcohols such as ethanol; ethers such as tetrahydrofuran; hydrocarbons such as toluene; halogenous solvents such as dichloromethane; polar aprotic solvents such as ethyl acetate, N,N-dimethylformamide and acetonitrile; and pyridine.

The reaction temperature may range from about −20° C. to the refluxing temperature of the solvent.

Preparation process 2
A compound represented by the general formula (I) wherein Y is a group represented by the formula (17):

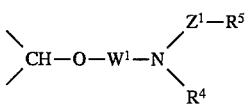
(17)

(wherein $W^1$, $Z^1$, $R^4$ and $R^5$ are each as defined above) can be prepared also by the following process:

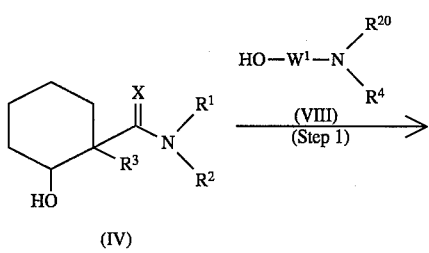
(IV)

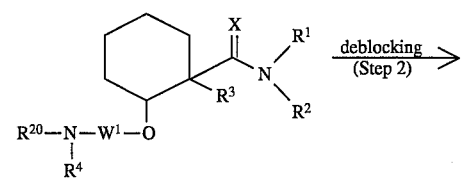
(IX)

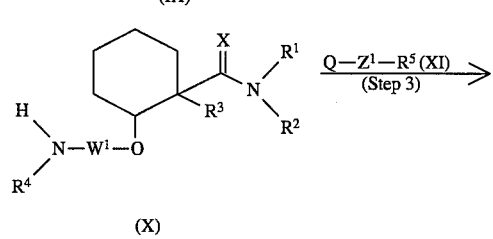
(X)

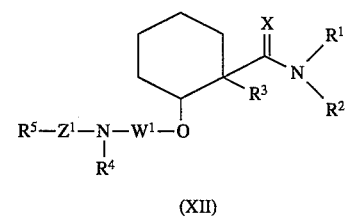
(XII)

(wherein $R^1$, $R^2$, $R^3$, $R^4$, $R^5$, $W^1$, $Z^1$ and X are each as defined above; Q represent a leaving group; and $R^{20}$ represents a protecting group)

(Step 1)
In this step, a compound (IX) is prepared by condensing a compound represented by the general formula (IV) with a compound represented by the general formula (VIII) or a reactive derivative thereof in the conventional manner.

The reactive derivative of the compound (VIII) includes acid halides and symmetric acid anhydrides thereof. When the compound (VIII) is used in the free form, the condensation is generally conducted in the presence of a condensing agent.

The protecting group $R^{20}$ is preferably t-butoxycarbonyl, benzyloxycarbonyl, acetyl, benzoyl, phthaloyl, benzyl, trimethylsilyl or the like, though it may be any conventional protecting group.

Preferable examples of the condensing agent include diphenylphosphorylamide, ethyl chloroformate, methanesulfonyl chloride, 1,3-dicyclohexylcarbodiimide, 1,1-carbonyldiimidazole, diethyl azodicarboxylate and dipyridyl disulfide.

According to this process, the condensation can sometimes be advanced by the coexistence of a base. Although any base can be used for this purpose, preferable examples thereof include organic bases such as diisoprorylethylamine, triethylamine, pyridine, picoline, lutidine, N,N-dimethylaniline and 4-dimethylaminopyridine; and inorganic bases such as potassium carbonate and sodium hydroxide.

Preferable examples of the solvent usable in the above reaction include alcohols such as ethanol; ethers such as tetrahydrofuran; hydrocarbons such as toluene; halogenous solvents such as dichloromethane; polar aprotic solvents such as ethyl acetate, N,N-dimethylformamide and acetonitrile; and pyridine.

The reaction temperature may range from about −20° C. to the refluxing temperature of the solvent.

(Step 2)

In this step, the compound (IX) is converted into a compound represented by the general formula (X) by the conventional deblocking technique.

The process for the deblocking varies depending on the protecting group to be removed. For example, t-butoxycarbonyl can be removed under the acidic condition with hydrochloric, sulfuric or trifluoroacetic acid; benzyloxycarbonyl and benzyl can be removed under the conditions of hydrogenation; and acetyl, benzoyl and phthaloyl can be removed under the acidic condition with hydrochloric, sulfuric or trifluoroacetic acid or under the basic condition with sodium hydroxide, hydrazine or the like.

The protecting group and the deblocking conditions are not limited to their respective examples described above, but may be suitably selected from among known protecting groups and deblocking conditions.

(Step 3)

In this step, the objective compound (XII) is prepared by condensing a compound represented by the general formula (X) with a compound represented by the general formula (XI) or a reactive derivative thereof in the conventional manner.

The reactive derivative of the compound (XI) includes acid halides and symmetric acid anhydrides thereof. When the compound (XI) is used in the free form, the condensation is generally conducted in the presence of a condensing agent.

Preferable examples of the condensing agent include diphenylphosphorylamide, ethyl chloroformate, methanesulfonyl chloride, 1,3-dicyclohexylcarbodiimide, 1,1-carbonyldiimidazole, diethyl azodicarboxylate and dipyridyl disulfide.

According to this process, the condensation can sometimes be advanced by the coexistence of a base. Although any base can be used for this purpose, preferable examples thereof include organic bases such as diisopropylethylamine, triethylamine, pyridine, picoline, lutidine. N,N-dimethylaniline and 4-dimethylaminopyridine; and inorganic bases such as potassium carbonate and sodium hydroxide. Preferable examples of the solvent usable in the above reaction include alcohols such as ethanol; ethers such as tetrahydrofuran; hydrocarbons such as toluene; halogenous solvents such as dichloromethane; polar aprotic solvents such as ethyl acetate, N,N-dimethylformamide and acetonitrile; and pyridine.

The reaction temperature may range from about −20° C. to the refluxing temperature of the solvent.

Preparation process 3

A compound represented by the general formula (I) wherein Y is a group represented by the formula (18):

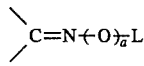
(18)

(wherein L and a are each as defined above) can be prepared also by the following process:

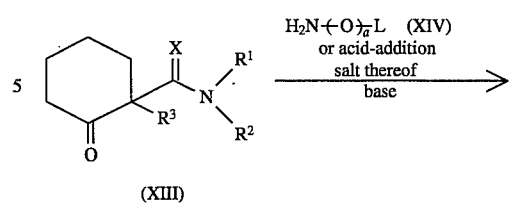

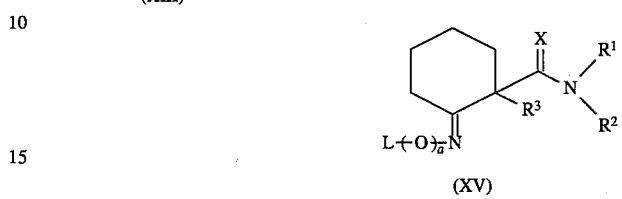

According to this process, the objective compound (XV) is prepared by condensing a compound represented by the general formula (XIII) with a compound represented by the general formula (XIV) or an acid addition salt thereof in the presence of a base.

The base is preferably pyridine or sodium acetate.

The solvent to be used in the above reaction is preferably an alcohol such as methanol, pyridine or water, though any organic solvent inert to the reaction can be used.

The reaction temperature may range from about 0° C. to the refluxing temperature of the solvent.

Preparation process 4

A compound represented by the general formula (I) wherein Y is a group represented by the formula (18):

(18)

(wherein L and a are each as defined above) can be prepared also by the following process:

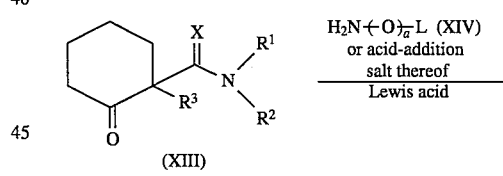

According to this process, the objective compound (XV) is prepared by condensing a compound represented by the general formula (XIII) with a compound represented by the general formula (XIV) or an acid-addition salt thereof in the presence of a Lewis acid.

Preferable examples of the Lewis acid include aluminum chloride and titanium tetrachloride.

The solvent to be used in the condensation is preferably a halogenous one such as dichloromethane, though any organic solvent inert to the reaction can be used.

The reaction temperature may range from about 0° C. to the refluxing temperature of the solvent.

Preparation process 5

A compound represented by the general formula (I)

wherein Y is a group represented by the formula (19):

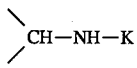
(19)

(wherein K is as defined above) can be prepared also by the following process:

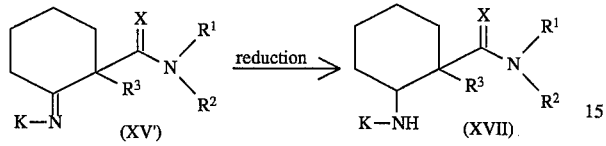

According to this process, the objective compound (XVII) is prepared by reducing the compound (XV') prepared by the Preparation process 3 or 4 in the conventional manner.

The reduction can be conducted by the conventional means, for example, a process using a metal hydride complex or catalytic hydrogenation.

Examples of the metal hydride complex include sodium cyanohydroborate and sodium borohydride. The solvent to be used in the above reaction is preferably an ether such as tetrahydrofuran or an alcohol such as methanol. The reaction temperature may range from about −20° C. to the refluxing temperature of the solvent.

The catalytic hydrogenation is conducted by the use of the conventional catalyst such as palladium-carbon, platinum oxide, Raney nickel or rhodium-alumina. alumina. The solvent to be used in this case is preferably an alcohol such as methanol; a hydrocarbon such as toluene; an ether such as tetrahydrofuan; N,N-dimethylformamide; or ethyl acetate. The reaction temperature may preferably range from 0° C. to the refluxing temperature of the solvent.

Preparation process 6

A compound represented by the general formula (I) wherein Y is a group represented by the formula (20):

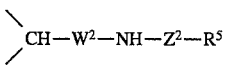
(20)

(wherein $W^2$, $Z^2$ and $R^5$ are each as defined above) can be prepared by the following process:

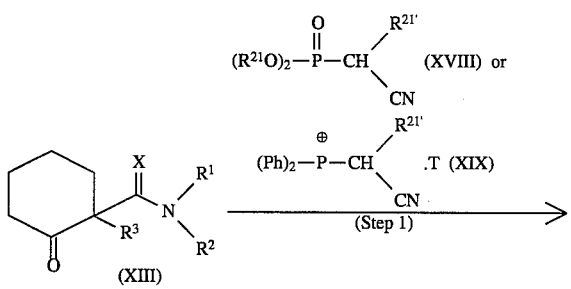

-continued

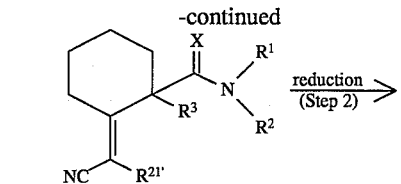

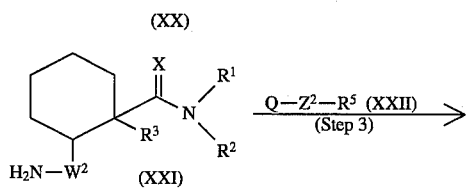

(wherein $R^1$, $R^2$, $R^3$, $R^5$, $Z^2$, $W^2$ and X are each as defined above; T represents a leaving group such as halogen or hydroxyl; $R^{21}$ represents lower alkyl; $R^{21'}$ represents hydrogen, lower alkyl or the like; and S represents halogen).

(Step 1)

In this step, a compound represented by the general formula (XX) is prepared by reacting a compound represented by the general formula (XIII) with a compound represented by the general formula (XVIII) or (XIX) through the conventional Wittig reaction.

Preferable examples of the base include alkali metal hydrides such as sodium hydride; organolithium compounds such as n-butyllithium; and alkali metal alkoxides such as potassium t-butoxide.

The solvent to be used in the above reaction is preferably an ether such as tetrahydrofuran or a polar aprotic solvent such as N,N-dimethylformamide.

The reaction temperature may range from about −78° C. to the refluxing temperature of the solvent.

(Step 2)

In this step, the compound (XX) prepared in the Step 1 is reduced into a compound represented by the general formula (XXI) in the conventional manner.

The reduction can be conducted by the conventional means, for example, one using a metal hydride complex or catalytic hydrogenation.

Examples of the metal hydride complex include sodium cyamohydroborate, sodium borohydride and aluminum lithium hydride. The solvent to be used in the reaction is preferably an ether such as tetrahydrofuran or an alcohol such as methanol, and the reaction temperature may preferably range from about −20° C. to the refluxing temperature of the solvent.

The catalytic hydrogenation is conducted by the use of the conventional catalyst such as palladium-carbon, platinum oxide, Raney nickel or rhodium-alumina. The solvent to be used in this case is preferably an alcohol such as methanol; a hydrocarbon such as toluene; an ether such as tetrahydrofuran; N,N-dimethylformamide; or ethyl acetate.

The reaction temperature may preferably range from 0° C. to the refluxing temperature of the solvent.

(Step 3)

In this step, the objective compound (XXIII) is prepared by condensing the compound (XXI) prepared in the Step 2 with a compound represented by the general formula (XXII) or a reactive derivative thereof in the conventional manner.

The reactive derivative of the compound (XXII) includes acid halides and symmetric acid anhydrides thereof. When the compound (XXII) is used in the free form, the condensation is generally conducted in the presence of a codensing agent.

Preferable examples of the condensing agent include diphenylphosphorylamide, ethyl chloroformate, methanesulfonyl chloride, 1,3-dicyclohexylcarbodiimide, 1,1-carbonyldiimidazole, diethyl azodicarboxylate and dipyridyl disulfide.

According to this process, the condensation can sometimes be advanced by the coexistence of a base. Although any base can be used for this purpose, preferable examples thereof include organic bases such as diisopropylethylamine, triethylamine, pyridine, picoline, lutidine, N,N-dimethylaniline and 4-dimethylaminopyridine; and inorganic bases such as potassium carbonate and sodium hydroxide. Preferable examples of the solvent usable in the above reaction include alcohols such as ethanol; ethers such as tetrahydrofuran; hydrocarbons such as toluene; halogenous solvents such as dichloromethane; polar aprotic solvents such as ethyl acetate, N,N-dimethylformamide and acetonitrile; and pyridine.

The reaction temperature may preferably range from about −20° C. to the refluxing temperature of the solvent.

Preparation process 7

The compound represented by the general formula (I) can be prepared as an optical isomer by the following processes.

For example, a desired optically active compound (I*) can be prepared by optically resolving the starting material or intermediate according to one of the Preparation processes 1 to 6 in the conventional manner and treating a desired optically active starting material or intermediate thus prepared according to the Preparation process.

Alternatively, a desired optical isomer (I*) can be prepared also by directly conducting the optical resolution of the final product (I) in the conventional manner.

The optical resolution can be conducted by any conventional process and examples thereof include a process using an optically active acid such as tartaric acid, dibenzoyltartaric acid, mandelic acid or the like, a process using an auxiliary agent such as a hydrazine derivative; and HPLC using a column for optical resolution.

The compound (IV) used in the above Preparation processes as the starting agent can be prepared according to the process described in W093/08168.

Preparation process A

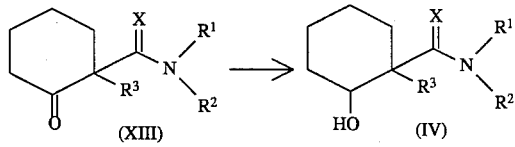

(wherein R¹, R², R³ and X are each as defined above).

According to this process, the compound (IV) can be prepared by reducing a compound represented by the general formula (XIII) with a metal hydride complex or a metal hydride compound.

The metal hydride complex includes sodium borohydride and aluminum lithium hydride, while the metal hydride compound is preferably diisobutyl-aluminum hydride.

Examples of the solvent to be used in the above reaction include alcohols such as methanol; ethers such as tetrahydrofuran; and hydrocarbons such as toluene, though any organic solvent inert to the reaction can be used.

The reaction temperature may range from about −78° C. to about 50° C.

Further, the compound (VI) can be prepared by reducing a compound represented by the general formula (V) with an aluminum alkoxide in an alcoholic solvent. In this case, it is preferable that isopropyl alcohol be used as the solvent and an aluminum alkoxide be used as the reducing agent.

The reaction temperature may range from room one to the refluxing one of the solvent.

A pharmacological experimental example will now be described to illustrate the effect of the present invention.

Pharmacological Experimental Example

Effect of relaxing the smooth muscle of sample trachea extirpated from guinea pig i) Experimental method A Hartley male guinea pig weighing from 300 to 500 g was beaten to death and its neck was cut open to extirpate the trachea therefrom. This trachea was cut open on the side opposite to the bronchial smooth muscle and thereafter cut into round slices between cartilages. Such a slice was used as sample trachea.

This sample was vertically suspended in a Magnus tube (10 ml) filled with the Krebs-Henseleit solution at 37° C. and a gaseous mixture comprising 95% of oxygen and 5% of carbon dioxide was passed through the solution. The change in the contraction was isometrically determined under a load of about 0.5 g. After the sample had been stabilized. 10 mM potassium chloride was added directly to the Magnus tube to cause the sample to contract. After the stabilization of the contraction, a test compound was cumulatively added directly to the Magnus tube to determine the change in the tension.

The ratio (%) of the relaxation caused by the addition of the test compound in each concentration was calculated by taking the contraction caused by the addition of 10 mM potassium chloride as 100% to determine the dose-response curve of the relaxation. The concentration ($EC_{50}$) at which the muscle was relaxed by 50% of the maximum contraction was calculated based on the curve.

ii) Experimental results

The results are given in Table 1, wherein the compounds numbered are as follows:

Compd. 1: 2-(N-benzenesulfonylglycyloxy)-1-(imidazo[1,2-a]pyridin-6-yl)-N'-methylcyclohexanecarbothioamide, Compd. 2: 2-(N-(p-toluenesulfonyl)glycyloxy)-1-(imidazo[1,2-a]pyridin-6-yl)-N'-methylcyclohexanecarbothioamide, Compd. 3: 2-(N-(4-fluorobenzenesulfonyl)glycyloxy)-1-(imidazo[1,2-a]pyridin-6-yl)-N'-methylcyclohexanecarbothioamide, Compd. 4: 2-(N-(4-chlorobenzenesulfonyl)glycyloxy)-1-(imidazo[1,2-a]pyridin-6-yl)-N'-methylcyclohexanecarbothioamide, Compd. 5: 2-(N-(4-bromobenzenesulfonyl)glycyloxy)-1-(imidazo[1,2-a]pyridin-6-yl)-N'-methylcyclohexanecarbothioamide, Compd. 6: 2-(N-(4-trifluoromethylbenzenesulfonyl)-glycyloxy)- 1-(imidazo[1,2-a]pyridin-6-yl)-N'-methylcyclonexanecarbothioamide, Compd. 7: 2-(N-(4-methoxybenzenesulfonyl)glycyloxy)-1-(imidazo[1,2-a]pyridin-6-yl)-N'-methylcyclohexanecarbothioamide, Compd. 8: 2-(N-(2-methoxybenzenesulfonyl)glycyloxy-1-(imidazo[1,2-a]pyridin-6-yl)-N'-methylcyclohexanecarbothioamide, Compd. 9: 2-(N-(2,5-dichlorobenzenesulfonyl)-glycyloxy- 1-(imidazo[1,2-a]pyridin-6-yl)-N'-methylcyclohexanecarbothioamide, Compd. 10: 1-(imidazo[1,2-a]pyridin-6-yl)-N-methyl-2-(2,3,4,5,6-pentafluorobenzenesulfonamido)acetoxy-cyclohexanecarbothioamide, Compd. 11: 2-(N-(2-naphthalenesulfonyl)glycyloxy)-1(imidazo[ 1,2-a]pyridin-6-yl)-N'-methylcyclohexanecarbothioamide, Compd. 12: 2-(N-(8-quinolinesulfonyl)glycyloxy)-1(imidazo[ 1,2-a]pyridin-6-yl)-N'-methylcyclohexanecarbothioamide, Compd. 13: 2-(N-(6-isoquinolinesulfonyl)glycyloxy)-1(imidazo[ 1,2-a]pyridin-6-yl)-N'-methylcyclohexanecarbothioamide, Compd. 14: 2-(N-(2-thiophenesulfonyl)glycyloxy)-1(imidazo[ 1,2-a]pyridin-6-yl)-N'-methylcyclohexanecarbothioamide, Compd. 15: 2-(N-(2-methylpyrazol-3-ylsulfonyl)glycyloxy)- 1-(imidazo[1,2-a]pyridin-6-yl)-N'-methylcyclohexanecarbothioamide, Compd. 16: 2-(N-benzoylglycyloxy)-1-(imidazo[ 1,2-a]pyridin-6-yl)-N'-methylcyclohexanecarbothioamide, Compd. 17: 2-(N-(N'-4-benzenesulfonylglycyl)glycyloxy)- 1-(imidazo[1,2-a]pyridin-6-yl)-N''-methylcyclohexanecarbothioamide, Compd. 18: 2-(2-benzenesulfonamidoethoxy)-1(imidazo[ 1,2-a]pyridin-6-yl)-N'-methylcyclohexanecarbothioamide, Compd. 19: (−)-(1S, 2R)-2-(N-benzenesulfonyl-glycyloxy)- 1-(imidazo[1,2-a]pyridin-6-yl)-N'-methylcyclohexanecarbothioamide, and Compd. 20: (−)-(1S, 2R)-2-(N-(1-naphthalenesulfonyl)-glycyloxy)- 1-(imidazo[1,2-a]pyridin-6-yl)-N'methylcyclohexanecarbothioamide.

TABLE 1

| Test compd. No. | Activity for relaxing extirpated trachea |
|---|---|
| compd. 1 | 7.8 |
| compd. 2 | 7.3 |
| compd. 3 | 7.8 |
| compd. 4 | 7.8 |
| compd. 5 | 7.7 |
| compd. 6 | 6.9 |
| compd. 7 | 7.4 |
| compd. 8 | 7.4 |
| compd. 9 | 7.3 |
| compd. 10 | 6.1 |
| compd. 11 | 7.4 |
| compd. 12 | 7.3 |
| compd. 13 | 7.3 |
| compd. 14 | 7.8 |
| compd. 15 | 7.3 |
| compd. 16 | 7.3 |
| compd. 17 | 6.8 |
| compd. 18 | 7.8 |
| compd. 19 | 8.1 |
| compd. 20 | 7.5 |

It can be understood from the results of the above pharmacological experiment that the compound of the present invention has a potassium channel opening activity. Accordingly, the compound of the present invention is useful as a preventive and therapeutic agent for diseases against which a potassium channel opening action is efficacious. Although specific examples of such diseases include bronchial asthma; hypertension; ischemic heart diseases such as angina pectoris; and cancers, the compound of the present invention is efficacious against any disease, of which a potassium channel opening action is effective in the treatment or prevention.

Further, the compound of the present invention is less toxic and highly safe, thus being valuable also in this sense.

The compound of the present invention can be orally or parenterally administered as a preventive and therapeutic agent for the above diseases. The dose thereof is not particularly limited, but varies depending upon the symptom of a patient, the extent of the symptom; the age, sex and weight of a patient, the sensitivity thereof to drugs; the method, timing and interval of administration; the kind and properties of preparation; the kind of the drug to be administered together therewith; and so on. For example, when it is orally administered, the dose per adult a day is generally about 0.1 to 1000 mg, preferably 0.5 to 500 mg, still preferably 1 to 10 mg, which is administered in one to several portions, preferably one or two portions a day. When it is administered as an injection, the dose is 0.1 to 100 μg/kg. When it is administered as an inhalant, the dose per adult a day is generally about 0.01 to 100 mg, preferably about 0.05 to 50 mg, still preferably 0.1 to 10 mg, which is administered in one to several portions, preferably in one or two portions a day. An inhalant according to the present invention can be prepared by pulverizing the compound of the present invention by the use of a jet mill or the like, adding a surfactant or the like at need, and formulating the obtained mixture into an inhalant in the conventional manner.

The preparations according to the present invention are prepared by the use of the conventional carriers in the conventional manner. More precisely, a solid preparation for oral administration according to the present invention is prepared by adding a filler and, if necessary, a binder, disintegrator, lubricant, color and/or corrigent to an active ingredient, and shaping the obtained mixture into a tablet, coated tablet, granule, powder or capsule.

Examples of the filler include lactose, corn starch, sucrose, glucose, sorbitol, crystalline cellulose and silicon dioxide; those of the binder include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin; those of the lubricant include magnesium stearate, talc, polyethylene glycol, silica and hardened vegetable oil; those of the color include those authorized as pharmaceutical additives; and those of the corrigent include cocoa powder, menthol, aromatic powder, mentha oil, borneol and powdered cinnamon bark. Of course, the tablet and granule may be suitably coated with sugar, gelatin or the like, if necessary. An injection according to the present invention is prepared by adding a pH regulator, buffer, stabilizer and/or solubilizing agent to an active ingredient at need and formulating the mixture into an injection for subcutaneous, intramuscular or intravenous administration by the conventional process.

Examples according to the present invention will now be described to facilitate the understanding of the present invention, though the present invention is not limited to them.

Preparative Example 1

2-(4-Methylimidazol-1-yl)cyclohexanone

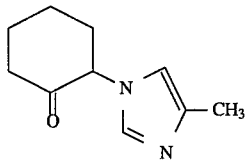

150 g (1.83 mol) of 4-methylimidazole was dissolved in 1.5 l of acetonitrile, followed by the addition of 314 g (2.27 mol) of potassium carbonate. The obtained suspension was heated. When the bulk temperature reached 70° C., a solution of 267 g (2.02 mol) of 2-chlorocyclohexanone in acetonitrile (0.7 l) was dropped into the suspension in one hour. After the completion of the dropping, the obtained mixture was further heated under reflux for 2 hours, followed by the addition of 31.8 g (0.230 mol) of potassium carbonate and a solution of 50.0 g (0.377 mol) of 2-chlorocyclohexanone in acetonitrile (0.1 l). The obtained mixture was heated under reflux for 5 hours.

The reaction mixture was cooled with ice and filtered. The filter cake was washed with acetonitrile. The filtrate and the washings were combined and distilled in a vacuum to remove the solvent. 420 g of a residue was obtained. This residue was purified by column chromatography [3 kg of silica gel, 200:1 to 30:1 dichloromethane/methanol (containing 0.2% of concentrated aqueous ammonia)] to give 143 g of a brown oil. This oil was recrystallized from dichloromethane to give 87.8 g of the title compound as a colorless crystal (yield: 27%).

NMR (400 MHz, δ, CDCl$_3$):

1.76(1H, m), 1.86(1H, m) 2.03–2.13(2H, m), 2.20(1H, m), 2.24(3H, s), 2.39–2.51(2H, m), 2.64(1H, m), 4.67(1H, dd, J=13.0, 5.5 Hz), 6.59(1H, s), 7.34(1H, s)

Preparation Example 2

N-Methyl-1-(4-methylimidazol-1-yl)-2-oxocyclohexanecarbothioamide

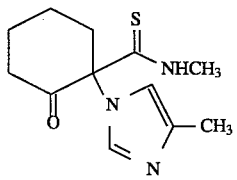

9.88 g (0.247 mol) of sodium hydride (60% oily suspension) was suspended in 1 l of 1,4-dioxane, followed by the addition of 41.4 g (0.232 mol) of the ketone prepared in the Preparative Example 1. The obtained mixture was heated under reflux for 2 hour and the yellow suspension thus obtained was cooled with ice. When the bulk temperature reached 20° C., a solution of 17.0 ml (0.249 mol) of methyl isothiocyanate in 1,4-dioxane (70 ml) was added to the suspension, followed by the addition of 150 ml of N,N-dimethylformamide. The obtained mixture was stirred at 50° C. for one hour. The obtained brown suspension was cooled with ice, followed by the addition of 200 ml of 2N hydrochloric acid. The resulting mixture was neutralized with a saturated aqueous solution of sodium hydrogencarbonate and extracted with dichloromethane (1×2 l, 2×1 l). The combined organic phases were washed with an aqueous solution of common salt, dried over anhydrous sodium sulfate and concentrated in a vacuum. In the course of the concentration, a crystal was precipitated. This crystal was recovered by filtration. 39.2 g of the title compound was obtained as a light-brown crystal (yield: 67%).

NMR (400 MHz, δ, CDCl$_3$):

1.76(1H, m), 1.88(1H, m), 1.94–2.06(2H, m), 2.22(3H, s), 2.48–2.58(2H, m), 2.78(1H, m), 3.14(3H, d, J=4.5 Hz), 3.22(1H, m), 6.64(1H, s), 7.42(1H, s), 8.04(1H, bs)

Preparative Example 3

2-(Imidazo[1,2-a]pyridin-6-yl)cyclohexanone

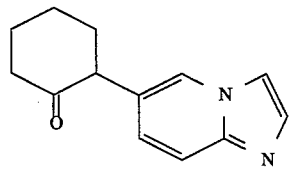

8.98 g of magnesium was added to 300 ml of tetrahydrofuran, followed by the addition of a small portion of a solution of 22.07 g of 6-bromoimidazo-[1,2-a]pyridine and 21.2 ml of 1,2-dibromoethane in 200 ml of tetrahydrofuran. The obtained mixture was heated. A little while later, a reaction was initiated. The residue of the above solution was dropped into the mixture in such a way that the mixture was kept under mild reflux. After the completion of the dropping, the resulting mixture was stirred for one hour, followed by the dropwise addition of a solution of 15.8 g of 2-methoxycyclohexanone in 20 ml of tetrahydrofuran. The obtained mixture was stirred at room temperature for 2.5 hours, followed by the addition of a saturated aqueous solution of ammonium chloride. Hydrochloric acid and ethyl acetate were added to the resulting mixture. The formed aqueous phase was recovered, alkalinized with concentrated aqueous ammonia, and extracted with dichloromethane. The organic phase was dried over anhydrous magnesium sulfate and freed from the solvent by distillation to give 24.05 g of a brown oil. 19.0 g of this oil was dissolved in 40 ml of dichloromethane and the obtained solution was dropped into 60 ml of concentrated sulfuric acid under cooling with ice. The resulting mixture was stirred for 1.5 hours and poured onto ice. The resulting mixture was alkalinized with concentrated aqueous ammonia and extracted with chloroform. The organic phase was dried over anhydrous magnesium sulfate and freed from the solvent by distillation. The residue was purified by silica gel column chromatography (solvent: 40:1 to 20:1 dichloromethane/methanol) to give an oil. This oil was crystallized from ether to give 7.44 g of the title compound as a cream powder (yield: 39%).

m.p. (°C.): 120–121.5

NMR (400 MHz, δ, CDCl$_3$):

1.76–2.12(4H, m), 2.16–2.28(1H, m), 2.29–2.38(1H, m), 2.44–2.62(2H, m), 3.59(1H, dd, J=5.5, 12.4 Hz), 6.95(1H, dd, J=1.6, 9.3 Hz), 7.52(1H, dd, J=0.5, 1.3 Hz), 7.57(1H, d, J=9.3 Hz), 7.60(1H, d, J=1.3 Hz), 7.94(1H, dd, J=0.5, 1.3 Hz)

Preparative Example 4

2-Hydroxy-1-(4-methylimidazol-1-yl)-N-methylcyclohexanecarbothioamide (L-from)

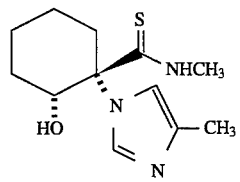

19.09 g of the N-methyl-1-(4-methylimidazol-1-yl) 2-oxocyclohexanecarbothioamide prepared in the Preparative Example 2 was suspended in 290 ml of methanol. The obtained suspension was stirred under cooling with ice, followed by the addition of 1.44 g of sodium borohydride. The reaction mixture was analyzed by silica gel thin-layer chromatography (developer: a 10:1 mixture of chloroform and methanol). The product was a mixture comprising a lower-polarity diastereomer (L-form) as the main product and a higher-polarity one (M-form). After 30 minutes, the reaction mixture was concentrated to about 70 ml, followed by the addition of about 200 ml of water. The precipitate formed was recovered by filtration and washed with water to give 11.85 g of the title compound as a white solid (yield: 62%).

m.p. (°C.): 193–193

NMR (400 MHz, δ, CDCl₃):

1.28(1H, m), 1.46–1.84(5H, m), 1.92(1H, m), 2.24(1H, d, J=0.9 Hz), 2.28(1H, m), 2.58(1H, m), 3.08(3H, d, J=4.8 Hz), 3.47(1H, br), 4.95(1H, dd, J=3.7, 11.2 Hz), 7.11(1H, d, J=0.9 Hz), 7.26(1H, br), 7.98(1H, s)

Preparative Example 5

2-Hydroxy-N-methyl-1-methylimidazo[1,2-a]pyridin-6-yl)cyclohexanecarbothioamide (L-form)

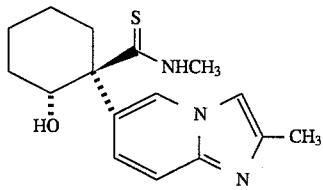

3.03 g of 1-(2-methylimidazo[1,2-a]pyridin- 6-yl)-N-methyl-2-oxocyelohexanecarbothioamide was suspended in 30 ml of methanol. The obtained suspension was cooled with ice, followed by the addition of 0.15 g of sodium borohydride. The obtained mixture was stirred for one hour, followed by the addition of 50 ml of water. The insoluble matter was recovered by filtration and recrystallized from ethanol and then from acetonitrile to give 1.24 g of the title compound (white powder) as a single diastereomer (yield: 41%).

m.p. (°C.): 238–243 (dec.)

NMR (400 MHz, δ, DMSO):

1.28–1.39(2H, m), 1.53–1.70(2H, m), 1.96(1H, m), 2.19(1H, m), 2.30(3H, d, J=0.7 Hz), 2.49(1H, m), 2.91(3H, d, J=4.2 Hz), 3.32(1H, m), 4.61(1H, br), 4.90(1H, br), 7.26(1H, dd, J=dd, J=1.6, 9.5 Hz), 7.30(1H, d, J=9.5 Hz), 7.66(1H, s), 8.52(1H, s), 9.22(1H, br)

Preparative Example 6

N-Ethyl-2-hydroxy-1-(imidazo[1,2a]pyridin-6-yl)-cyclohexanecarbothioamide (an about 5:1 mixture of L- and M-diastereomers)

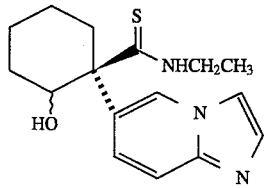

5.0 g of N-ethyl-1-(imidazo[1,2-a]-pyridin- 6-yl)-2-oxo-cyclohexanecarbothioamide was suspended in 55 ml of methanol. The obtained suspension was cooled with ice, followed by the addition of 0.25 g of sodium borohydride. The obtained mixture was stirred for 30 minutes, followed by the addition of about 100 ml of water. The crystal thus precipitated was recovered by filtration and analyzed by silica gel thin-layer chromatography. The crystal was a mixture comprising a lower-polarity diastereomer (L-form) as the main product and a higher-polarity one (M-form).

The crystal was recrystallized from ethanol to give 2.83 g of the title compound as a white powder (yield: 56%).

This white powder comprised L- and M-diastereomers at a ratio of about 5:1, but was used in the subsequent step without any additional purification.

NMR (400 MHz, δ, DMSO-d₆):

1.02, 1.19(total 3H, t, J=7.1 Hz), 1.26–1.49(2H, m), 1.52–1.70(2H, m), 1.82, 2.00(total 1H, m), 2.21, 2.74(total 1H, m), 2.49, 3.75(total 1H, m), 3.42–3.55(1H, m), 3.55–3.70(1H, m), 4.28, 4.65(total 1H, m), 4.89, 6.14(total 1H, br), 7.34, 7.37(total 1H, dd, J=1.8, 9.7 Hz), 7.43, 7.47(total, d, J=9.7 Hz), 7.51, 7.52(total 1H, d, J=1.3 Hz), 7.93, 7.95(total 1H, s), 8.45, 8.59(total 1H, m), 9.34, 10.4(total 1H, br)

Preparative Example 7

2-Hydroxy-N-methyl-1-(2-trifluoromethylimidazo-[1,2-a]-pyridin- 6-yl)cyclohexanecarbothioamide (an about 4:1 mixture of L- and M-diastereomers)

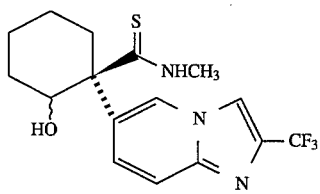

1.86 g of 1-(2-trlfluoromethylimidazo-[ 1,2-a]pyridin-6-yl)-N-methyl-2-oxocyclohexanecarbothioamide was suspended in 17 ml of methanol. The obtained suspension was cooled with ice, followed by the addition of 0.08 g of sodium borohydride. The obtained mixture was stirred for one hour, followed by the addition of water. The resulting mixture was extracted with chloroform. The organic phase was dried over anhydrous magnesium sulfate and freed from the solvent by distillation. The obtained solid was recrystallized from ethyl acetate/n-hexane to give 1.53 g of the title compound as a white solid (yield: 84%).

This solid comprised two diastereomers at a ratio of about 4:1, but was used in the subsequent reaction without any additional purification.

NMR (400 MHz, δ, CDCl₃):

1.18–1.32(1H, m), 1.44–1.98(5H, m), 2.27, 2.04(total 1H, m), 2.40, 3.01(total 1H, m), 3.16, 3.34(total 3H, d, J=4.6 Hz), 3.38, 5.51(total 1H, δ3.38: d, J=3.8 Hz, 65.51: br, disappeared in D₂O), 4.79, 4.32(total 1H, m), 7.41, 7.01(total 1H, d, J=9.7 Hz), 7.54, 7.32(total 1H, dd, J=1.8, 9.7 Hz), 7.76, 7.65(total 1H, m), 8.78, 7.98(total 1H, m), 8.03, 10.53(total 1H, br)

Preparative Example 8

(−)-(1S, 2R)-2-Hydroxy-1-(imidazo[1,2-a]pyridin-6-yl)-N-methylcyclohexanecarbothioamide

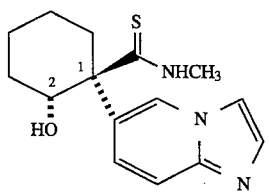

42.91 g of (±)-1-(imidazo[1,2-a]pyridin-6-yl)-N-methyl-2-oxocyclohexanethioamide was suspended in 500 ml of methanol, followed by the addition of 1.70 g of sodium borohydride at room temperature in portions. The obtained mixture was stirred for 30 minutes, Followed by the addition of 1 l of water. The resulting mixture was filtered to give 36.32 g of a pale-yellow powder as a filter cake. This powder and 7.29 g of (+)-dibenzoyl-D-tartaric acid were dissolved in 1.8 l of a 1:5 mixture of water and ethanol in a hot state. The obtained solution was allowed to stand at room temperature for 12 hours to give a precipitate. This precipitate was recovered by filtration to give 21.56 g of an orange needle, which was suspended in 200 ml of water, followed by the addition of 50 ml of concentrated aqueous ammonia. The obtained mixture was stirred at room temperature for one hour and filtered to recover an insoluble matter. 9.51 g (>99% ee) of the title compound was obtained as a pale-orange powder (yield: 26%).

The optical purity was determined by high-performance liquid chromatography using a chiral column.

<Conditions of the liquid chromatography> column: CHIRALCEL (resistered trademark) OJ (a product of Daicel Chemical Industries, Ltd.) (250 mm×4.6 mm I.D.), eluent: a 4:1 (v/v) mixture of n-hexane and 2-propanol, column temp.: room temp., flow rate: 1 ml/min, method of detection: ultraviolet absorption (254 nm), and retention time: 13.3 min (13.3 and 21.5 min with respect to the racemic modification), m.p. (°C.): 244–246 (dec.)

specific rotation $[α]_D^{28}$: −44° (c=0.68, DMF)

NMR (400 MHz, δ, DMSO-d₆):

1.26–1.40(3H, m), 1.52–1.72(2H, m), 1.93–2.02(1H, m), 2.15–2.25(1H, m), 2.47–2.55(1H, m), 2.92(3H, d, J=4.4 Hz), 4.60–4.66 (1H, m), 4.88–494(1H, m), 7.32(1H, dd, J=1.8, 9.5 Hz), 7.44(1H, d, J=9.5 Hz), 7.51(1H, d, J=1.3 Hz), 7.96(1H, m), 8.63(1H, m), 9.20–9.30(1H, m)

Preparative Example 9

2-(N-t-Butoxycarbonylglycyloxy)-1-imidazo[1,2-a]-pyridin-6-yl)-N'-methylcyclohexanecarbothioamide

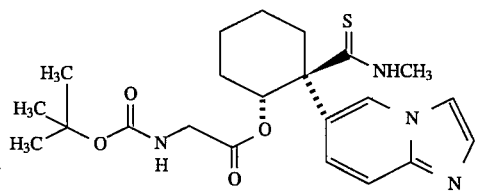

2.00 g of 2-hydroxy-1-(imidazo[1,2-a]pyridin-6-yl)-N-methylcyclohexane-carbothioamide (M-form), 2.42 g of N-t-butoxycardonylglycine, 2.86 g of N,N'-dicyclohexylcarbodiimide and 0.84 g of 4-dimethylaminopyridine were added to 35 ml of N,N-dimethylformamide. The obtained mixture was stirred at room temperature for 16 hours, followed by the addition of ethyl acetate and a saturated aqueous solution of sodium hydrogencarbonate. The obtained mixture was filtered to remove insolubles. The ethyl acetate phase was recovered, washed with water and a saturated aqueous solution of common salt, dried over anhydrous magnesium sulfate, and freed from the solvent by distillation. The residue was purified by silica gel column chromatography (solvent: a dichloromethane/methanol (30:1) mixture) and crystallized from dichloromethane/ether to give 2.66 g of the title compound as a white powder (yield: 86%).

m.p. (°C.): 140–142

NMR (400 MHz, δ, CDCl₃):

1.37(9H, s), 1.32–1.47(1H, s), 1.48–1.69(3H, m), 1.72–1.85(1H, m), 2.24–2.38(2H, m), 2.53–2.66(1H, m), 3.12(3H, d, J=3.6 Hz), 3.59(1H, dd, J=4.8, 1.8 Hz), 3.54–3.70(1H, m), 3.88(1H, dd, J=4.8, 18 Hz), 4.96–5.08(1H, m), 5.90–6.01(1H, m), 7.13(1H, dd, J=1 Hz, 9.4 Hz), 7.30(1H, d, J=9.4 Hz), 7.57(1H, s), 7.58(1H, d, J=1 Hz), 8.07(1H, brs), 8.43(1H, s)

Preparative Examples 10 to 20

The following compounds were each prepared in a similar manner to that of the Preparative Example 9.

Preparative Example 10

2(N-t-Butoxycarbonylglycyloxy)-N'-methyl-1-(4-methylimidazol-1-yl)cyclohexanecarbothioamide

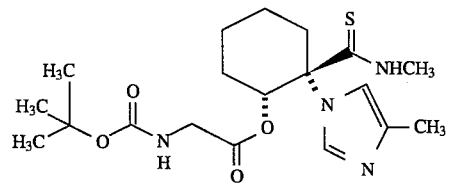

m.p. (°C.): 191–193

NMR (400 MHz, δ, CDCl₃):

1.27(1H, m), 1.46(9H, s), 1.48–1.78(4H, m), 2.06(1H, m), 2.29(3H, d, J=0.9 Hz), 2.38(1H, m), 2.81(1H, m), 3.04(3H, d, J=4.8 Hz), 3.78(1H, dd, J=5.1 Hz, 18.1 Hz), 3.99 ( 1H, dd, J=6.4 Hz, 18.1 Hz), 5.00(1H, br) 6.01(1H, dd, J=3.7 Hz, 11.7 Hz), 6.77(1H, br), 7.26(1H, s), 7.79(1H, s)

Preparative Example 11

2-(N-t-Butyoxycarbonylglycyloxy)-N'-ethyl-1-(imidazo-[1,2-a]pyridin-6-yl)cyclohexane-carbothioamide

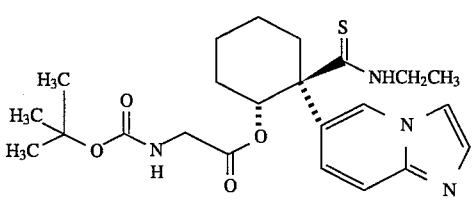

m.p. (°C.): 206–210

NMR (400 MHz, δ, CDCl₃):

1.11(3H, t, J=7.3 Hz), 1.32–1.46(1H, m), 1.38(9H, s), 1.51–1.68(3H, m), 1.80(1H, m), 2.23–2.38(2H, m), 2.59(1H, m), 3.53–3.75(3H, m), 3.91(1H, dd, J=6.2 Hz, 17.9 Hz), 5.01(1H, br), 5.99(1H, dd, J=2.9, 8.6 Hz), 7.21(1H, dd, J=1.3, 9.5 Hz), 7.41(1H, br), 7.49(1H, d, J=9.5 Hz), 7.62(1H, s), 7.63(1H, s), 8.47(1H, s)

Preparative Example 12

2-(N-t-Butocycarbonylglycyloxy)-N'-methyl-1-(2-methylimidazo[1,2-a]pyridin-6-yl)cyclo-hexanecarbothioamide

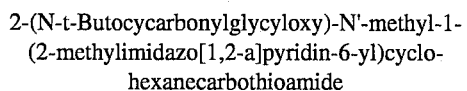

m.p. (°C.): 229–233 (dec.)

NMR (400 MHz, δ, CDCl₃):

1.34(9H, s), 1.40(1H, m), 1.50–1.85(4H, m), 2.22(1H, m), 2.35(1H, m), 2.46(3H, s), 2.58(1H, m), 3.08(3H, d, J=4.8 Hz), 3.62(1H, dd, J=5.0, 17.9 Hz), 3.91(1H, dd, J=6.0, 17.9 Hz), 4.97(1H, br), 5.95(1H, dd, J=3.5, 9.3 Hz), 7.15(1H, d, J=9.7 Hz), 7.37(1H, s), 7.39(1H, d, J=9.7 Hz), 7.49(1H, br), 8.40(1H, s)

Preparative Example 13

2-(N-t-Butoxycarbonylglycyloxy)-N'-methyl-1-(2-trifluoromethylimidazo[1,2-a]pyridin-6-yl)-cyclohexanecarbothioamide

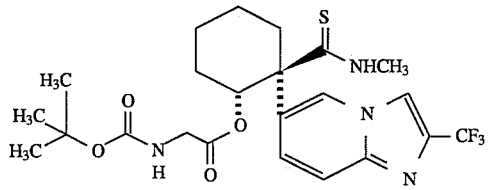

m.p. (°C.): 199–204

NMR (400 MHz, δ, CDCl₃):

1.34(9H, s), 1.37(1H, m), 1.52–1.95(4H, m), 2.28(1H, m), 2.37(1H, m), 2.60(1H, m), 3.13(3H, d, J=4.6 Hz), 3.63 ( 1H, dd, J=5.6, 18.0 Hz), 3.87(1H, dd, J=6.0, 18.0 Hz), 5.00(1H, m), 5.99(1H, dd, J=2.8, 8.4 Hz), 7.37(1H, dd, J=1.5, 9.5 Hz), 7.43(1H, d, J=9.5 Hz), 7.70(1H, br), 7.88(1H, s), 8.48(1H, s)

Preparative Example 14

2-(N-t-Butoxycarbonylsarcosyloxy)-1-imidazo[1,2-a]-pyridin-6-yl)-N'-methylcyclohexanecarbothioamide

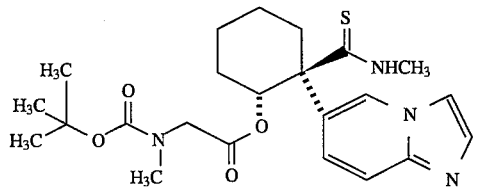

NMR (400 MHz, δ, CDCl₃):

1.33, 1.41(total 9H, s), 1.22–1.96(5H, m), 2.17–2.41(2H, m), 2.53–2.66(1H, m), 2.71, 2.77(total 3H, s), 3.09, 3.11(total 3H, d, J=4.8 Hz), 3.62, 3.67(total 1H, d, J=17.9 Hz), 4.01, 4.05(total 1H, d, J=13.0 Hz), 5.90, 6.14(total 1H, dd, J=3.5, 8.9 Hz), 7.18, 7.23(total 1H, dd, J=1.3, 9.5 Hz), 7.43, 7.50(total 1H, d, J=9.5 Hz), 7.54–7.92(3H, m), 8.48(1H, s)

Preparative Example 15

2-(N-t-Butoxycarbonyl-β-alanyloxy)-1-(imidazo-[1,2-a]pyridin-6-yl)-N'-methylcyclo-hexanecarbothioamide

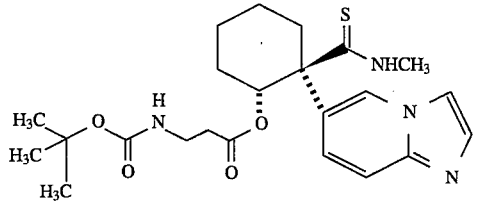

m.p. (°C.): 183–185

NMR (400 MHz, δ, CDCl₃):

1.30–1.46(1H, m), 1.41(9H, s), 1.52–1.82(4H, m), 2.20(1H, m) 2.30–2.39(2H, m), 2.47(1H, m), 2.62(1H, m), 3.09(3H, d, J=4.8 Hz), 3.24(1H, m), 3.39(1H, m), 4.89(1H, br), 5.97(1H, dd, J=3.1, 8.8 Hz), 7.22(1H, dd, J=1.3, 9.5 Hz), 7.46(1H, br), 7.52(1H, d, J=9.5 Hz), 7.64(1H, d, J=1.3 Hz), 7.68(1H, s), 8.56(1H, s)

Preparative Example 16

2-(2-(N-t-Butoxycarbonylamino)isobutyryloxy)-1-(imidazo[1,2-a]pyridin-6-yl)-N'-methylcyclohexane-carbothioaside

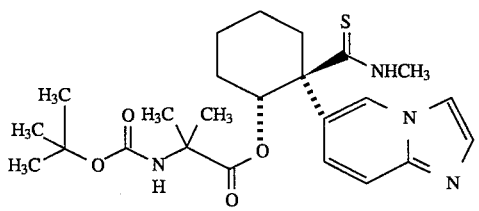

m.p. (°C.): 176–178

NMR (400 MHz, δ, CDCl₃):

1.18–1.85(19H, m), 2.23(1H, m), 2.38(1H, m), 2.65(1H, m), 3.08(3H, d, J=4.8 Hz), 4.98(1H, br), 5.93(1H, dd, J=3.3, 9.5 Hz), 7.24 (1H, m), 7.48–7.68(4H, m), 8.56(1H, br)

Preparative Example 17

2-(N,t-Butcxycarbonylalanyloxy)-1-(imidazo-[1,2-a]-pyridin-6yl)-N'-methylcyclohexanecarbothioamide (an about 3:2 mixture of diastereomers)

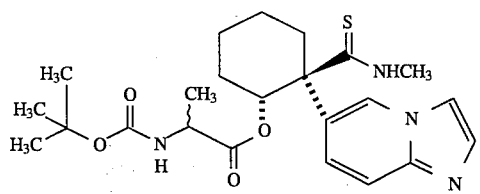

NMR (400 MHz, δ, CDCl₃):

1.14–1.88(5H, m), 1.03, 1.27(total 3H, d, J=7.1 Hz), 1.35, 1.38(total 9H, s), 2.20–2.41(2H, m), 2.56–2.68(1H, m), 3.09(3H, d, J=4.8 Hz), 4.05–4.26(1H, m), 4.89, 5.00(total 1H, d, J=8.0 Hz), 5.99(1H, dd, J=3.1, 8.8 Hz), 7.19, 7.21(total 1H, dd, J=1.8, 9.51 Hz), 7.39–7.49(1H, m), 7.43, 7.47(total 1H, d, J=9.5 Hz), 7.58–7.64(2H, m), 7.67, 7.85(total 1H, br), 8.47, 8.50(total 1H, s)

Preparative Example 18

2-(N-t-Butoxycarbonylphenylalanyloxy)-1-(imidazo-[1,2-a]pyridin-6-yl)-N'-methylcyclohexane-carbothioamide (an about 3:2 mixture of diastereomers)

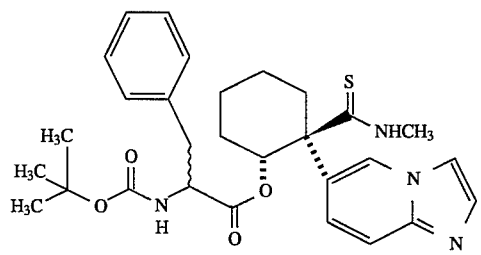

NMR (400 MHz, δ, CDCl₃):

1.18–1.82(5H, m), 1.33, 1.35(total 9H, s), 2.01–2.77(3H, m), 2.96–3.10(5H, m), 4.37, 4.46(total 1H, m), 4.86, 4.91(total 1H, d, J=8.6 Hz), 5.83, 5.89(total 1H, m), 6.98–7.33(6H, m), 7.38–7.65(4H, m), 8.23, 8.54(total 1H, s)

Preparative Examples 19

2-(N-t-Butoxycarbonylprolyloxy)-1-(imidazo-[1,2-a]pyridin-6-yl)-N'-methylcyclohexane-carbothioamide (an about 1:1 mixture of diastereomers)

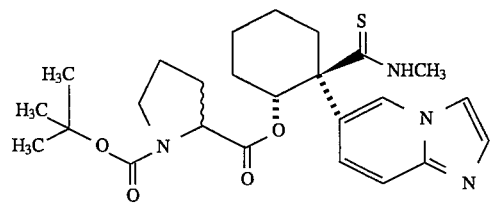

NMR (400 MHz, δ, CDCl₃):

1.20–1.94(18H, m), 2.12–2.70(3H, m), 3.04, 3.09(total 3H, d, J=4.8 Hz), 3.25–3.55(2H, m), 4.26–4.33(1H, m), 6.07, 6.14(total 1H, m), 7.09(1H, m), 7.15–7.24(1H, m), 7.55–7.70(3H, m), 8.59, 8.67 (total 1H, s)

Preparative Example 20

2-(N-t-Butoxycarbonyl-β-benzylaspartyloxy)-1-(imidazo[1,2-a]pyridin-6-yl)-N'-methylcyclohexane-carbothioamide (an about 1:1 mixture of diastereomers)

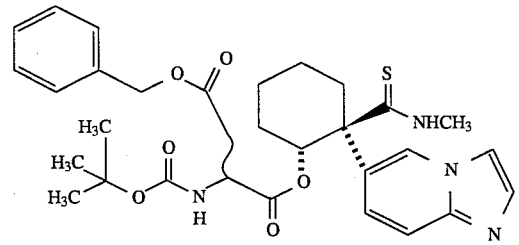

NMR (400 MHz, δ, CDCl₃):

1.27–1.88(8H, m), 1.30, 1.35(total 9H, s), 2.23–2.37(2H, m), 2.52–2.76(2H, m), 2.82–2.95(1H, m), 3.08, 3.12(total 3H, d, J=4.6 Hz), 4.30–4.49(1H, m), 4.91–5.04(2H, m), 5.32, 5.54(total 1H, m), 5.81, 5.93(total 1H, m), 7.03–7.13(1H, m), 7.21–7.40(6H, m), 7.55–7.65(2H, m), 8.00–8.20(1H, br), 8.46–8.52(1H, m)

Preparative Example 21

2-(N-t-Butoxycarbonylvalyloxy)-1-(imidazo[1,2-a]-pyridin-6-yl])-N'-methylcyclohexanecarbothioamide (M-form)

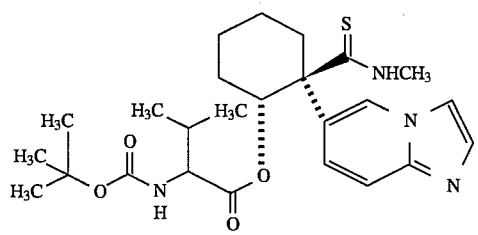

1.0 g of 2-hydroxy-1-(imidazo[1,2-a]pyridin-6-yl)-N-methylcyclohexanecarbothioamide, 1.32 g of N,N'-dicyclohexylcarbodiimide, 1.44 g of (L)-N-t-butoxycarbonylvaline and 0.4 g of 4-dimethylaminopyridine were added to 20 ml of N,N-dimethylformamide. The obtained mixture was stirred at room temperature for 17 hours, followed by the addition of ethyl acetate and a saturated aqueous solution of sodium hydrogencarbonate. The resulting mixture was filtered to remove insolubles. The ethyl acetate phase was recovered, washed with water and a saturated aqueous solution of common salt, dried over anhydrous magnesium sulfate, and freed from the solvent by distillation. The residue was purified by silica gel column chromatography (solvent: a dichloromethane/methanol (40:1) mixture) to give 0.41 g (254) of a lower-polarity diastereomer (L-form) as a white powder and 0.52 g (31%) of a higher-polarity one (M-form) as a white powder.

m.p. (°C.): 228–229

NMR (400 MHz, δ, CDCl₃):

0.55(3H, br d, J=6.2 Hz), 0.78(3H, d, J=6.8 Hz), 1.18–1.38(2H, m), 1.41(9H, s), 1.48–1.88(4H, m), 2.29(1H, m), 2.37(1H, m), 2.65(1H, m), 3.08(3H, d, J=4.8 Hz), 4.10 (1H, dd, J=4.9 Hz, 9.2 Hz), 4.96(1H, d, J=9.2 Hz), 5.95 (1H, m), 7.24(1H, m), 7.39(1H, br), 7.56(1H, d, J=9.7 Hz), 7.66(1H, s), 7.67(1H, s) 8.58(1H, br s)

Preparative Examples 22 to 24

The following compounds were each prepared in a similar manner to that of the Preparative Example 21.

Preparative Example 22

2-(N-t-Butoxycarbonylvalyloxy)-1-(imidazo[1,2-a]-pyridin-6yl)-N'-methylcyclohexanecarbothioamide (L-form)

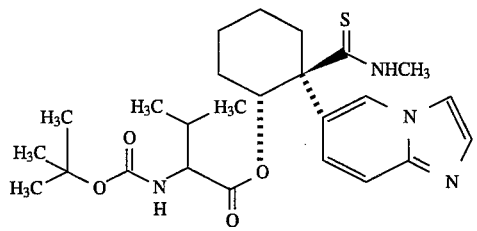

m.p. (°C.): 248–249

NMR (400 MHz, δ, CDCl₃):

0.79(3H, d, J=6.8 Hz), 0.87(3H, d, J=6.8 Hz), 1.20–1.34(1H, m), 1.37(9H, s), 1.51–1.69(3H, m), 1.78(1H, m), 2.00(1H, m), 2.24–2.40(2H, m), 2.59(1H, m), 3.10(3H, d, J=4.4 Hz), 3.98(1H, dd, J=5.5, 8.4 Hz), 4.82(1H, d, J=8.4 Hz), 6.00(1H, dd, J=3.5, 8.6 Hz), 7.17(1H, m), 7.35(1H, br d, J=9.9 Hz), 7.56(1H, s), 7.60(1H, s), 7.94(1H, br), 8.45(1H, br s)

Preparative Example 23

2-(N-t-Butoxycarbonyl-O-t-butylseryloxy)-1-(imidazo-[1,2-a]pyridin-6-yl)-N'-methylcyclohexanecarbothioamide (M-form)

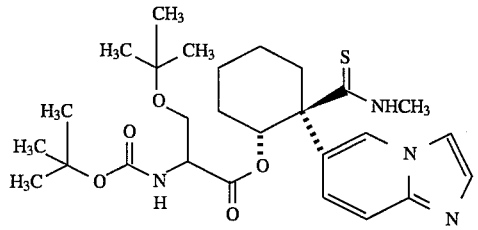

m.p. (°C.): 201–205

NMR (400 MHz, δ, CDCl₃):

1.06(9H, s), 1.38 (9H, s), 1.42(1H, m), 1.50–1.70(3H, m), 1.82(1H, m), 2.25–2.40(2H, m), 2.59(1H, m), 3.11(3H, d, J=4.4 Hz), 3.48(1H, m), 3.65(1H, m), 4.16(1H, m), 5.16(1H, d, J=8.2 Hz), 5.93(1H, m), 7.10–7.21(1H, m), 7.29–7.36(1H, m), 7.54–7.65(2H, m), 7.79–8.10(1H, m), 8.41–8.50(1H, m)

Preparative Example 24

2-(N-t-Butyoxycarbonyl-O-t-butylseryloxy)-1-(imidazo-[1,2-a]pyridin-6-yl)-N'-methylcyclohexane-carbothioamide (L-form)

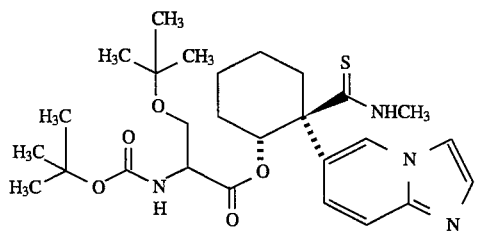

m.p. (°C.): 219–223 (dec.)
NMR (400 MHz, δ, CDCl$_3$):
1.07(9H, s), 1.21(9H, s), 3.34(1H, m), 1.50–1.62(2H, m), 1.68(1H, m), 1.90(1H, m), 2.18(1H, m), 2.38(1H, m), 2.65(1H, m), 3.09(3H, d, J=4.6 Hz), 3.45(1H, dd, J=3.5, 9.2 Hz), 3.70(1H, m), 4.21(1H, m), 5.33(1H, d, J=8.1 Hz), 5.71(1H, m), 7.12–7.19(1H, m), 7.48–7.54(1H, m), 7.62–7.74 (3H, m), 8.52–8.58(1H, m)

Preparative Example 25

(+)-(1S, 2F)-2-(N-t-Butoxycarbonylglycycloxy)-1-(imidazo-[1,2-a]pyridin-6-yl)-N'-methylcyclohexane-carbothioamide

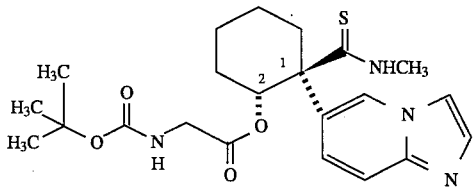

5.11 g of the (−)-(1S, 2R)-2-hydroxy-1-(imidazo[1,2-a]pyridin-6-yl)-N-methylcyclohexanecarbothioamide, 6.2 g of N-t-butoxycarbonylglycine, 7.3 g of N,N'-dicyclohexylcarbodiimide and 2.16 g of 4-dimethylaminopyridine were added to 60 ml of N,N-dimethylformamide. The obtained mixture was stirred at room temperature overnight.

The precipitated solid was filtered out. The filtrate was concentrated in a vacuum, followed by the addition of ethyl acetate. The obtained solution was washed with water and a saturated aqueous solution of common salt, dried over anhydrous magnesium sulfate, and freed from the solvent by distillation. The residue was purified by silica gel column chromatography (solvent: a 30:1 dichloromethane/methanol mixture) and crystallized from n-hexane/ethyl acetate to give 6.89 g of the title compound as a white powder (yield: 88%).

m.p. (°C.): 172–173
specific rotation $[\alpha]_D^{28}$: +24.3° (c=0.68, chloroform)
NMR (400 MHz, δ, CDCl$_3$)
1.37(9H, s), 1.32–1.47(1H, s), 1.48–1.69(2H, m), 1.72–1.85(1H, m), 2.24–2.38(2H, m), 2.53–2.66(1H, m), 3.12(3H, d, J=3.6 Hz), 3.59(1H, dd, J=4.8, 18 Hz), 3.54–3.70(1H, m), 3.88(1H, dd, J=4.8, 18 Hz), 4.96–5.08(1H, m), 5.90–6.01(1H, m), 7.13(1H, dd, J=1, 9.4 Hz), 7.30(1H, d, J=9.4 Hz), 7.57(1H, s), 7.58(1H, d, J=1 Hz), 8.07(1H, br s), 8.43(1H, s)

Preparative Example 26

2-(2-(1-Naphthalenesulfonamido)ethoxy)-1-(imidazo-[1,2-a]pyridin-6-yl)-1-((4-methoxybenzylthio)-(methylimino)methyl)cyclohexane

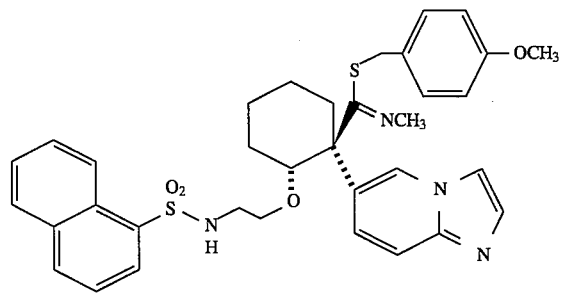

1.31 g of 2-(imidazo[1,2-a]pyridin-6-yl)-2-((4-methoxybenzyl)(methylimino)methyl)cyclohexanol was suspended in 50 ml of tetrahydrofuran. The obtained suspension was cooled to −60°C., followed by the addition of 0.4 g of potassium t-butoxide. The obtained mixture was stirred for 2.5 hours, followed by the addition of 0.82 g of N-(1-naphthalenesulfonyl)aziridine. The obtained mixture was gradually brought to 0°C. and stirred under cooling with ice for 5.5 hours, followed by the addition of a saturated aqueous solution of ammonium chloride. The resulting mixture was extracted with chloroform. The chloroform phase was dried over anhydrous magnesium sulfate and freed from the solvent by distillation. The residue was purified by silica gel column chromatography (solvent: a 40:1 dichloromethane/methanol mixture) to give 0.4 g of the title compound as a white amorphous substance (yield: 19%).

NMR (400 Hz, δ, CDCl$_3$):
1.43(1H, m), 1.68(1H, m), 1.76–1.84(2H, m), 2.04(1H, m), 2.44(1H, m), 2.74–2.90(2H, m), 3.01(1H, m), 3.33(1H, d, J=12.3 Hz), 3.50(1H, m), 3.58(1H, d, J=12.3 Hz), 3.60(3H, s), 3.68–3.75(5H, m), 4.22(1H, br s), 4.54(1H, br), 6.50–6.56(2H, m), 6.61–6.67(2H, m), 7.15(1H, dd, J=1.8, 9.5 Hz), 7.38–7.61(7H, m), 7.65(1H, d, J=1.1 Hz), 8.02(1H, m)

Preparative Example 27

2-(2-Benzenesulfonamidoethoxy)-1-(imidazo-[1,2-a]-pyridin-6-yl)-1-((4-methoxybenzythio)(methylimino)-methyl)cyclohexane

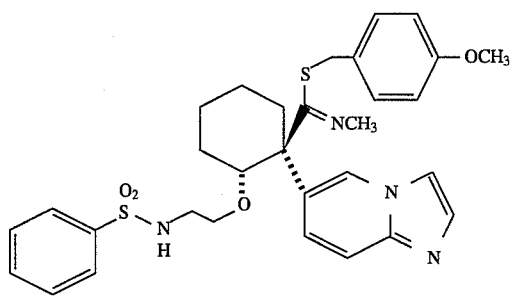

The title compound was prepared in the same manner as that of the Preparative Example 26 except that N-benzenesulfonylaziridine was used instead of the N-(1-naphthalenesalfonyl)aziridine.

NMR (400 MHz, δ, CDCl₃):

1.12–1.40(2H, m), 1.52–1.66(2H, m), 1.88(1H, m), 2.34(1H, m), 2.68(1H, m), 2.85(1H, m), 2.93(1H, m), 3.33(1H, d, J=12.3 Hz), 3.38(1H, m), 3.59(3H, s), 3.68–3.74(5H, m), 4.13(1H, br s), 4.81(1H, br), 6.50–6.56(2H, m), 6.61–6.67(2H, m), 7.06(1H, dd, J=1.8, 9.5 Hz), 7.41–7.50(3H, m), 7.56–7.66(3H, m), 7.90(1H, m), 7.94(1H, dd, J=1.6, 7.9 Hz), 8.04(1H, d, J=8.2 Hz), 8.10(1H, dd, J=1.1, 7.3 Hz), 8.42(1H, d, J=8.8 Hz)

Preparative Example 28

2-Glycyloxy-1-(imidazo[1,2a]pyridin-6-yl)-N-methylcyclohexanecarbothioamide

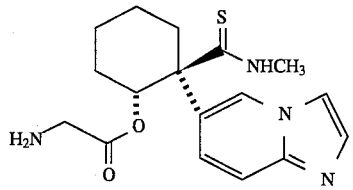

2.43 g of the 2-(N-t-butoxycarbonylglycyloxy)-1-(imidazo[1,2-a]pyridin-6-yl)-N'-methylcyclohexanecarbothioamide prepared in the Preparative Example 9 was dissolved in 5 ml of dichloromethane. The obtained solution was cooled with ice, followed by the addition of 5 ml of trifluoroacetic acid. The obtained mixture was stirred for one hour, followed by the addition of ice-water. The resulting mixture was alkalinized with sodium carbonate and extracted with dichloromethane. The organic phase was dried over anhydrous magnesium sulfate and freed from the solvent by distillation. The obtained solid was washed with ether to give 1.71 g of the title compound as a pale-yellow powder (yield: 92%).

This powder was used in the subsequent reaction without any additional purification.

Preparative examples 29 to 31

The following compounds were each prepared in a similar manner to that of the Preparative Example 28.

Preparative Example 29

2-Glycyloxy-N-methyl-1-(4-methylimidazol-1-yl)-cyclohexanecarbothioamide

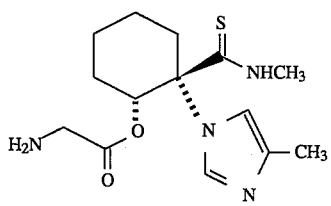

Preparative Example 30

2-Prolyloxy-1-(imidazo[1,2-a]pyridin-6-yl)-N-methylcyclohexanecarbothioamide (an about 1:1 mixture of diastereomers)

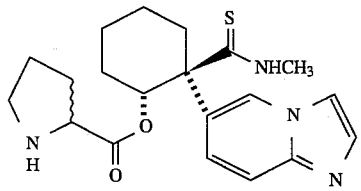

Preparative Example 31

1-(imidazo[1,2-a]pyridin-6-yl)-N-methyl-(2-sarcoxyloxy)-cyclohexanecarbothioamide

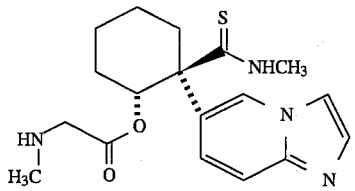

Preparative Example 32

2-(β-Benzylaspartyloxy)-1-(imidazo[1,2-a]pyridin-6-yl)-N-methylcyclohexanecarbothioamide (a single diastereomer)

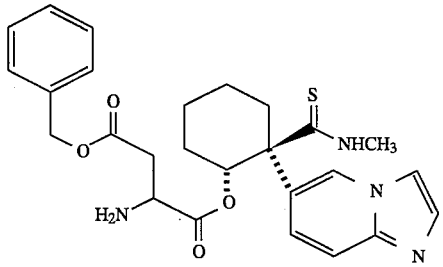

1.10 g of the 2-(N-t-butoxycarbonyl-β-benzylasparty-loxy)- 1-(imidazo[1,2-a]pyridin-6-yl)-N'-methylcyclohex-anecarbothioamide prepared in the Preparative Example 20 was dissolved in 5 ml of dichloromethane, followed by the addition of 5 ml of trifluoroacetic acid. The obtained mixture was stirred under cooling with ice for one hour, followed by the addition of water. The resulting mixture was alkalinized with sodium hydrogencarbonate and extracted with chloroform. The chloroform phase was dried over anhydrous magnesium sulfate and freed from the solvent by distillation. The residue was purified by silica gel column chromatography (solvent: a 10:1 dichloromethane/methanol mixture) to give 0.67 g of a higher-polarity diastereomer as a colorless oil (yield: 71%).

NMR (400 MHz, δ, CDCl$_3$):

1.41–1.74(7H, m), 2.21–2.33(2H, m), 2.52–2.77(3H, m), 3.11(3H, d, J=4.6 Hz), 3.54(1H, m), 5.05(1H, d, J=12.3 Hz), 5.09(1H, d, J=12.3 Hz), 6.03(1H, dd, J=2.9, 7.5 Hz), 7.10–7.19(1H, m), 7.28–7.38(6H, m), 7.54–7.58(2H, m), 7.98–8.11(1H, br), 8.41–8.45(1H, m)

Preparative Example 33

2-Glycyloxy-1-(imidazo[1,2-a]pyridin-6-yl)-N-methyl-cyclohexanecarbothioamide dihydrochloride

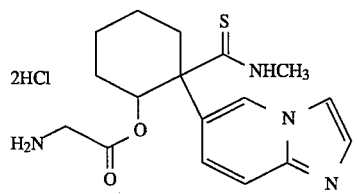

6.0 g of the 2-(N-t-butoxycarbonylglycyloxy)-1-(imidazo[1,2-a]pyridin-6-yl)-N'-methylcyclohexanecarbothioamide prepared in the Preparative Example 9 was dissolved in 120 ml of chloroform, followed by the addition of 30 ml of 4N hydrogen chloride/ethyl acetate. The obtained mixture was stirred at room temperature for 4 hours and concentrated to dryness. 5.8 g of the title compound was obtained as a white powder.

This powder was used in the subsequent reaction without any additional purification.

Preparative Example 34

(1S, 2R)-2-Glycyloxy-1-(imidazo[1,2-a]pyridin-6-yl)-N-methylcyclohexanecarbothioamide dihydrochloride

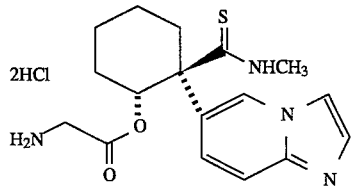

12.0 g of the (+)-(1S, 2R)-2-(N-t-butoxycarbonylgycy-loxy)- 1-(imidazo[ 1,2-a]pyridin-6-yl)-N'-methylcyclohex-anecarbothioamide prepared in the Preparative Example 25 was dissolved in 250 ml of chloroform, followed by the addition of 60 ml of 10% to hydrogen chloride/ethyl acetate. The obtained mixture was stirred at room temperature for 12 hours and concentrated, followed by the addition of ethyl acetate. The resulting mixture was filtered to recover insolubles. 11.3 g of the title compound was obtained as a pale-orange powder (yield: 100%).

This powder was used in the subsequent reaction without any additional purification.

Preparative Example 35

2-(N'-(N'-t-Butoxycarbonylycyl))glycyloxy)-1-(imidazo-[1,2-a]pyridin-6-yl)-N''-methylcyclohexanecarbothioamide

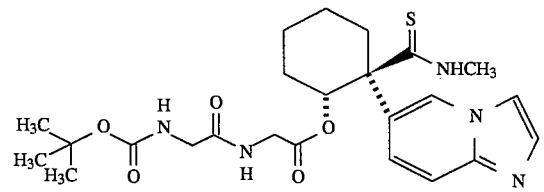

0.5 g of the 2-glycyloxy-1-(imidazo[1,2-a]-pyridin-yl)-N-methylcyclohexanecarbothioamide prepared in the Preparative Example 33, 0.3 g of N-t-butoxycarbonylglycine, 0.35 g of N,N'-dicyclohexylcarbodiimide and 0.23 g of N-hydroxybenzotriazole were added to 10 ml of acetonitrile. The obtained mixture was stirred at room temperature for 14 hours, followed by the addition of methanol. The formed insoluble matter was filtered out. The filtrate was concentrated, followed by the addition of dichloromethane. The formed insoluble matter was filtered out and the filtrate was purified by silica gel column chromatography (solvent: dichloromethane/methanol (30:1 to 20:1)). The obtained oil was crystallized from acetonitrile to give 0.67 g of the title compound as a white powder (yield: 95%).

m.p. (°C.): 177–180

NMR (400 MHz, δ, CDCl$_3$):

1.31–1.49(1H, m), 1.44(9H, s), 1.50–1.69(3H, m), 1.84(1H, m), 2.25(1H, m), 2.34(1H, m), 2.61(1H, m), 3.10(3H, d, J=4.6 Hz), 3.64–3.84(3H, m), 4.04(1H, dd, J=5.7, 17.6 Hz), 5.18(1H, br), 5.98(1H, m), 6.77(1H, br), 7.19(1H, d, J=9.5 Hz), 7.43(1H, d, J=9.5 Hz), 7.60(1H, 7.67(1H, s), 7.84(1H, br), 8.47(1H, s)

Preparative Example 36

2-(N-(N'-t-Butoxycarbonylglycyl)sarcoxyloxy)-1-(imidazo[1,2-a]pyridin-6-yl)-N''-methylcyclohexanecarbothioamide

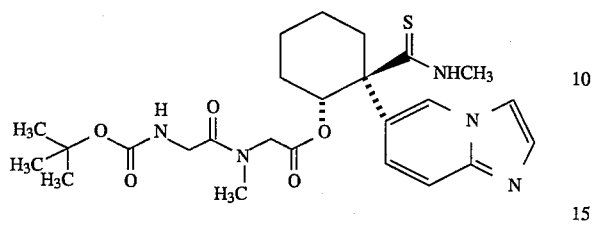

The title compound was prepared by the use of the compound prepared in the Preparative Example 31 as the starting material in a similar manner to that of the

Preparative Example 35

NMR (400 MHz, δ, CDCl$_3$):
1.21, 1.39(total 9H, s), 1.18–1.85(5H, m), 2.12–2.40(2H, m), 2.51–2.74(1H, m), 2.78, 2.88(total 3H, s), 3.04, 3.10(total 3H, d, J=4.6 Hz), 3.71–4.15(4H, m), 5.12, 5.25(total 1H, br), 6.02, 6.10(total 1H, dd, J=3.5, 9.3 Hz), 7.15, 7.25(total 1H, dd, J=1.8, 9.5 Hz), 7.36, 7.77(total 1H, br), 7.56, 7.59(total 1H, d, J=9.5 Hz), 7.63, 7.66(total 1H, d, J=1.8 Hz), 7.72, 7.77(total 1H, s), 8.36, 8.49(total 1H, s)

EXAMPLE 1

2-(N-Benzenesulfonylglycyloxy)-1-(imidazo[1,2-a]pyridin-6-yl)-N'-methylcyclohexanecarbothioamide

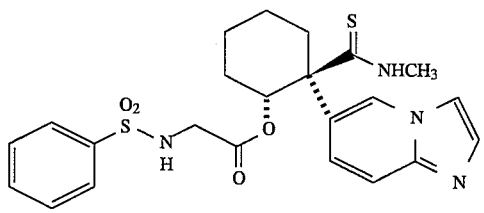

0.5 g of the 2-glycyloxy-1-(imidazo[1,2-a]-pyridin-6-yl)-N-methylcyclohexanecarbothioamide prepared in the Preparative Example 28 was suspended in 3 ml of dichloromethane, followed by the addition of 0.13 ml of pyridine. The obtained mixture was stirred under cooling with ice, followed by the dropwise addition of a solution of 0.2 ml of benzenesulfonyl chloride in 2 ml of dichloromethane. After 40 minutes, concentrated aqueous ammonia was added to the resulting mixture, followed by the addition of water. The obtained mature was extracted with chloroform. The chloroform phase was dried over anhydrous sodium sulfate and freed from the solvent by distillation. The residue was purified by silica gel column chromatography (solvent: a 40:1 dichloromethane/methanol mixture), crystallized from dichloromethane/ethyl acetate and recrystallized from ethyl acetate to give 0.49 g of the title compound as a white needle (yield: 72%).

m.p. (°C.): 226–227

NMR (400 MHz, δ, CDCl$_3$):
1.38(1H, m), 1.51–1.81(4H, m), 2.18(1H, m), 2.37(1H, m), 2.57(1H, m), 3.06(3H, d, J=4.8 Hz), 3.61(1H, d, J=17.8 Hz), 3.72(1H, d, J=17.8 Hz), 5.42(1H, br), 5.94(1H, dd, J=3.5, 9.3 Hz), 7.18(1H, dd, J=1.8, 9.5 Hz), 7.45–7.54(3H, m), 7.54–7.63(3H, m), 7.70(1H, s), 7.77–7.81(2H, m), 8.59(1H, m)

EXAMPLE 2

2-(N-(2-Furansulfonyl)glycyloxy)-1-(imidazo[1,2-a]-pyridin-6-yl)-N'-methylcyclohexanecarbothioamide

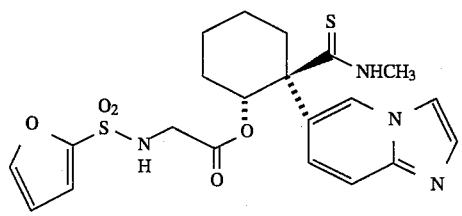

0.2 g of the 2-glycyloxy-1-(imidazo[1,2-a]-pyridin-6-yl)-N-methylcyclohexanecarbothioamide prepared in the Preparative Example 28 was suspended in 2 ml of pyridine. The obtained suspension was cooled with ice, followed by the dropwise addition of 0.11 g of 2-furansulfonyl chloride. The obtained mixture was stirred for 2 hours, followed by the addition of dilute aqueous ammonia. The resulting mixture was extracted with chloroform. The chloroform phase was dried over anhydrous magnesium sulfate and freed from the solvent by distillation. The residue was purified by silica gel column chromatography (solvent: a 40:1 dichloromethane/methanol mixture) and crystallized from ether to give 0.15 g of the title compound as a pale-yellow powder (yield: 54%).

NMR (400 MHz, δ, CDCl$_3$):
1.38(1H, m), 1.49–1.84(4H, m), 2.21(1H, m), 2.37(1H, m), 2.58(1H, m), 3.07(3H, d, J=4.6 Hz), 3.72(1H, d, J=17.9 Hz), 3.81(1H, d, J=17.9 Hz), 5.97(1H, dd, J=3.7, 9.5 Hz), 6.47(1H, dd, J=1.8, 3.5 Hz), 6.97(1H, dd, J=0.9, 3.5 Hz), 7.15–7.27(2H, m), 2.46(1H, d, J=9.5 Hz), 7.54(1H, dd, J=0.9, 1.8 Hz), 7.57(1H, d, J=1.1 Hz), 7.59(1H, br), 7.68(1H, m), 8.57(1H, m)

EXAMPLE 3

2-(N-(2-Thiophenesulfonyl)glycyloxy)-1-(imidazo-[1,2-a]pyridin-6-yl)-N'-methylcyclohexane-carbothioamide

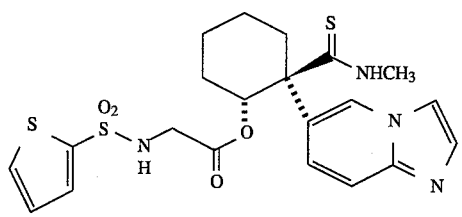

0.3 g of the 2-glycyloxy-1-(imidazo[1,2-a]-pyridin- 6-yl)-N-methylcyclohexane-carbothioamide prepared in the Preparative Example 28 was suspended in 3 ml of dichloromethane, followed by the addition of 0.08 ml of pyridine. The obtained mixture was cooled with ice, followed by the addition of 0.17 g of 2-thiophenesulfonyl chloride. The obtained mixture was stirred for one hour and thereafter at room temperature for 15 minutes, followed by the addition of dilute aqueous ammonia. The resulting mixture was extracted with chloroform. The chloroform phase was dried over anhydrous magnesium sulfate and freed from the solvent by distillation. The residue was purified by silica gel column chromatography (solvent:a 40:1 dichloromethane/methanol mixture) and the obtained oil was crystallized from chloroform/ether to give 0.31 g of the title compound as a white powder (yield:72%).

m.p. (°C.):143–145

NMR (400 MHz, δ, CDCl₃):

1.40(1H, m), 1.52–1.68(3H, m), 1.76(1H, m), 2.21(1H, m), 2.38(1H, m), 2.56(1H, m), 3.07(3H, d, J=4.6 Hz), 3.67(1H, d, J=17.8 Hz), 3.80(1H, d, J=17.8 Hz), 5.37 (1H, br), 5.98 (1H, dd, J=3.5, 9.4 Hz), 7.08(1H, m), 7.21(1H, dd, J=1.8, 9.5 Hz), 7.40(1H, br), 7.50–7.56(2H, m), 7.59(1H, m), 7.64(1H, m), 7.70(1H, br s), 8.56(1H, m)

EXAMPLES 4 to 27

The following compounds were each prepared in a similar manner to that of the Example 3.

EXAMPLE 4

2-(N-(o-Toluenesulfonyl)glycyloxy)-1-(imidazo-[1,2-a]pyridin-6-yl)-N'-methylcyclohexane-carbothioamide

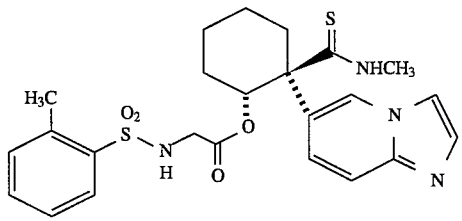

NMR (400 MHz, δ, CDCl₃):

1.30–1.42(1H, m), 1.50–1.80(4H, m), 2.14–2.22 (1H, m), 2.32–2.40(1H, m), 2.42, 2.61 (total 3H, s), 2.54–2.63(1H, m), 3.05, 3.06(total 3H, d, J=4.6 Hz), 3.58, 3.60 (total 1H, d, J=17.4 Hz), 3.68, 3.69 (total 1H, d, J=17.4 Hz), 5.52–5.66(1H, br), 5.92, 5.93(total 1H, dd, J=3.8, 9.3 Hz), 7.13–7.18(1H, m), 7.25–7.87(8H, m), 8.58–8.63(1H, m)

EXAMPLE 5

2-(N-(m-Toluenesulfonyl)glycyloxy)-1-(imidazo[1,2-a]-pyridin-6-yl)-N'-methylcyclohexanecarbothioamide

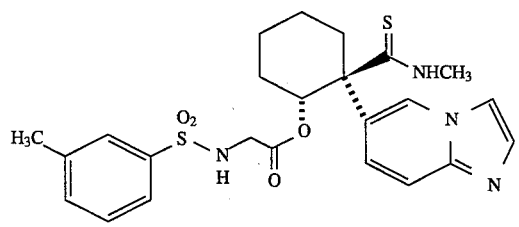

m.p. (°C.): 206–209

NMR (400 MHz, δ, CDCl₃):

1.36(1H, m), 1.52–1.69(3H, m), 1.76(1H, m), 2.18(1H, m), 2.37(1H, m), 2.41(3H, s), 2.58(1H, m), 3.06(3H, d, J=4.6 Hz), 3.61(1H, dd, J=4.6, 17.9 Hz), 3.71(1H, dd, J=5.3, 17.9 Hz), 5.48(1H, br), 5.94(1H, dd, J=3.5, 9.7 Hz), 7.18(1H, dd, J=1.6, 9.5 Hz), 7.36–7.42(2H, m), 7.49(1H, d, J=9.5 Hz), 7.54–7.64(4H, m), 7.72(1H, m), 8.63(1H, m)

EXAMPLE 6

2-(N-(p-Toluenesulfonyl)glycyloxy)-1-(imidazo-[1,2-a]pyridin-6-yl)-N'-methylcyclohexane-carbothioamide

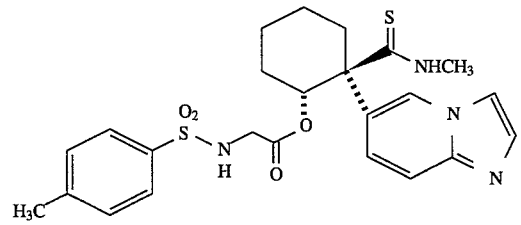

m.p. (°C.): 216–218

NMR (400 MHz, δ, CDCl₃):

1.36(1H, m), 1.50–1.69(3H, m), 1.74(1H, m), 2.16(1H, m), 2.37(1H, m), 2.43(3H, s), 2.58(1H, m), 3.06(3H, d, J=4.8 Hz), 3.60(1H, dd, J=5.1, 17.6 Hz), 3.70(1H, dd, J=5.7, 17.6 Hz), 5.18(1H, br), 5.93(1H, dd, J=3.7, 9.7 Hz), 7.19(1H, dd, J=1.8, 9.5 Hz), 7.28–7.32(2H, m), 7.45(1H, br), 7.54(1H, d, J=9.5 Hz), 7.64(1H, s), 7.65–7.69(2H, m), 7.73(1H, s), 8.63(1H, s)

EXAMPLE 7

2-(N-(2-Methoxybenzenesulfonyl)glycyloxy)-1-(imidazo-[1,2-a]pyridin-6-yl)-N'-methylcyclohexane-carbothioamide

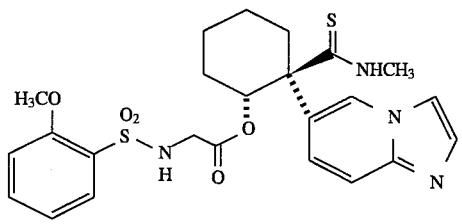

m.p. (°C.): 145–148

NMR (400 MHz, δ, CDCl$_3$):

1.28–1.42(1H, m), 1.46–1.62(3H, m), 1.64–1.76(1H, m), 2.04–2.13(1H, m), 2.13–2.23(1H, m), 2.27–2.36(1H, m), 2.55–2.65(1H, m), 3.04(3H, d, J=4.8 Hz), 3.52(1H, d, J=18.0 Hz), 3.68(1H, d, J=18.0 Hz), 3.98(3H, s), 5.85(br s), 5.89(dd, J=3.4, 8.9 Hz), 6.98–7.04(2H, m), 7.10(dd, J=1.7, 9.7 Hz), 7.284(1H, s), 7.50(1H, d, J=1.3 Hz), 7.51–7.59 (1H, m), 7.64(1H, s), 7.75(1H, dd, J=1.7, 8.1 Hz), 8.20(1H, br s)

EXAMPLE 8

2-(N-(4-Methoxybenzenesulfonyl)glycyloxy)-1-(imidazo-[1,2-a]pyridin-6-yl)-N'-methylcyclohexanecarbothioamide

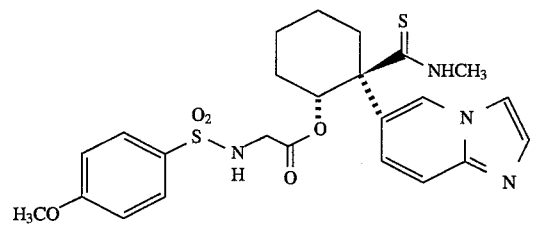

m.p. (°C.): 214–216

NMR (400 MHz, δ, CDCl$_3$):

1.35(1H, m), 1.52–1.82(4H, m), 2.18(1H, m), 2.37(1H, m), 2.60(1H, m), 3.07(3H, d, J=4.8 Hz), 3.59(1H, d, J=17.8 Hz), 3.69 (1H, d, J= 17.8 Hz), 3.86(3H, s), 5.78(1H, dd, J=3.7, 9.7 Hz), 6.94–6.99(2H, m), 7.21(1H, dd, J=1.8, 9.7 Hz), 7.51(1H, d, J=9.7 Hz), 7.57(1H, br), 7.61(1H, d, J= 1.3 Hz 7.70–7.75(3H, m), 8.65(1H, m)

EXAMPLE 9

2-(4-Fluorobenzenesulfonyl)glycyloxy)-1-(imidazo-[1,2-a]pyridin-6-yl)-N'-methylcyclohexane-carbothioamide

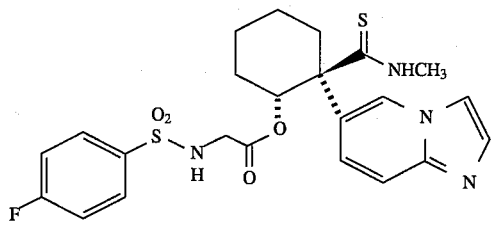

m.p. (°C.): 207–210

NMR (400 MHz, δ, CDCl$_3$):

1.40(1H, m), 1.51–1.80(4H, 2.19(1H, m), 2.37(1H, m), 2.56(1H, m), 3.07(3H, d, J=4.8 Hz), 3.61(1H, d, J=17.1 Hz), 3.72(1H, d, J=17.8 Hz), 5.55(1H, br), 5.96(1H, dd, J=3.5, 9.2 Hz), 7.15–7.21 (2H, m), 7.22(1H, dd, J=1.8, 9.7 Hz), 7.49(1H, d, J=9.7 Hz), 7.55(1H, br), 7.60(1H, d, J=1.3 Hz), 7.70(1H, m), 7.78–7.84(2H, m), 8.58(1H, m)

EXAMPLE 10

2-(N-(4-Chlckobenzenesulfonyl)glycyloxy)-1-(imidazo-[1,2-a]pyridin-6-yl)-N'-methylcyclohexane-carbothioamide

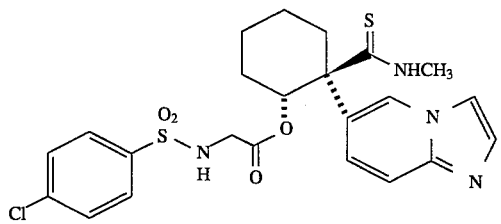

m.p. (°C.): 205–206 (dec.)

NMR (400 MHz, δ, DMSO-d$_6$):

1.21–1.34(1H, m), 1.38–1.49(2H, m), 1.49–1.66(2H, m), 2.08–2.20(2H, m), 2.64–2.74(2H, m), 2.90(3H, s), 3.27(1H, d, J=18.0 Hz), 3.60(1H, d, J=18.0 Hz), 5.95(1H, m), 7.22(1H, dd, J=1.8, 9.5 Hz), 7.30(1H, d, J= 9.5 Hz), 7.55(1H, d, J=1.1 Hz), 7.57–7.65(4H, m), 7.96(1H, d, J=0.7 Hz), 8.21(1H, br s), 8.51(1H, s), 9.46(1H, br s)

EXAMPLE 11

2-(N-(4-Bromobenzenesulfonyl)glycyloxy)-1-(imidazo-[1,2-a]pyridin-6-yl)-N'-methylcyclohexane-carbothioamide

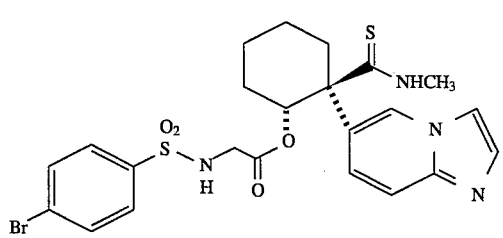

m.p. (°C.): 208–210 (dec.)
NMR (400 MHz, δ, DMSO-$d_6$):
1.21–1.34(1H, m), 1.38–1.49(2H, m), 1.49–1.65(2H, m), 2.07–2.20(2H, m), 2.65–2.74(1H, m), 2.90(3H, d, J=3.8 Hz), 3.28(1H, d, J=18.0 Hz), 3.60(1H, d, J=18.0 Hz), 5.95(1H, br s), 7.22(1H, dd, J=2.0, 9.7 Hz), 7.43(1H, d, J=9.5 Hz), 7.52–7.57(3H, 7.72–7.77(2H, m), 7.96(1H, s), 8.22(1H, s), 8.50(1H, s), 9.46(1H, br s)

EXAMPLE 12

2-(N-(4-Cyanobenzenesulfonyl)glycyloxy)-1-(imidazo-[1,2-a]pyridin-6-yl)-N'-methylcyclohexane-carbothioamide

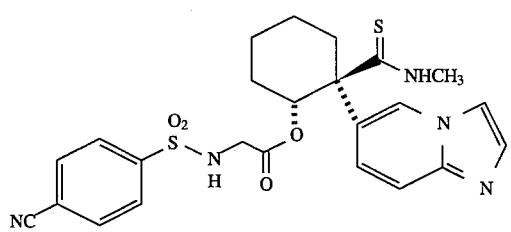

m.p. (°C.): 215–217
NMR (400 MHz, δ, CDCl$_3$):
1.43(1H, m), 1.52–1.78(4H, m), 2.19(1H, m), 2.38(1H, m), 2.54(1H, m), 3.07(3H, d, J=4.6 Hz), 3.67(1H, d, J=17.8 Hz), 3.77(1H, d, J=17.8 Hz), 5.99(1H, dd, J=3.7, 9.3Hz), 7.23–7.30(2H, m), 7.47(1H, br), 7.50(1H, d, J=9.7 Hz), 7.60(1H, d, J=1.3 Hz), 7.69(1H, s), 7.78–7.82(2H, m), 7.89–7.94(2H, m), 8.55(1H, m)

EXAMPLE 13

2-(N-(4-Trifluoromethylbenzenesulfonyl)glycyloxy)-1-(imidazo-[1,2-a]pyridin-6-yl)-N'-methylcyclohexane-carbothioamide

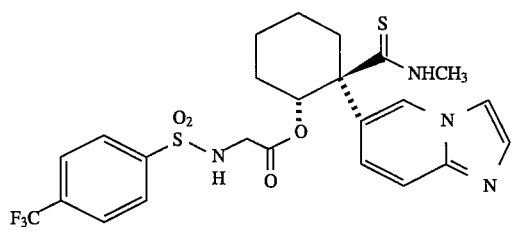

m.p. (°C.): 214–215 (dec.)
NMR (400 MHz, δ, DMSO):
1.20–1.34(1H, m), 1.38–1.48(2H, m), 1.50–1.63(2H, m), 2.06–2.19(2H, m), 2.64–2.73(1H, m), 2.90(3H, d, J=4.0 Hz), 3.33 (1H, d, J=18.1 Hz), 3.65 (1H, d, J=18.1 Hz), 5.95(1H, br s), 7.22(1H, dd, J=1.8, 9.7 Hz), 7.43(1H, d, J=9.7 Hz), 7.55(1H, d, J=1.1 Hz), 7.84(2H, d, J=8.3 Hz), 7.93(2H, d, J=8.3 Hz), 7.96(1H, s), 8.40(1H, br s), 8.50(1H, s), 9.46(1H, br s)

EXAMPLE 14

2-(N-(4-Acetaminobenzenesulfonyl)glycyloxy)-1-(imidazo-[1,2-a]pyridin-6-yl)-N'-methylcyclohexane-carbothioamide

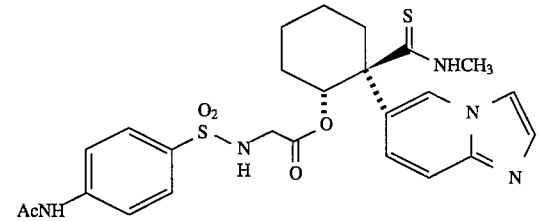

NMR (400 Hz, δ, DMSO-$d_6$):
1.20–1.32(1H, m), 1.35–1.64(4H, m), 2.06(3H, s), 2.02–2.18(2H, m), 2.65–2.70(1H, m), 2.88(3H, d, J=3.5 Hz), 3.19(1H, d, J=18.0 Hz), 3.49(1H, d, J=18.0 Hz), 5.92(1H, bs), 7.18(1H, dd, J=9.5, 2.0 Hz), 7.40(1H, d, J=9.5 Hz), 7.52(1H, d, J=2.0 Hz), 7.53(1H, d, J=9.0 Hz), 7.67(1H, d, J=9.0 Hz), 7.92(1H, m), 7.93(1H, s), 8.49(1H, s), 9.42(1H, bs), 10.23(1H, s)

EXAMPLE 15

2-(N-(2,3-Dichlorobenzenesulfonyl)glycyloxy)-1-(imidazo-[1,2-a]pyridin-6-yl)-N'-methylcyclohexane-carbothioamide

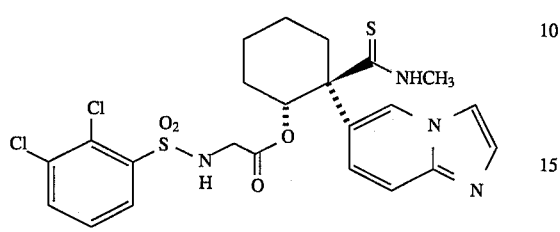

m.p. (°C.): 224–226

NMR (400 MHz, δ, DMSO-$d_6$):

1.28(1H, m), 1.38–1.48(2H, m), 1.50–1.66(2H, m), 2.11(1H, m), 2.69(1H, m), 2.90(3H, d, J=4.4 Hz), 3.41(1H, d, J=18.1 Hz), 3.69(1H, d, J=18.1 Hz), 5.95(1H, br), 7.19(1H, dd, J=1.6, 9.7 Hz), 7.41(1H, d, J=9.7 Hz), 7.48(1H, t, J=8.1 Hz), 7.55(1H, s), 7.69(1H, dd, J=1.5, 8.1 Hz), 7.89(1H, dd, J=1.5, 8.1 Hz), 7.96(1H, s), 8.47(2H, s), 9.46(1H, br)

EXAMPLE 16

2-(N-(4-Acetoxybenzenesulfonyl)glycyloxy)-1-(imidazo-[1,2-a]pyridin-6-yl)-N'-methylcyclohexane-carbothioamide

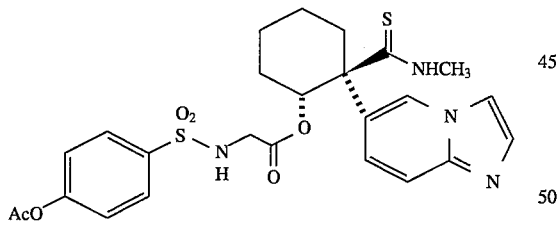

NMR (400 Hz, δ, $CDCl_3$):

1.30–1.43(1H, m), 1.50–1.66(2H, m), 1.67–1.82(2H, m), 2.15–2.23(1H, m), 2.33 (3H, s), 2.34–2.40 (1H, m), 2.54–2.63(1H, m), 3.05 (3H, d, J= 4.5 Hz), 3.62(1H, d, J=18.0 Hz), 3.70 (1H, d, J=18.0 Hz), 5.95(1H, dd, J= 8.0, 3.5 Hz), 7.19(1H, dd, J= 9.5, 2.0 Hz), 7.12–7.34(2H, m), 7.44(1H, d, J=9.5 Hz), 7.56 (H, d, J=1.0 Hz), 7.64–7.72(2H, m), 7.73–7.89(2H, m), 8.59(1H, s)

EXAMPLE 17

2-(N-(4-Methoxythiobenzenesulfonyl)glycyloxy)-1-(imidazo-[1,2-a]pyridin-6-yl)-N'-methylcyclohexane-carbothioamide

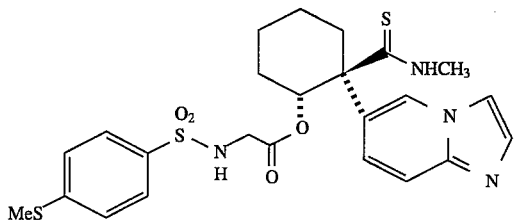

NMR (400 MHz, δ, $CD_3OD$):

1.37–1.48(1H, m), 1.53–1.62(2H, m), 1.72–1.81(2H, m), 2.36–2.51(2H, m), 2.51(3H, s), 2.75–2.82(1H, m), 3.00(3H, s), 3.37(1H, d, J=18.0 Hz), 3.43(1H, d, J=18.0 Hz), 6.27–6.31(1H, m), 7.30–7.34(2H, m), 7.47–7.53(2H, m), 7.79(1H, d, J=9.5 Hz), 7.98(1H, d, J=2.0 Hz), 8.23(1H, br s), 8.24(1H, dd, J=9.5, 1.5 Hz), 8.91(1H, br s)

EXAMPLE 18

2-(N-(4-Nitrobenzenesulfonyl)glycyloxy)-1-(imidazo-[1,2-a]pyridin-6-yl)-N'-methylcyclohexane-carbothioamide

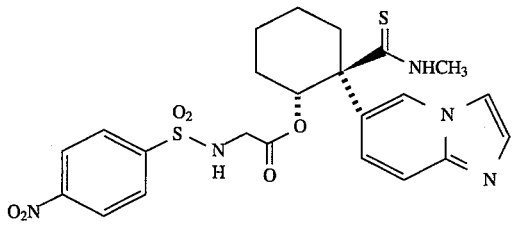

NMR (400 MHz, δ, $CD_3OD$):

1.35–1.46(1H, m), 1.46–1.7(4H, m), 2.26–2.36(2H, m), 2.59–2.67(1H, m), 2.98(3H, s), 3.43(1H, d, J=18.0 Hz), 3.70(1H, d, J=18.0 Hz), 4.87(2H, 6.09(1H, m), 7.40(1H, d, J=9.5 Hz), 7.45(1H, dd, J=9.5, 2.0 Hz), 7.52(1H, d, J=1.0 Hz), 7.83(1H, bs), 7.87–7.91(2H, m), 8.28–8.32(2H, m), 8.55(1H, bs)

EXAMPLE 19

2-(N-(3-Nitrobenezenesulfonyl)glycyloxy)-1-(imidazo-[1,2-a]pyridin-6-yl)-N'-methylcyclohexane-carbothioamide

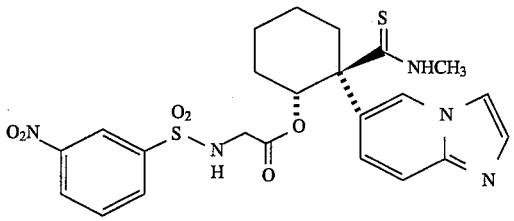

NMR (400 MHz, δ, CDCl₃):

1.40–1.64(4H, m), 1.65–1.76(1H, m), 2.18–2.27 (1H, m), 2.32–2.39(1H, m), 2.50–2.59(1H, m), 3.04(3H, d, J=5.0 Hz), 3.66(1H, d, J=18.0 Hz), 3.86(1H, d, J=18.0 Hz), 6.00(1H, dd, J=8.0, 3.0 Hz), 7.24(1H, dd, J=9.5, 2.0 Hz), 7.29(1H, d, J=9.5 Hz), 7.44(1H, d, J=1.0 Hz), 7.60(1H, s), 7.70(1H, dd, J=8.0, 8.0 Hz), 7.86–7.92(1H, m), 8.10(1H, ddd, J=8.0, 1.5, 1.0 Hz), 8.37(1H, ddd, J=8.0, 2.0, 1.0 Hz), 8.48(1H, bs), 8.51–8.53(1H, m)

EXAMPLE 20

2-(N-(2-Nitrobenzenesulfonyl)glycyloxy)-1-(imidazo-[1,2-a]pyridin-6-yl)-N'-methylcyclohexane-carbothioamide

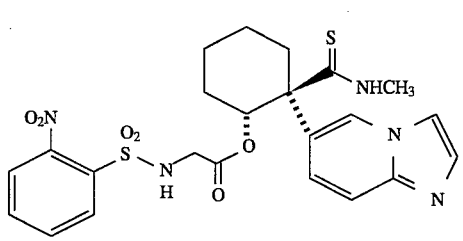

NMR (400 MHz, δ, CD₃OD):

1.34–1.46(1H, m), 1.46–1.76(4H, m), 2.27–2.38(2H, m), 2.60–2.68(1H, m), 2.97(3H, s), 3.57(1H, d, J=18.5 Hz), 3.78(1H, d, J=18.5 H), 4.87(2H, s), 6.10(1H, m), 7.38(1H, d, J=9.5 Hz), 7.44(1H, dd, J=9.5, 2.0 Hz), 7.53(1H, d, J=1.0 Hz), 7.70–7.85(4H, m), 8.51–8.55(1H, m), 8.54(1H, bs)

EXAMPLE 21

2-(N-(2-Fluorobenzenesulfonyl)glycyloxy)-1-(imidazo-[1,2-a]pyridin-6-yl)-N'-methylcyclohexane-carbothioamide

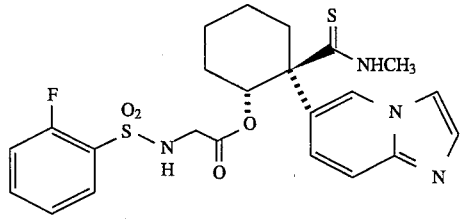

m.p. (°C.): 199–200 (dec.)

NMR (400 MHz, δ, DMSO-d₆):

1.20–1.32(1H, m), 1.37–1.48(2H, m), 1.48–1.66(2H, m), 2.07–2.20 (2H, m), 2.65–2.75 (1H, m), 2.89(3H, d, J=4.2 Hz), 3.40 (1H, d, J= 18.3 Hz), 3.76(1H, d, J=18.3 Hz), 5.94(1H, br s), 7.20(1H, dd, J=1.6, 9.5 Hz), 7.28–7.46(3H, m), 7.55(1H, s), 7.59(1H, dt, J=1.5, 7.7 Hz), 7.63–7.70(1H, m), 7.96(1H, s), 8.38(1H, br s), 8.56(1H, s), 9.47(1H, br s)

EXAMPLE 22

2-(N-(2,5-Dichlorobenzenesulfonyl)glycyloxy)-1-(imidazo-[1,2-a]pyridin-6-yl)-N'-methylcyclohexane-carbothioamide

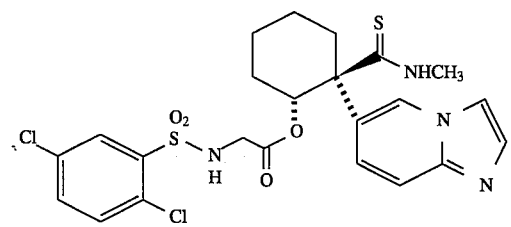

m.p. (°C.): 200–202 (dec.)

NMR (400 MHz, δ, CDCl₃):

1.34–1.46(1H, m), 1.46–1.64(3H, m), 1.68–1.79(1H, m), 1.98(1H, br), 2.17–2.26(1H, m), 2.30–2.38(1H, m), 2.55–2.64(1H, m), 3.06(3H, d, J=4.6 Hz), 3.65(1H, d, J=17.9 Hz), 3.77(1H, J=17.9 Hz), 5.97(1H, dd, J=3.1, 5.97 Hz), 7.16(1H, dd, J=1.8, 9.7 Hz), 7.30(1H, d, J=9.5 Hz), 7.43–7.50(3H, m), 7.62(1H, s), 7.95(1H, d, J=2.2 Hz), 8.07(1H, br), 8.54(1H, s)

EXAMPLE 23

2-(N-(4-Chloro-3-nitrobenzenesulfonyl)glycyloxy)-1-(imidazo-[1,2-a]pyridin-6-yl)-N'-methylcyclohexane-carbothioamide

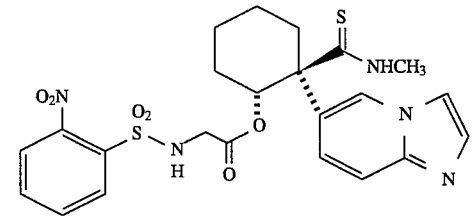

NMR (400 MHz, δ, CDCl₃):

1.40–1.55(2H, m), 1.55–1.65(2H, m), 1.67–1.77(1H, m), 2.18–2.27(1H, m), 2.31–2.39(1H, m), 2.50–2.58(1H, m), 3.04(3H, d, J=5.0 Hz), 3.65(1H, d, J=18.0 Hz), 3.82(1H, d, J=18.0 Hz), 6.03(1H, dd, J=8.0, 3.0 Hz), 7.26(2H, m), 7.41(1H, d, J=1.0 Hz), 7.58(1H, s), 7.67(1H, d, J=8.0 Hz), 7.88(1H, bs), 7.89(1H, dd, J=8.0, 2.0 Hz), 8.17(1H, d, J=2.0 Hz), 8.46(1H, s)

EXAMPLE 24

2-(N-(2-Methylpyrazol-3-ylsulfonyl)glycyloxy)-1-(imidazo-[1,2-a]pyridin-6-yl)-N'-methylcyclohexane-carbothioamide

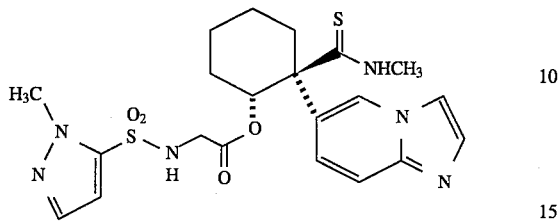

m.p. (°C.): 193–194

NMR (400 MHz, δ, CDCl$_3$):

1.43(1H, m), 1.50–1.79(4H, m), 2.21(1H, m), 2.36(1H, m), 2.54(1H, m), 3.06(3H, d, J=4.6 Hz), 3.64(1H, d, J=17.9 Hz), 3.77(1H, d, J=17.9 Hz), 4.07(3H, s), 6.01(1H, dd, J=3.5, 8.9 Hz), 6.66(1H, d, J=2.2 Hz), 7.25(1H, dd, J=1.8, 9.5 Hz), 7.27(1H, d, J=2.2 Hz), 7.44–7.54(2H, m), 7.58(1H, d, J=1.1 Hz), 7.67(1H, m), 8.52(1H, m)

EXAMPLE 25

2-(N-(2-Naphthalenesulfonyl)glycyloxy)-1-(imidazo-[1,2-a]pyridin-6-yl)-N'-methylcyclohexane-carbothioamide

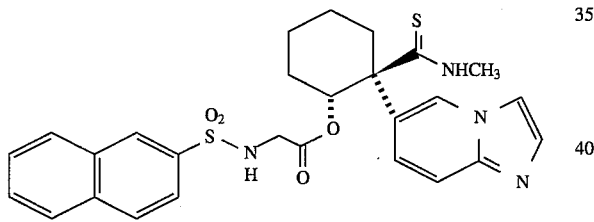

m.p. (°C.): 212–214

NMR (400 MHz, δ, CDCl$_3$):

1.33(1H, m), 1.48–1.70(4H, m), 2.08(1H, m), 2.35(1H, m), 2.55(1H, m), 3.03(3H, d, J=4.8 Hz), 3.64(1H, dd, J=3.7, 17.8 Hz), 3.75(1H, dd, J=5.3, 17.8 Hz), 5.38(1H, br), 5.91(1H, dd, J=3.7, 9.5 Hz), 7.17(1H, dd, J=1.8, 9.7 Hz), 7.43(1H, br), 7.52(1H, d, J=9.7 Hz), 7.59–7.65(2H, m), 7.67(1H, dd, J=1.5, 7.0 Hz), 7.72(1H, s), 7.76(1H, dd, J=1.8, 8.6 Hz), 7.90–7.98(3H, m), 8.37(1H, d, J=1.8 Hz), 8.61(1H, s)

EXAMPLE 26

2-(N-(1-Naphthalenesulfonyl)glycyloxy)-1-(imidazo-[1,2-a]pyridin-6-yl)-N'-methylcyclohexane-carbothioamide

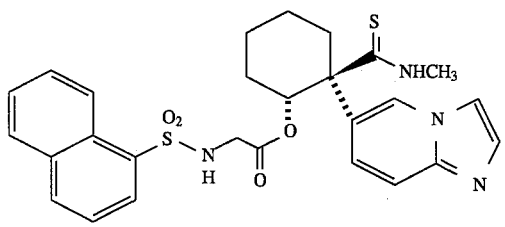

m.p. (°C.): 158–160

NMR (400 MHz, δ, DMSO-d$_6$):

1.20–1.27(1H, m), 1.34–1.40(2H, m), 1.46–1.56(2H, m), 2.00–2.08(2H, m), 2.61–2.68(1H, m), 2.89(1H, d, J=4.0 Hz), 3.29 (1H, d, J=18.0 Hz), 3.58 (1H, d, J=18.0 Hz), 5.90(1H, br s), 7.16(1H, dd, J=9.5, 2.0 Hz), 7.41(1H, d, J=9.5 Hz), 7.53–7.57(2H, m), 7.63–7.70(2H, m), 7.85–7.89(1H, m), 7.96(1H, s), 8.06–8.09 (1H, m), 8.19(1H, d, J=8.0 Hz), 8.44–8.49(2H, m), 8.53–8.56(1H, m), 9.44(1H, br s)

EXAMPLE 27

2-(N-Benzylsulfonylglycyloxy)1-imidazo-[1,2-a]pyridin-6-yl)-N'-methylcyclohexane-carbothioamide

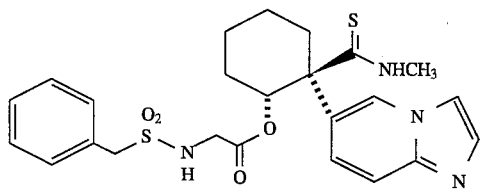

NMR (400 MHz, δ, CDCl$_3$):

1.25–1.38(1H, m), 1.50–1.67(2H, m), 1.77–1.84(1H, m), 1.9–2.1(1H, bs), 2.18–2.23(1H, m), 2.31–2.40(1H, m), 2.56–2.63(1H, m), 3.01(3H, d, J=4.5 Hz), 3.46(1H, d, J=18.0 Hz), 3.52(1H, d, J=18.0 Hz), 4.18(1H, d, J=14.0 Hz), 4.23(1H, d, J=14.0 Hz), 5.80(1H, bs), 5.92(1H, dd, J=9.0, 3.5 Hz), 7.13(1H, dd, J=10.0, 2.0 Hz), 7.33(1H, d, J=10.0 Hz), 7.35(5H, m), 7.46(1H, d, J=1.0 Hz), 7.62(1H, s), 7.95(1H, bs), 8.55(1H, s)

EXAMPLE 28

2-(N-Benzenesulfonylglycyloxy)-1-(4-methylimidazol-1-yl)-N'-methylcyclohexanecarbothioamide

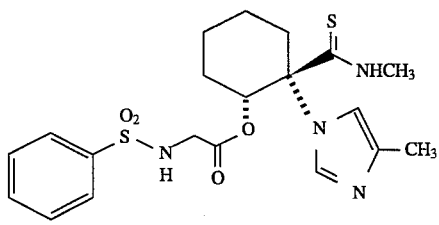

0.3 g of the 2-glycyloxy-N-methyl-1-(4-methylimidazol-1-yl)cyclohexanecarbothloamide prepared in the Preparative Example 29 was dissolved in 5 ml of dichloromethane, followed by the addition of 0.13 ml of trimethylamine. The obtained mixture was cooled with ice, followed by the dropwise addition of a solution of 0.12 ml of benzenesulfonyl chloride in 2 ml of dichloromethane. After one hour, 5 ml of concentrated aqueous ammonia was added to the resulting mixture, followed by the addition of water. The obtained mixture was extracted with chloroform. The organic phase was dried over anhydrous sodium sulfate and freed from the solvent by distillation. The residue was purified by silica gel column chromatography (solvent: a 40:1 dichloromethane/methanol mixture). The obtained oil was crystallized from ethyl acetate/n-hexane to give 0.24 g of the title compound as a white powder (yield: 55%).

m.p. (°C.): 201–202

NMR (400 MHz, δ, CDCl$_3$):

1.28(1H, m), 1.46(1H, m), 1.53–1.75(3H, m), 1.90(1H, m), 2.29(3H, d, J=0.7 Hz), 2.36(1H, m), 2.73(1H, m), 3.00(3H, d, J=4.8 Hz), 3.73(1H, J=4.0, 18.1 Hz), 3.83(1H, dd, J=5.1, 18.1 Hz), 5.22(1H, br), 5.95(1H, dd, J=3.8, 11.9 Hz), 6.77(1H, br), 6.93(1H, s), 7.51–7.56(2H, m), 7.60(1H, m), 7.78(1H, s), 7.82–7.87(2H, m)

EXAMPLE 29

2-(N-Benzenasulfonyloxy)-1-(imidazo-[1,2-a]pyridin-6-yl)-N'-methylcyclohexane-carbothioamide

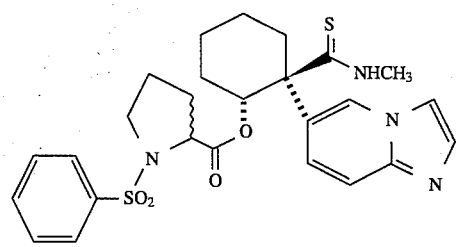

The title compound was prepared by use of the compound prepared in the Preparative Example 30 as the starting compound in a similar manner to that of the Example 3.

NMR (400 MHz, δ, CDCl$_3$):

1.22(1H, m), 1.53–2.05(8H, m), 2.10, 2.30(total 1H, m), 2.41–2.52(1H, m), 2.63–2.78(1H, m), 3.02, 3.21(total 1H, m), 3.08, 3.09(total 3H, d, J=4.8 Hz), 3.29, 3.56(total 1H, m), 4.19, 4.24(total 1H, dd, δ4.19 peak, J=3.3, 8.8 Hz), δ4.24 peak, J=2.6, 8.2 Hz), 5.8, 5.91(total 1H, dd, J=3.7, 11.0 Hz), 7.17, 7.20(total 1H, dd, J=1.8, 9.7 Hz), 7.39, 7.73(total 1H, br), 7.51–7.68(4H, m), 7.76–8.04(3H, m), 8.87, 9.14(total 1H, s)

EXAMPLE 30

2-(N-Benzenesulfonyl-β-benzylaspartyloxy)-1-(imidazo-[1,2-a]pyridin-6-yl)-N'-methylcyclohexane-carbothioamide

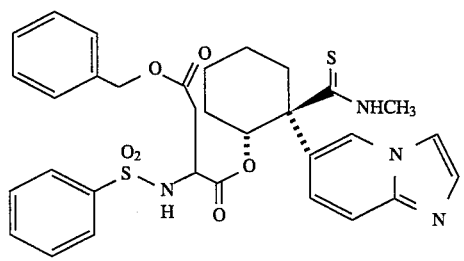

The title compound was prepared by the use of the compound prepared in the Preparative Example 32 as the starting compound in a similar manner to that of the Example 3.

m.p. (°C.): 109–114

NMR (400 MHz, δ, CDCl$_3$):

1.33(1H, m), 1.48–1.65(3H, m), 1.78(1H, m), 2.22(1H, m), 2.38(1H, m), 2.58(1H, dd, J=5.3, 17.0 Hz), 2.65(1H, m), 2.78(1H, dd, J=4.8, 17.0 Hz), 3.08(3H, d, J=4.8 Hz), 4.21(1H, br), 4.92(1H, d, J=12.3 Hz), 4.99(1H, d, J=12.3 Hz), 5.90(1H, dd, J=3.1, 9.0 Hz), 6.14(1H, br), 7.12(1H, ddd, J=2.0, 4.8, 9.6 Hz), 7.22–7.26(2H, m), 7.30–7.37(3H, m), 7.40(1H, m), 7.43–7.49(2H, m), 7.53–7.60(2H, m), 7.71–7.79(3H, m), 7.82(1H, br), 8.74(1H, br s)

EXAMPLE 31

2-(N-Benzenasulfonylalanyloxy)-1-(imidazo-[1,2-a]pyridin-6-yl)-N'-methylcyclohexane-carbothioamide (an about 3:1 mixture)

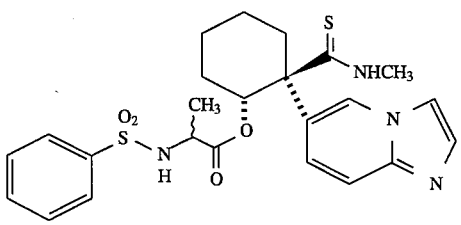

0.73 g of the 2-(N-t-butoxycarbonylalanyloxy)-1(imidazo[1,2-a]pyridin-6-yl)-N'-methylcyclohexanecarbothioamide prepared in the Preparative Example 17 was dissolved in 10 ml of chloroform, followed by the addition of 10 ml of 9% hydrogen chloride/ethyl acetate. The obtained mixture was stirred at room temperature for 12 hours and freed from the solvent by distillation to give a white amorphous substance. This amorphous substance was dissolved in 4 ml of pyridine, followed by the addition of 0.41 ml of benzenesulfonyl chloride. The obtained mixture was stirred at room temperature for 2 hours, followed by the addition of a saturated aqueous solution of sodium hydrogencarbonate. The resulting mixture was extracted with chloroform. The chloroform phase was dried over anhydrous magnesium sulfate and freed from the solvent by distillation. The residue was purified by silica gel column chromatography (solvent: a 30:1 dichloromethane/methanol mixture) and crystallized from dichloromethane/ether to give 0.33 g of the title compound as a white powder (yield: 41%).

NMR (400 MHz, δ, CDCl₃):

0.89, 1.18(total 3H, d, J=7.1 Hz), 1.29–1.84(5H, m), 2.04–2.41(2H, m), 2.53–2.65(1H, m), 3.05, 3.07(total 3H, d, J=4.8 Hz), 3.82–3.93(1H, m), 5.53–5.70(1H, m), 5.88–5.94(1H, m), 7.17, 7.19(total 1H, dd, J=1.8, 9.5 Hz), 7.43–7.52(3H, m), 7.54–7.82(6H, m), 8.44, 8.73(total 1H, s)

EXAMPLE 32

2-(N-(1-Naphthalenesulfonyl)-β-alanyloxy)-1-(imidazo-[1,2-a]pyridin-6-yl)-N'-methylcyclohexane-carbothioamide

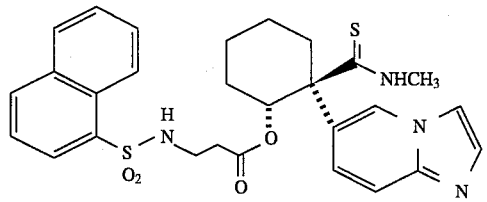

The title compound was prepared in the same manner as that of the Example 31 except that the compound prepared in the Preparative Example 15 was used as the starting compound and that 1-naphthalenesulfonyl chloride was used instead of the benzenesulfonyl chloride.

m.p. (°C.): 136–141

NMR (400 MHz, δ, CDCl₃):

1.41(1H, m), 1.53–1.71(4H, m), 2.13(1H, m), 2.29–2.48(3H, m), 2.55(1H, m), 3.08(2H, m), 3.09(3H, d, J=4.6 Hz), 5.46(1H, t, J=6.6 Hz), 6.01(1H, dd, J=3.1, 9.0 Hz), 7.24(1H, dd, J=1.8, 9.5 Hz), 7.46(1H, br), 7.50–7.56(2H, m), 7.59–7.72(4H, m), 7.95(1H, dd, J=0.9, 8.2 Hz), 8.08(1H, d, J=8.2 Hz), 8.20(1H, dd, J=1.3, 7.3 Hz), 8.50(1H, m), 8.58(1H, d, J=8.8 Hz)

EXAMPLE 33

2-(N-Benzenasulfonylphenylalanyloxy-1-(imidazo-[1,2-a]pyridin-6-yl)-N'-methylcyclohexane-carbothioamide (L-form)

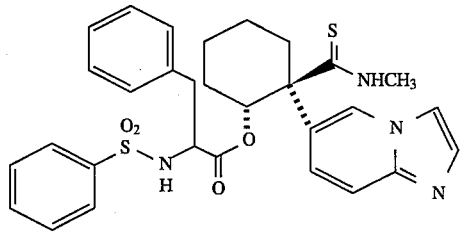

1.88 g of the 2-(N-t-butoxycarbonylphenyl-alanyloxy)-1-(imidazo[1,2-a]pyridin-6-yl)-N'-methylcyclohexanecarbothioamide prepared in the Preparative Example 18 was dissolved in 10 ml of dichloromethane, followed by the addition of 10 ml of trifluoroacetic acid. The obtained mixture was stirred under cooling with ice for 30 minutes, followed by the addition of ice-water. The resulting mixture was alkalinized with sodium carbonate and extracted with chloroform. The chloroform phase was dried over anhydrous magnesium sulfate and freed from the solvent by distillation to give a pale-yellow amorphous substance. This amorphous substance was dissolved in 15 ml of dichloromethane, followed by the addition of 0.54 ml of triethylamine. The obtained mixture was cooled to −30°C., followed by the dropwise addition of a solution of 0.5 ml of benzenesulfonyl chloride in 2 ml of dichloromethane. The resulting mixture was gradually brought to 0° C. and stirred at that temperature for 7 hours, followed by the addition of dilute aqueous ammonia. The resulting mixture was extracted with chloroform. The chloroform phase was dried over anhydrous magnesium sulfate and distilled to remove the solvent. The residue was purified by silica gel column chromatography (solvent: dichloromethane/methanol (50:1 to 40:1)) to give 0.06 g (3%) of a lower-polarity diastereomer (L-form) as a white powder and 0.10 g (55%) of a higher-polarity one (M-form) as a white powder.

m.p. (°C.): 139–144

NMR (400 MHz, δ, CDCl₃):

1.28(1H, m), 1.56–1.72(4H, m), 2.00(1H, m), 2.39(1H, m), 2.60–2.82(3H, m), 3.04(3H, d, J=4.8 Hz), 4.07(1H, m), 4.92(1H, d, J=9.2 Hz), 5.84(1H, dd, J=3.5, 9.3 Hz), 6.84–6.89(2H, m), 7.13–7.22(4H, m), 7.39–7.48(3H, m), 7.51–7.66(5H, m), 7.71(1H, s), 8.58(1H, m)

EXAMPLE 34

2-(N-(Benzenesulfonylphenylalanyloxy-1-(imidazo-[1,2-a]pyridin-6-yl)-N'-methylcyclohexane-carbothioamide (M-form)

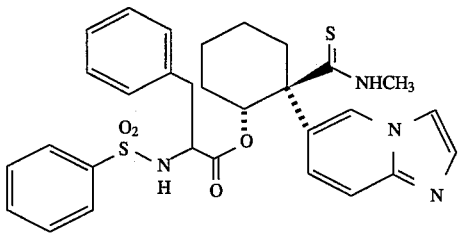

The title compound was prepared in a similar manner to that of the Example 33.

m.p. (°C.): 202–205

NMR (400 MHz, δ, CDCl₃):

1.25(1H, m), 1.53–1.89(4H, m), 2.24(1H, m), 2.39(1H, m), 2.63(1H, m), 2.71(1H, dd, J=8.8, 15.2 Hz), 3.01 (H, dd, J=6.4, 15.2 Hz), 3.02(3H, d, J=4.8 Hz), 4.04 (1H, m), 4.74(1H, m), 5.86(1H, dd, J=4.0, 10.6 Hz), 6.86–6.91(2H, m), 7.12–7.23(4H, m), 7.30(1H, m), 7.38–7.44(2H, m), 7.52–7.62(4H, m), 7.64(1H, d, J=1.1 Hz), 7.83(1H, s), 8.83(1H, m)

EXAMPLE 35

2-(N-(N'-Benzenesulfonylglycyl)glycyloxy)-1-(imidazo-[1,2-a]pyridin-6-yl)-N''-methylcyclohexane-carbothioamide

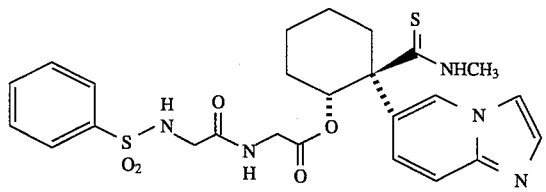

0.56 g of the 2-(N-(N'-t-butoxycarbonyiglycyl)-glycyloxy)- 1-(imidazo[1,2-a]pyridin-6-yl)-N''-methylcyclohexanecarbothioamide prepared in the Preparative Example 35 was dissolved in 5 ml of dichloromethane, followed by the addition of 5 ml of trifluoroacetic acid. The obtained mixture was stirred under cooling with ice for one hour, followed by the addition of ice-water. The resulting mixture was alkalinized with sodium carbonate and extracted with chloroform/methanol. The organic phase was dried over anhydrous magnesium sulfate and freed from the solvent by distillation to give a pale-yellow amorphous substance. This amorphous substance was suspended in 4 ml of dichloromethane, followed by the addition of 0.97 ml of pyridine. The obtained mixture was cooled with ice, followed by the dropwise addition of a solution of 0.15 ml of benzenesulfonyl chloride in 1 ml of dichloromethane. After one hour, dilute aqueous ammonia was added to the resulting mixture, followed by the extraction with chloroform. The chloroform phase was dried over anhydrous magnesium sulfate and distilled to remove the solvent. The residue was purified by silica gel column chromatography (solvent:a 30:1 dichloromethane/methanol mixture). The obtained oil was crystallized from dichloromethane/ether and recrystallized from ethanol/water to give 0.19 g of the title compound as a white powder.

m.p. (°C.): 140–142

NMR (400 MHz, δ, CDCl₃):

1.25(1H, m), 1.50–1.72(3H, m), 1.88(1H, m), 2.23–2.39(2H, m), 2.72(1H, m), 3.10(3H, d, J=4.7 Hz), 3.48(2H, br), 3.82(1H, dd, J=5.3, 17.9 Hz), 4.09(1H, dd, J=6.2, 17.9 Hz), 5.92(1{t, dd, J=3.3, 9.3 Hz), 6.13(1H, br), 7.06(1H, t, J=6.8 Hz), 7.18(1H, dd, J=1.5, 9.7 Hz), 7.45–7.64(7H, m), 7.69–7.76 (2H, m), 8.56(1H, m)

EXAMPLE 36

2-(N'-Benzenesulfonylglycyl)sarcosyloxy-1-(imidazo-[1,2-a]pyridin-6-yl)-N''-methylcyclohexane-carbothioamide

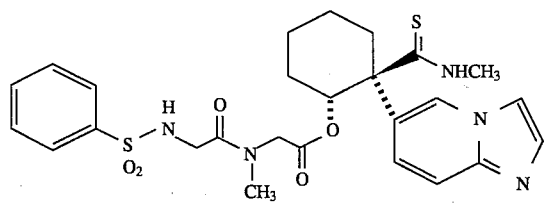

b 0.68g of the 2-(N-(N'-t-butoxycarbonylglycyl)sarcosyloxy)- 1-(imidazo[1,2-a]pyridin-6-yl)-N''-methylcyclohexanecarbothioamide prepared in the Preparative Example 36 was dissolved in 10 ml of chloroform, followed by the addition of 30 ml of 7% hydrogen chloride/ethyl acetate. The obtained mixture was stirred at room temperature for 3.5 hours, followed by the addition of ether. The obtained mixture was filtered to recover an insoluble matter. A pale-yellow powder was obtained.

This powder was suspended in 4 ml of dichloromethane, followed by the addition of 0.6 ml of triethylamine. The obtained mixture was cooled to −15°C., followed by the dropwise addition of a solution of 0.18 ml of benzenesulfonyl chloride in 1 ml of dichloromethane. The obtained mixture was stirred for 15 minutes, followed by the addition of dilute aqueous ammonia. The resulting mixture was extracted with chloroform. The chloroform phase was dried over anhydrous magnesium sulfate and distilled to remove the solvent. The residue was purified by silica gel column chromatography (solvent:a 30:1 dichloromethane/methanol mixture) and crystallized from dichloromethane/ether to give 0.53 g of the title compound as a white powder (overall yield: 73%).

NMR (400 MHz, δ, CDCl₃):

1.38–1.86(5H, m), 2.23–2.36(2H, m), 2.48–2.59(1H, m), 2.64, 2.69(total 3H, s), 3.09(3H, d, J=4.6 Hz), 3.60, 3.66(total 1H, d, J=16.1 Hz), 3.62, 3.71(total 1H, d, J=16.1 Hz), 3.75, 3.88(total 1H, d, J=16.8 Hz), 3.81, 3.94(total 1H, d, J=16.8 Hz), 5.60, 5.76(total 1H, br), 6.07, 6.19(total 1H, dd, J=3.1, 8.1 Hz), 7.21–7.26(1H, m), 7.40–7.62(5H, m), 7.65, 7.69(total 1H, s), 7.77–7.90(3H, m), 8.29, 8.38(total 1H, s)

EXAMPLE 37

2-(N-(Benzenesulfonylglycyloxy)-1-(imidazo-
[1,2-a]pyridin-6-yl)-N'-ethylcyclohexane-
carbothioamide

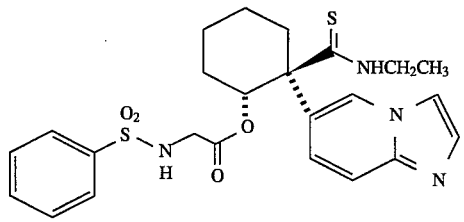

0.48 g of the 2-(N-t-butoxycarbonylglycyloxy)-N'-ethyl-1-(imidazo[1,2-a]pyridin-6-yl)cyclohexanecarbothioamide prepared in the Preparative Example 11 was dissolved in 5 ml of dichloromethane, followed by the addition of 5 ml of trifluoroacetic acid. The obtained mixture was cooled with ice for 30 minutes, followed by the addition of ice-water. The resulting mixture was alkalinized with sodium carbonate and extracted with chloroform. The chloroform phase was dried over anhydrous magnesium sulfate and freed from the solvent by distillation to give a pale-yellow amorphous substance. This amorphous substance was suspended in 5 ml of dichloromethane, followed by the addition of 0.15 ml of triethylamine. The obtained mixture was cooled to −30°C., followed by the dropwise addition of a solution of 0.14 ml of benzenesulfonyl chloride in 1 ml of dichloromethane. The resulting mixture was stirred for one hour, followed by the addition of dilute aqueous ammonia. The resulting mixture was extracted with chloroform. The chloroform phase was dried over anhydrous magnesium sulfate and distilled to remove the solvent. The residue was crystallized from dichloromethane/ether to give 0.26 g of the title compound as a white powder (overall yield: 52%).

m.p. (°C.): 206–208

NMR (400 MHz, δ, CDCl$_3$):

1.07(3H, t, J=7.3 Hz), 1.38(1H, m), 1.46–1.80(4H, m), 2.18(1H, m), 2.35(1H, m), 2.55(1H, m), 3.47–3.71(3H, m), 3.73(1H, d, J=17.8 Hz), 5.32(1H, br), 5.96(1H, dd, J=3.5, 9.2 Hz), 7.18(1H, br), 7.21(1H, dd, J=1.8, 9.5 Hz), 7.47–7.62(4H, m), 7.63(1H, m), 7.71(1H, m), 7.76–7.82(2H, m), 8.57(1H, m)

EXAMPLES 38 TO 46

The following compounds were each prepared in a similar manner to that of the Example 37.

EXAMPLE 38

2-(N-Benzenesulfonylglycyloxy)-1-(2-methylimidazo-
[1,2-a]pyridin-6-yl)-N'-methylcyclohexane-
carbothioamide

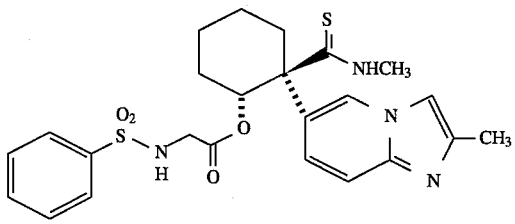

m.p. (°C.): 205–207

NMR (400 MHz, δ, CDCl$_3$):

1.36(1H, m), 1.49–1.77(4H, m), 2.15(1H, m), 2.34(1H, m), 2.44(3H, d, J=0.5 Hz), 2.54(1H, m), 3.04(3H, d, J=4.6 Hz), 3.60(1H, d, J=17.9 Hz), 3.72(1H, d, J=17.9 Hz), 5.33(1H, br), 5.94(1H, dd, J=3.7, 9.5 Hz), 7.13(1H, dd, J=1.8, 9.5 Hz), 7.39(1H, d, J=9.5 Hz), 7.43–7.54(4H, m), 7.59(1H, m), 7.77–7.82(2H, m), 8.49(1H, m)

EXAMPLE 39

2-(N-(Benzenesulfonylglycyloxy)-1(2-trifluoromethyl-
imidazo-[1,2-a]pyridin-6-yl)-N'-methylcyclohexane-
carbothioamide m.p. (°C.): 223–224

NMR (400 MHz, δ, CDCl$_3$):

1.32(1H, m), 1.46–1.70(3H, m), 1.78(1H, m), 2.19(1H, m), 2.40(1H, m), 2.60 (1H, m), 3.08(3H, d, J=4.6 Hz), 3.63 (1H, dd, J=5.8, 17.9 Hz), 3.75 (1H, dd, J=6.0, 17.9 Hz), 5.05(1H, dd, J=5.8, 6.0 Hz), 5.95(1H, dd, J=3.7, 9.5 Hz), 7.35 (1H, dd, J=1.8, 9.9 Hz), 7.45(1H, br), 7.49–7.64(4H, m), 7.76–7.71(2H, m), 8.02(1H, s), 8.67(1H, s)

EXAMPLE 40

2-(N-Naphthalenesulfonylglycyloxy)-1-(imidazo-
[1,2-a]pyridin-6-yl)-N'-ethylcyclohexane-
carbothioamide

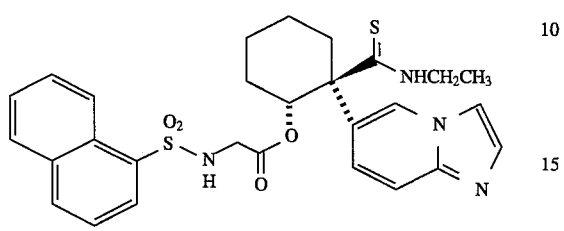

NMR (400 MHz, δ, CDCl₃):
0.97(3H, t, J=7.0 Hz), 1.18–1.28(1H, m), 1.32–1.40(2H, m), 1.44–1.56(2H, m), 1.98–2.14(2H, m), 2.62–2.70(1H, m), 3.24–3.50(2H, m), 3.54–3.60(2H, m), 5.88(1H, m), 7.17(1H, dd, J=10.0, 2.0 Hz), 7.41(1H, d, J=10.0 Hz), 7.53–7.57(2H, m), 7.63–7.69(2H, m), 7.86(1H, dd, J=7.5–1.0 Hz), 7.96(1H, s), 8.06–8.08(1H, m), 8.19(1H, d, J=8.0 Hz), 8.44–8.47(2H, m), 8.54(1H, m), 9.42(1H, m)

EXAMPLE 41

2-(N-Naphthalenesulfonylglycyloxy-1-(2-
methylimidazo-[1,2-a]pyridin-6-yl)-N'-methyl-
cyclohexanecarbothioamide

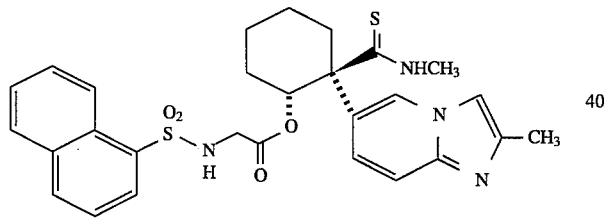

NMR (400 MHz, δ, DMSO-d₆):
1.17–1.26(1H, m), 1.32–1.39(2H, m), 1.44–1.54(2H, m), 1.96–2.10(2H, m), 2.31(3H, s), 2.60–2.68(1H, m), 2.88(3H, d, J=3.5 Hz), 3.27(1H, d, J=18.0 Hz), 3.56(1H, d, J=18.0 Hz), 5.89(1H, m), 7.10(1H, dd, J=10.0, 2.0 Hz), 7.26(1H, d, J=10.0 Hz), 7.55 (1H, dd, J=8.0, 7.5 Hz), 7.63–7.70(3H, m), 7.89(1H, dd, J=7.5, 1.0 Hz), 8.06–8.08(1H, m), 8.19(1H, d, J=8.0 Hz), 8.32(1H, s), 8.35–8.45(1H, bs), 8.54–8.56(1H, m), 9.42(1H, bs)

EXAMPLE 42

2-(N-(8-Quinolinesulfonyl)glycyloxy)-1-(imidazo-
[1,2-a]pyridin-6-yl)-N'-methylcyclohexane-
carbothioamide

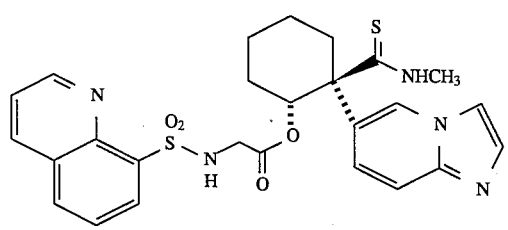

m.p. (°C.): 149–152
NMR (400 MHz, δ, CDCl₃):
1.28(1H, m), 1.52–1.73(3H, m), 1.82(1H, m), 2.14(1H, m), 2.41(1H, m), 2.63(1H, m), 3.08(3H, d, J=4.5 Hz), 3.63–3.77(2H, m), 5.80(1H, dd, J=3.8, 10.4 Hz), 6.86(1H, t, J=6.2 Hz), 7.14(1H, dd, J=1.8, 9.5 Hz), 7.53(1H, br), 7.54(1H, d, J=9.5 Hz), 7.59(1H, dd, J=4.4, 8.4 Hz), 7.63(1H, m), 7.66(1H, m), 7.83(1H, s), 8.08(1H, dd, J=1.5, 8.4 Hz), 8.28–8.35(2H, m), 8.83(1H, s), 9.01(1H, dd, J=1.5, 4.4 Hz)

EXAMPLE 43

2-(N-Benzenesulfonylamino)isobutyryloxy)-1-(imidazo-
[1,2-a]pyridin-6-yl)-N'-methylcyclohexane-
carbothioamide

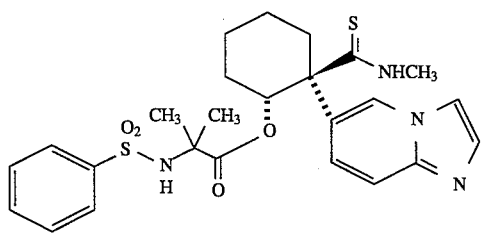

m.p. (°C.): 211–214
NMR (400 MHz, δ, CDCl₃):
1.23(3H, s), 1.24(3H, s), 1.28(1H, m), 1.52–1.77(3H, m), 1.98(1H, m), 2.31(1H, m), 2.39(1H, m), 2.70(1H, m), 3.05(3H, d, J=4.8 Hz), 5.08(1H, s), 5.96(1H, dd, J=3.7, 9.9 Hz), 7.16(1H, dd, J= 1.8, 9.7 Hz), 7.36 (1H, br), 7.47–7.53(2H, m), 7.57(1H, m), 7.61(1H, d, J= 9.7 Hz), 7.64 (1H, d, J=1.3 Hz), 7.81–7.88(2H, m), 7.89(1H, s), 8.83(1H, m)

EXAMPLE 44

2-(N-Benzenesulfonylseryloxy)-1-(imidazo-[1,2-a]pyridin-6-yl)-N'-methylcyclohexane-carbothioamide

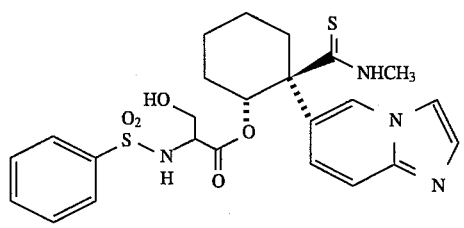

m.p. (°C.): 203–205 (dec.)

NMR (400 MHz, δ, CDCl₃):

1.45–1.78(4H, m), 1.85(1H, m), 2.22(1H, m), 2.40(1H, m), 2.58(1H, m), 3.07(3H, d, J=4.8 Hz), 3.50 (1H, dd, J=4.0, 11.5 Hz), 3.89(1H, m), 3.95(1H, dd, J=2.2, 11.5 Hz), 5.55(1H, br), 6.00 (1H, dd, J=3.8, 11.2 Hz), 7.19(1H, dd, J=1.6, 9.5 Hz), 7.48–7.56(3H, m), 7.58–7.65(3H, m), 7.82–7.86(2H, m), 7.93(1H, s), 8.98(1H, br)

EXAMPLE 45

2-(N-Benzenesulfonylvalyloxy)-1-(imidazo-[1,2-a]pyridin-6-yl)-N'-methylcyclohexane-carbothioamide (L-form)

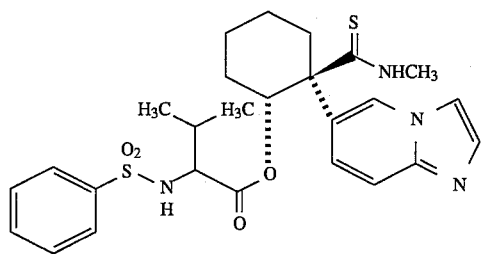

m.p. (°C.): 207–208

NMR (400 MHz, δ, CDCl₃):

0.20(3H, br d, J=6.8 Hz), 0.70(3H, d, J=6.8 Hz), 1.20–1.54(6H, m), 2.20(1H, m), 2.26(1H, m), 2.50(1H, m), 3.07(3H, d, J=4.8 Hz), 3.57(1H, dd, J=4.0, 9.9 Hz), 5.34(1H, d, J=9.9 Hz), 5.88(1H, dd, J=3.1, 7.0 Hz), 7.16(1H, dd, J=1.8, 9.7 Hz), 7.37(1H, d, J=9.7 Hz), 7.44–7.50(2H, m), 7.52–7.58(2H, m), 7.60(1H, d, J=1.8 Hz), 7.75–7.82(3H, m), 8.32(1H, s)

EXAMPLE 46

2-(N-Benzenesulfonylvalyloxy-1-(imidazo-[1,2-a]pyridin-6-yl)-N'-methylcyclohexane-carbothioamide (M-form)

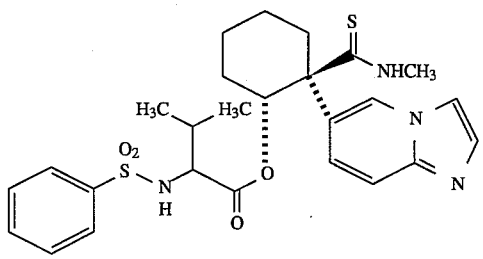

m.p. (°C.): 204–207

NMR (400 MHz, δ, CDCl₃):

0.67(3H, d, J=6.4 Hz), 0.68(3H, d, J=6.4 Hz), 1.33(1H, m), 1.48–1.64(3H, m), 1.77(1H, m), 1.96(1H, m), 2.24–2.37(2H, m), 2.62(1H, m), 3.04(3H, d, J=4.6Hz), 3.58(1H, m), 5.27(1H, d, J=9.0 Hz), 5.89(1H, dd, J=3.3, 9.0 Hz), 7.12(1H, m), 7.38–7.49(3H, m), 7.53–7.60(2H, m), 7.72–7.84(4H, m), 8.67(1H, s)

EXAMPLE 47

2-(N-Benzenesulfonylaspartyloxy)-1-(imidazo-[1,2-a]pyridin-6-yl)-N'-methylcyclohexane-carbothioamide

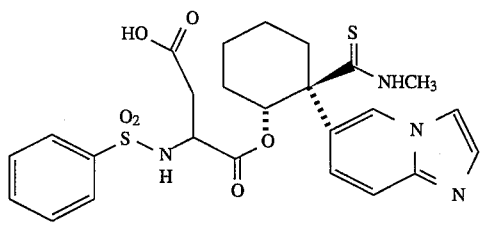

0.55 g of the 2-(N-benzenesulfonyl-β-benzylasparty-loxy)-1-(imidazo[1,2-a]pyridin-6-yl)-N'-methylcyclohex-anecarbothioamide prepared in the Example 30 was dissolved in 5 ml of dioxane, followed by the addition of 5 ml of a 1N aqueous solution of sodium hydroxide. The obtained mixture was stirred at room temperature for 30 minutes, followed by the addition of water and benzene. The aqueous phase was recovered, adjusted to a pH of about 5 with dilute hydrochloric acid, and extracter with chloroform/ethanol. The organic phase was dried over anhydrous magnesium sulfate and distilled to remove the solvent. The residue was dissolved in ethanol, followed by the addition of activated carbon. The resulting mixture was filtered and the filtrate was condensed. The condensate was crystallized from ether to give 0.31 g of the title compound as a pale-yellow powder (yield: 66%).

m.p. (°C.): 153–157

NMR (400 MHz, δ, DMSO-d₆):

1.26(1H, m), 1.34–1.44(2H, m), 1.51–1.62(2H, m), 2.06–2.28(4H, m), 2.74(1H, m), 2.90(3H, d, J=4.4 Hz), 3.79(1H, m), 5.95(1H, m), 7.31(1H, d, J=9.5 Hz), 7.44–7.63(6H, m), 7.66(1H, s), 8.03(1H, s), 8.16(1H, d,

J=8.6 Hz), 8.52(1H, s), 9.53(1H, br)

EXAMPLE 48

(−)-(1S, 2R)-2-(N-Benzenesulfonylglycyloxy)-1-(imidazo-[1,2-a]pyridin-6-yl)-N'-methylcyclohexane-carbothioamide

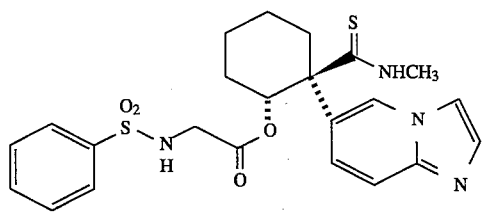

0.5 g of the (1S, 2R)-2-glycyloxy-1-(imidazo-[1,2-a]pyridin-6-yl)-N-methylcyclohexanecarbothioamide dihydrochloride prepared in the Preparative Example 34 was dissolved in 3 ml of pyridine, followed by the addition of 0.33 ml of benzenesulfonyl chloride. The obtained mixture was stirred at room temperature for 50 minutes, followed by the addition of a saturated aqueous solution of sodium carbonate. The obtained mixture was extracted with chloroform. The chloroform phase was dried over anhydrous magnesium sulfate and distilled to remove the solvent. The residue was purified by silica gel column chromatography (solvent: a 30:1 dichloromethane/methanol mixture) and crystallized from dichloromethane/ether to give 0.38 g of the title compound as a white powder (yield: 65%).

m.p. (°C.): 202–205 specific rotation $[\alpha]_D^{28}$: −68.2° (c=1.01, DMF)

NMR (400 MHz, δ, CDCl₃):

1.38(1H, m), 1.51–1.81(4H, m), 2.18(1H, m), 2.37(1H, m), 2.57(1H, m), 3.06(3H, d, J=4.8 Hz), 3.61(1H, d, J=17.8 Hz), 3.72(1H, d, J=17.8 Hz), 5.42(1H, br), 5.94(1H, dd, J=3.5, 9.3 Hz), 7.18(1H, dd, J=1.8, 9.5 Hz), 7.45–7.54(3H, m), 7.54–7.63(3H, m), 7.70(1H, s), 7.77–7.81(2H, m), 8.59(1H, m)

EXAMPLES 49 TO 53

The following compounds were each prepared in a similar manner to that of the Example 48.

EXAMPLE 48

(+)-(1S, 2R) 2-(N-(8-Quinolinesulfonyl)glycyloxy)-1-(imidazo-[1,2-a]pyridin-6-yl)-N'-methylcyclohexane-carbothioamide

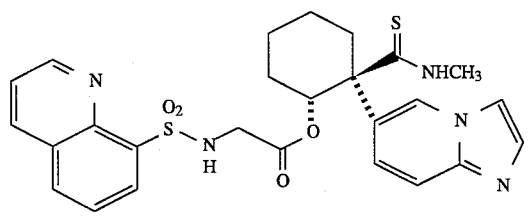

m.p. (°C.): 155–159 specific rotation $[\alpha]_D^{28}$: +52.2° (c=1.01, CHCl₃)

EXAMPLE 50

(1S, 2R)-2-(E-(6-Isoguinolinesulfonyl)glycyloxy)-1-(imidazo[1,2-a]pyridin-6-yl)-N'-methylcyclo-hexanecarbothioamide

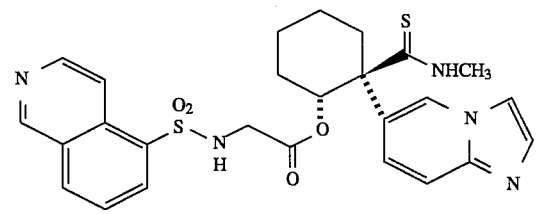

m.p. (°C.): 209–210 (dec.)

NMR (400 MHz, δ, CDCl₃):

1.33–1.61 (4H, m), 1.65–1.76(1H,m), 2.12–2.65(5H, m), 3.02(3H, d, J=4.6 Hz), 3.58(1H, d, J=17.9 Hz), 3.72(1H, d, J=17.9 Hz), 5.96(1H, dd, J=2.9, 7.9 Hz), 7.12–7.22(2H, m), 7.39(1H, d, J=1.1 Hz), 7.60–7.69(2H, m), 8.17(1H, d, J=8.2 Hz), 8.28(1H, br s), 8.30–8.36(2H, m), 8.42(1H, d, J=6.2 Hz), 8.57(1H, br s), 9.27(1H, s)

EXAMPLE 51

(−)-(1S, 2R)-(N-(2-Methylpyrazol-3-ylsulfonyl)-glycyloxy)-1-(imidazo-[1,2-a]pyridin-6-yl)-N'-methylcyclohexane-carbothioamide

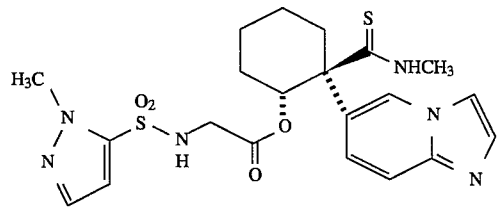

m.p. (°C.): 199–202 specific rotation $[\alpha]_D^{28}$: −81.8° (c=1.00 DMF)

NMR (400 MHz, δ, CDCl₃):

1.43(1H, m), 1.50–1.79(4H, m), 2.21(1H, m), 2.36(1H, m), 2.54(1H, m), 3.06(3H, d, J=4.6 Hz), 3.64(1H, d, J=17.9 Hz), 3.77(1H, d, J=17.9 Hz), 4.07(3H, s), 6.01(1H, dd, J=3.5, 8.9 Hz), 6.66(1H, d, J=2.2 Hz), 7.25(1H, dd, J=1.8, 9.5 Hz), 7.27(1H, d, J=2.2 Hz), 7.44–7.54(2H, m), 7.58(1H, d, J=1.1 Hz), 7.67(1H, m), 8.52(1H, m)

EXAMPLE 52

(+)-(1S, 2R) 2-(N-(P-Toluenesulfonyl)glycyloxy)-1-(imidazo-[1,2-a]pyridin-6-yl)-N'-methylcyclohexane-carbothioamide

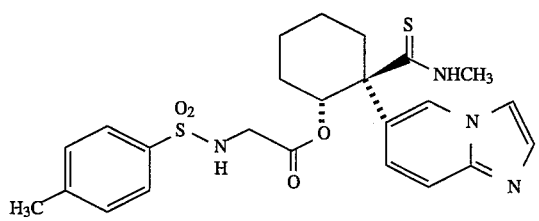

m.p. (°C.): 189–202 specific rotation $[\alpha]_D^{28}$: +16.6° (c=0.51 CHCl$_3$)

NMR (400 MHz, δ, CDCl$_3$):

1.36(1H, m), 1.50–1.69(3H, m), 1.74(1H, m), 2.16(1H, m), 2.37(1H, m), 2.43(3H, s), 2.58(1H, m), 3.06(3H, d, J=4.8 Hz), 3.60(1H, dd, J=5.1, 17.6 Hz), 3.70(1H, dd, J=5.7, 17.6 Hz), 5.18(1H, br), 5.93(1H, dd, J=3.7, 9.7 Hz), 7.19(1H, dd, J=1.8, 9.5 Hz), 7.28–7.32(2H, m), 7.45(1H, br), 7.54(1H, d, J=9.5 Hz), 7.64(1H, s), 7.65–7.69(2H, m), 7.73(1H, s), 8.63(1H, s)

EXAMPLE 53

(−)-(1S, 2R)-2-(N-(2-Thiophenesulfonyl)glycyloxy)-1-(imidazo-[1,2-a]pyridin-6-yl)-N'-methylcyclohexane-carbothioamide

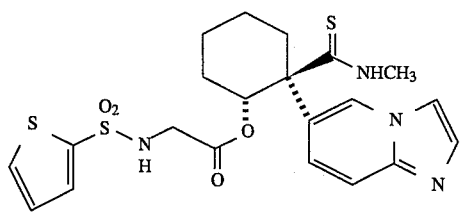

m.p. (°C.): 134–138 specific rotation $[\alpha]_D^{28}$: −6.6° (c=1.00 CHCl$_3$)

NMR (400 MHz, δ, CDCl$_3$):

1.40(1H, m), 1.52–1.68(3H, m), 1.76(1H, m), 2.21(1H, m), 2.38(1H, m), 2.56(1H, m), 3.07(3H, d, J=4.6 Hz), 3.67(1H, d, J=17.8 Hz), 3.80(1H, d, J=17.8 Hz), 5.37(1H, br), 5.98(1H, dd, J=3.5, 9.4 Hz), 7.08(1H, m), 7.21(1H, dd, J=1.8, 9.5 Hz), 7.40(1H, br), 7.50–7.56(2H, m), 7.59(1H, m), 7.64(1H, m), 7.70(1H, br s), 8.56(1H, m)

EXAMPLE 54

(−)-(1S, 2R)-2-(N-(1-Naphthalenesulfonyl)glycyloxy)-1-(imidazo-[1,2-a]pyridin-6-yl)-N'-methylcyclohexane-carbothioamide

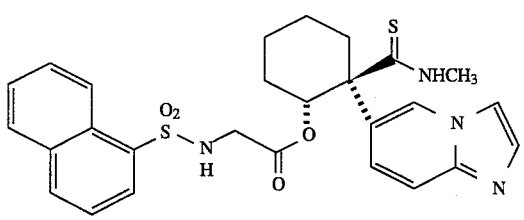

6.9 g of the (+)-(1S, 2R)-2-(N-t-butoxycarbonyl-glycyloxy)- 1-(imidazo[1.2-a]pyridin-6-yl)-N'-methylcyclohexanecarbothioamide prepared in the Preparative Example 25 was dissolved in 130 ml of chloroform, followed by the addition of 30 ml of 4N hydrochloric acid/ethyl acetate. The obtained mixture was stirred at room temperature overnight and concentrated in a vacuum to dryness, giving a white powder.

This powder was dissolved in 100 ml of pyridine. The obtained solution was stirred under cooling with ice, followed by the addition of 6.4 g of 1-naphthalenesulfonyl chloride in several portions. The obtained mixture was stirred and poured into a saturated aqueous solution of sodium hydrogencarbonate, followed by the extraction with chloroform. The chloroform phase was dried over anhydrous magnesium sulfate and distilled to remove the solvent. The residue was crystallized from dichloromethane to give a pale-yellow crystal. Further, the filtrate was purified by silica gel column chromatography (solvent: a 30:1 dichloromethane/methanol mixture) and combined with the above pale-yellow crystal. Thus, the title compound was obtained in a sum total of 6.1 g (yield: 74%).

m.p. (°C.): 158–160 specific rotation $[\alpha]_D^{28}$: −66.7° (c=1.0, DMF)

NMR (400 MHz, δ, DMSO-d$_6$):

1.20–1.27(1H, m), 1.34–1.40(2H, m), 1.46–1.56(2H, m), 2.00–2.08(2H, m), 2.61–2.68(1H, m), 2.89(1H, d, J=4.0 Hz), 3.29(1H, d, J=18.0 Hz), 3.58(1H, d, J=18.0 Hz), 5.90(1H, br s), 7.16(1H, dd, J=9.5, 2.0Hz), 7.41(1H, d, J=9.5 Hz), 7.53–7.57(2H, m), 7.63–7.70(2H, m), 7.85–7.89(1H, m), 7.96(1H, s), 8.06–8.09(1H, m), 8.19(1H, d, J=8.0 Hz), 8.44–8.49(2H, m), 8.53–8.56(1H, m), 9.44(1H, br s)

EXAMPLE 55

2-(N-Benzoylglycyloxy)-1-(imidazo[1,2-a]pyridin-6-yl)-N'-methylcyclohexanecarbothioamide

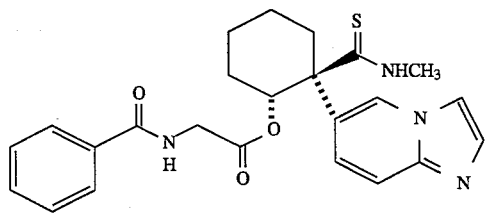

0.2 g of the 2-glycyloxy-1-(imidazo[1,2-a]-pyridin- 6-yl)-N-methylcyclohexanecarbothioamide prepared in the Preparative Example 28 was suspended in 2 ml of dichloromethane, followed by the addition of 0.05 ml of pyridine and 0.15 g of benzoic anhydride. The obtained mixture was stirred at room temperature for 18 hours, followed by the addition of a saturated aqueous solution of sodium hydrogencarbonate. The resulting mixture was extracted with chloroform. The chloroform phase was dried over anhydrous magnesium sulfate and distilled to remove the solvent. The residue was purified by silica gel column chromatography (solvent: 30:1 dichloromethane/methanol mixture), followed by the addition of ether. The resulting mixture was filtered to recover an insoluble matter. Thus, 0.15 g of the title compound was obtained as a white powder (yield: 57%).

m.p. (°C.): 226–229

NMR (400 MHz, δ, CDCl$_3$):

1.33 (1H, m), 1.51–1.87(4H, m), 2.22(1H, m), 2.35(1H, m), 2.61 (1H, m), 3.04(3H, d, J=4.6 Hz), 4.00(1H, dd, J=4.9, 17.9 Hz), 4.25(1H, dd, J=5.7, 17.9 Hz), 6.00(1H, dd, J=3.7, 9.7 Hz), 6.71(1H, br t, J=6 Hz), 7.18–7.27(2H, m), 7.38–7.58(6H, m), 7.69–7.74(2H, m), 8.45(1H, m)

EXAMPLE 56

2-(N-((2-Methanesulfonylamino)benzoyl)glycyloxy)-1-(imidazo-[1,2-a]pyridin-6-yl)-N'-methylcyclohexanecarbothioamide

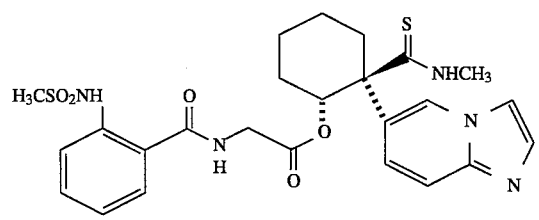

0.2g of the 2-glycyloxy-1-(imidazo[1,2-a]-pyridin- 6-yl)-N-methylcyclohexanecarbothioamide, 0.15 g of 2-methanesulfomylaminobenzoic acid, 0.14 g of N,N'-dicyclohexylcarbodiimide and 0.09 g of N-hydroxybenzotriazole were added to 2 ml of acetonitrile. The obtained mixture was stirred at room temperature for 14 hours, followed by the addition of acetonitrile. The formed insolubles were filtered out and the filtrate was concentrated. A saturated aqueous solution of sodium hydrogencarbonate was added to the residue, followed by the extraction with chloroform. The chloroform phase was dried over anhydrous magnesium sulfate and distilled to remove the solvent. The residue was purified by silica gel column chromatography (solvent:a 20:1 dichloromethane/methanol mixture) and crystallized from dichloromethane/ether to give 0.23 g of the title compound as a white powder (yield: 73%).

m.p. (°C.): 156–160

NMR (400 MHz, δ, CDCl$_3$):

1.42–1.88(5H, m), 2.25–2.40(2H, m), 2.58(1H, m), 3.00(3H, s), 3.09(3H, d, J=4.8 Hz), 3.88(1H, dd, J=4.8, 18.1 Hz), 4.17(1H, dd, J=5.5, 18.1 Hz), 6.14(1H, dd, J=3.3, 8.4 Hz), 6.95(1H, br t, J=4 Hz), 7.13(1H, m), 7.25(1H, br), 7.30(1H, dd, J=1.8, 9.5 Hz), 7.44–7.61(6H, m), 7.69(1H, m), 8.43(1H, m)

EXAMPLES 57 TO 59

The following compounds were each prepared in a similar manner to that of the Example 56.

EXAMPLE 57

2-(N-(2-Cyanobenzoyl)glycyloxy)-1-(imidazo[1,2-a]-pyridin-6-yl)-N'-methylcyclohexanecarbothioamide

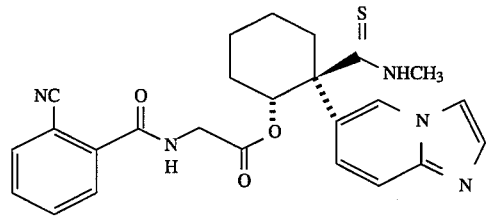

m.p. (°C.): 209–211

NMR (400 MHz, δ, CDCl$_3$):

1.45–1.88(5H, m), 2.17–2.26(2H, m), 2.64(1H, m), 3.05(3H, d, J=4.8 Hz), 4.30(1H, d, J=17.2 Hz), 4.36(1H, d, J=17.2 Hz), 5.95(1H, dd, J=3.5, 9.2 Hz), 7.09(1H, dd, J=1.6, 9.5 Hz), 7.21–7.39(4H, m), 7.59(1H, d, J=1.1 Hz), 7.72–7.82(3H, m), 8.26(1H, m)

EXAMPLE 58

2-(N-Methoxybenzoyl)glycyloxy)-1-(imidazo-[1,2-a]pyridin-6-yl)-N'-methylcyclohexanecarbothioamide

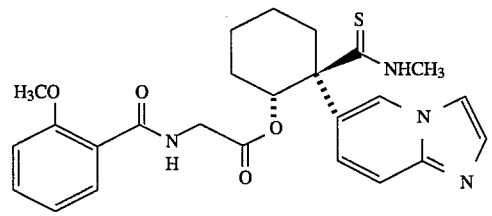

m.p. (°C.): 222–224

NMR (400 MHz, δ, CDCl$_3$):

1.50–1.90(5H, m), 2.21(1H, m), 2.36(1H, m), 2.65(1H, m), 3.06(3H, d, J=4.6 Hz), 3.99(3H, s), 4.00(1H, dd, J=4.9, 17.9 Hz), 4.29(1H, dd, J=5.9, 17.9 Hz), 5.89(1H, dd, J=3.8, 9.9 Hz), 6.96–7.03(2H, m), 7.17(1H, dd, J=1.8, 9.5 Hz), 7.33(1H, s), 7.40–7.53(3H, m), 7.69(1H, br), 7.99(1H, dd, J=1.6, 7.9 Hz), 8.42(1H, br t, J=7 Hz), 8.44(1H, m)

EXAMPLE 59

2-(N-Naphthalenecarbonyl)glycyloxy)-1-(imidazo-[1,2-a]pyridin-6-yl)-N'-methylcyclohexane-carbothioamide

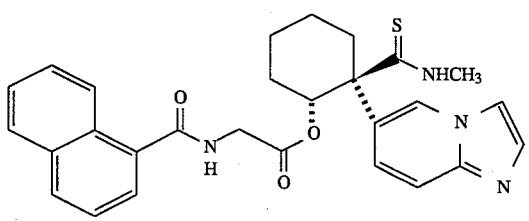

m.p. (°C.): 164–168
NMR (400 MHz, δ, CDCl₃):

1.40(1H, m), 1.51–1.73(3H, m), 1.85(1H, m), 2.28–2.39(2H, m), 2.58(1H, m), 3.00(3H, d, J=4.6 Hz), 4.04(1H, dd, J=4.9, 17.9 Hz), 4.32(1H, dd, J=5.7, 17.91 Hz), 6.07(1H, dd, J=3.5, 9.0 Hz), 6.64(1H, t, J=5.5 Hz), 7.19(1H, dd, J=1.8, 9.5 Hz), 7.38(1H, d, J=9.5 Hz), 7.41–7.54(5H, m), 7.61(1H, dd, J=1.1, 7.0 Hz), 7.76(1H, br), 7.87(1H, d, J=8.1 Hz), 7.94(1H, d, J=8.4 Hz), 8.28(1H, dd, J=0.7, 8.6 Hz), 8.47(1H, m)

EXAMPLE 60

2-(N-Phenylacetylglycyloxy)-1-(imidazo-[1,2-a]pyridin-6-yl)-N'-methylcyclohexane-carbothioamide

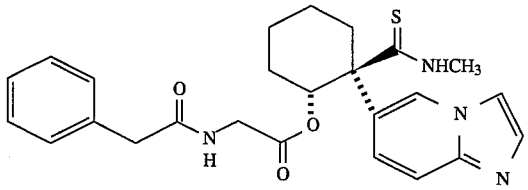

0.2 g of the 2-glycyloxy-1-(imidazo[1,2-a]-pyridin- 6-yl)-N-methylcyclohexanecarbothioamide prepared in the Preparative Example 28 was suspended in 2 ml of dichloromethine, followed by the addition of 0.05 ml of pyridine. The obtained mixture was cooled with ice, followed by the dropwise addition of 0.09 ml of phenylacetyl chloride. The obtained mixture was stirred under cooling for 30 minutes and then at room temperature for 40 minutes, followed by the addition of a saturated aqueous solution of sodium hydrogencarbonate. The resulting mixture was extracted with chloroform. The chloroform phase was dried over anhydrous magnesium sulfate and distilled to remove the solvent. The residue was purified by silica gel column chromatography (solvent: dichloromethane/methanol (30:1 to 20:1)) and crystallized from dichloromethine/ether to give 0.17 g of the title compound as a white powder (yield: 63%).

m.p. (°C.): 131–136
NMR (400 MHz, δ, CDCl₃):

1.40(1H, m), 1.48–1.64(2H, m), 1.71–1.82(2H, m), 2.21–2.33(2H, m), 2.56(1H, m), 3.07(3H, d, J=4.6 Hz), 3.53(1H, d, J=13.7 Hz), 3.58(1H, d, J=13.7 Hz), 3.66(1H, dd, J=4.6.18.1 Hz), 4.01(1H, dd, J=5.9, 18.1 Hz). 5.91(1H, br t, J=6 Hz), 6.00(1H, dd, J=3.5, 8.5 Hz), 7.20(1H, dd, J=2.0, 9.7 Hz), 7.21–7.37(5H, m), 7.45(1H, d, J=9.7 Hz), 7.58–7.65(3H, m). 8.41(1H, m)

EXAMPLE 61

(+)-(1S, 2R)-2-(N-Benzoylglycyloxy)-1-(imidazo-[1,2-a]pyridin-6-yl)-N'-methylcyclohexane-carbothioamide

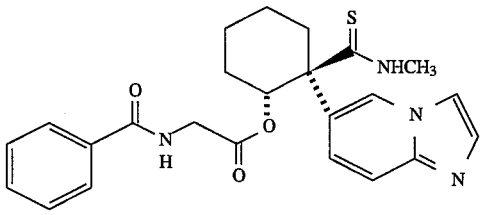

0.5 g of the (1S, 2R)-2-glycyloxy-1-(imidazo[ 1,2-a] pyridin-6-yl)-N-methylcyclohexanecarbothioamide dihydrochloride prepared in the Preparative Example 34, 0.16 g of benzoic acid, 0.27 g of N,N'-dicyclohexylcarbodiimide, 0.18 g of N-hydroxybenzotriazole and 0.35 ml of triethylamine were added to 10 ml of acetonitrile. The obtained mixture was stirred at room temperature for 60 hours, freed from the solvent by distillation, and concentrated. A saturated aqueous solution of sodium hydrogencarbonate was added to the concentrate, followed by the extraction with chloroform. The chloroform phase was dried over anhydrous magnesium sulfate and distilled to remove the solvent. The residue was purified by silica gel column chromatography (solvent: a 40:1 dichloromethane/methanol mixture) and crystallized from dichloromethane/ether to give 0.28 g of the title compound as a white powder (yield: 52%).

m.p. (°C.): 141–145
specific rotation $[\alpha]_D^{28}$: +65.3° CHCl₃)
NMR (400 MHz, δ, CDCl₃):

1.33(1H, m), 1.51–1.87(4H, m), 2.22(1H, m), 2.35(1H, m), 2.61(1H, m), 3.04(3H, d, J=4.6 Hz), 4.00(1H, dd, J=4.9, 17.9 Hz), 4.25(1H, dd, J=5.7, 17.9 Hz), 6.00(1H, dd, J=3.7, 9.7 Hz), 6.71(1H, br t, J=6 Hz), 7.18–7.27(2H, m), 7.38–7.58(6H, m), 7.69–7.74(2H, m), 8.45(1H, m)

EXAMPLE 62

(+)-(1S, 2R)-2-(N-(2-Methoxybenzoyl)glycyloxy)-1-(imidazo-[1,2-a]pyridin-6-yl)-N'-methylcyclohexane-carbothioamide

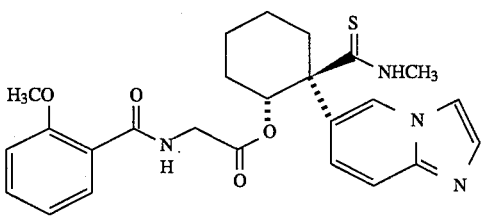

The title compound was prepared in the same manner as that of the Example 61 except that 2-methoxybenzoic acid was used instead of the benzoic acid.

m.p. (°C.): 126–129 specific rotation $[\alpha]_D^{28}$: +117.9° (c=0.99, CHCl$_3$)

NMR (400 MHz, δ, CDCl$_3$):

1.50–1.90(5H, m), 2.21(1H, m), 2.36(1H, m), 2.65(1H, m), 3.06(3H, d, J=4.5 Hz), 3.99(3H, s), 4.00 (1H, dd, J=4.9, 17.9 Hz), 4.29(1H, dd, J=5.9, 17.9 Hz), 5.89(1H, dd, J=3.8, 9.9 Hz), 6.96– 7.03(2H, m), 7.17(1H, dd, J=1.8, 9.5 Hz), 7.33(1H, s), 7.40–7.53(3H, m), 7.69(1H, br), 7.99(1H, dd, J=1.6, 7.9 Hz), 8.42(1H, br t, J=7 Hz), 8.44(1H, m)

EXAMPLE 63

2-(N-Benzenesulfonylsarcosyloxy)-1-(imidazo-[1,2-a] pyridin-6-yl)-N'-methylcyclohexane-carbothioamide

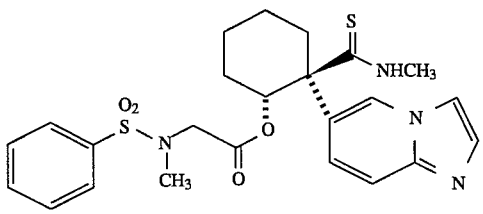

0.25 g of 2-hydroxy-1-(imidazo[1,2-a]pyridin-6-yl)-N-methylcyclohexanecarbothioamide, 0.4 g of N-benzenesulfonylsarcosine, 0.36 g of N,N'-dicyclohexylcarbodiimide and 0.1 g of 4-dimethylaminopyridine were added to 4 ml of N,N-dimethylformamide. The obtained mixture was stirred at room temperature for 13 hours, followed by tile addition of ethyl acetate and a saturated aqueous solution of sodium hydrogencarbonate. The formed insolubles were filtered out. The ethyl acetate phage was recovered, washed with water and a saturated aqueous solution of common salt, dried over anhydrous magnesium sulfate, and distilled to remove the solvent.. The residue was purified by silica gel column chromatography (solvent: a 40:1 dichloromethane/methanol mixture) and crystallized from dichloromethane/ether to give 0.42 g of the title compound as a white powder (yield: 97%).

m.p. (°C.): 208–209

NMR (400 MHz, δ, CDCl$_3$):

1.29(1H, m), 1.55–1.89(4H, m), 2.22(1H, m), 2.45(1H, m), 2.62–2.71(4H, m), 3.08(3H, d, J=4.8 Hz), 3.67(1H, d, J=17.0 Hz), 4.04(1H, d, J=17.0 Hz), 5.97(1H, dd, J=3.7, 10.4 Hz), 7.18–7.27(2H, m), 7.45–7.56(3H, m), 7.57–7.65(3H, m), 7.71–7.76(2H, m), 7.85(1H, m), 8.90(1H, m)

EXAMPLE 64

2-((2,3-Dihydro-1,1-dioxobenz[d]isothiazol-2-yl)-acetoxy)-1-(imidazo-[ 1-(imidazo[1,2-a]pyridin-6-yl)-N-methylcyclohexanecarbothioamide

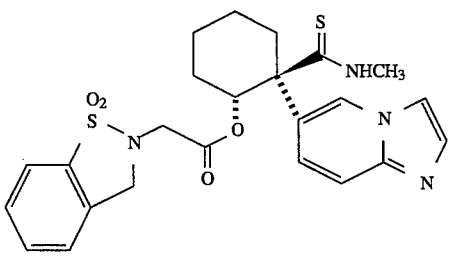

The title compound was prepared in the same manner as that of the Example 63 except that (2,3-dihydro-1,1-oxobenz[d]isothiazol-2-yl)acetic acid was used instead of the N-beizenesulfonylsarcosine.

m.p. (°C.): 223–224

NMR (400 MHz, δ, CDCl$_3$):

1.31(1H, m), 1.51–1.84(4H, m), 2.24(1H, m), 2.38(1H, m), 2.57(1H, m), 2.93(3H, d, J=4.8 Hz), 3.92(1H, d, J=17.4 Hz), 4.11(1H, d, J=17.4 Hz), 4.27(1H, d, J=13.9 Hz), 4.38(1H, d, J=13.9 Hz), 6.04(1H, dd, J=3.7, 9.9 Hz), 7.20(1H, dd, J=1.8, 9.7 Hz), 7.31–7.39(2H, m), 7.45–7.58(4H, m), 7.63(1H, dt, J=1.1, 7.5 Hz), 7.78(1H, d, J=7.5 Hz), 8.63(1H, m)

EXAMPLE 65

2-(Benzoyloxyacetoxy)-1-(imidazo[1,2-a]pyridin-6-yl)-N-methylcyclohexanecarbothioamide

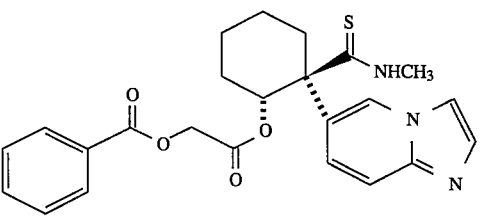

The title compound was prepared in the same manner as that of the Example 63 except that benzoyloxyacetic acid was used instead of the N-benzenesulfonylsarcosine.

m.p. (°C.): 225–226

NMR (400 MHz, δ, CDCl$_3$):

1.23(1H, m), 1.48–1.72(3H, m), 1.85(1H, m), 2.17–2.33(2H, m), 2.64(1H, m), 3.05(3H, d, J=4.8 Hz), 4.74(1H, d, J=15.7 Hz), 4.86(1H, d, J=15.7 Hz), 5.97(1H, dd, J=3.7, 9.9 Hz), 7.11–7.18(3H, m), 7.41–7.48(3H, m), 7.56(1H, d, J=1.1 Hz), 7.62(1H, m), 7.95–7.99 (m), 8.31(1H, m)

EXAMPLE 66

6-((1-Naphthalenecarboxy)acetoxy)-1-(imidazo[1,2-a]-pyridin-6-yl)-N-methylcyclohexanecarbothioamide

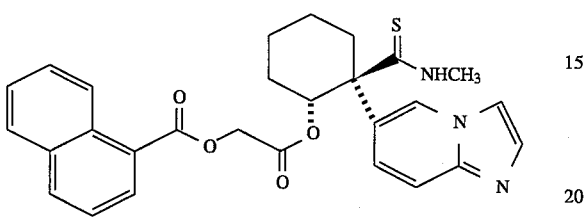

The title compound was prepared in the same manner as that of the Example 63 except that (1-naphthalenecarboxy)acetic acid was used instead of the N-benzenesulfonylsarcosine.

m.p. (°C.): 216–218

NMR (400 MHz, δ, CDCl₃):

1.27(1H, m), 1.47–1.73(3H, m), 1.88(1H, m), 2.24–2.35(2H, m), 2.59(1H, m), 3.02(3H, d, J=4.8 Hz), 4.79(1H, d, J=15.7 Hz), 4.90(1H, d, J=15.7 Hz), 6.05(1H, dd, J=3.5, 9.3 Hz), 6.97(1H, s), 7.10(1H, dd, J=1.8, 9.5 Hz), 7.30(1H, d, J=9.9 Hz), 7.39(1H, d, J=0.9 Hz), 7.42–7.57(4H, m), 7.91(1H, m), 8.08(1H, d, J=8.2 Hz), 8.23(1H, dd, J=1.3, 7.1 Hz), 8.27(1H, m), 8.77(1H, m)

EXAMPLE 67

2-(2-(1-Naphthalenesulfonamido)ethoxy)-1-(imidazo-[-1,2-a]pyridin-6-yl)-N-methylcyclohexane-carbothioamide

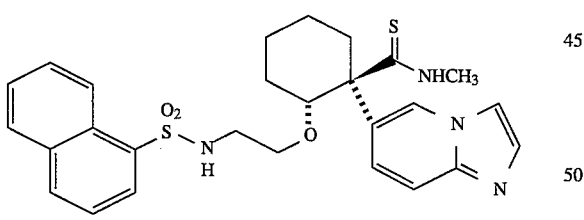

A mixture comprising 0.4 g of the 2-(2-(1-naphthalenesulfonamido)ethoxy)- 1-(imidazo[1,2-a]-pyridin- 6-yl)-1-((4-methoxybenzylthio)(methylimino)methyl)cyclohexane, 0.5 ml of anisole, 5 ml of trifluoroacetic acid and 5 ml of dichloromethane was stirred under cooling with ice for 1.5 hours, followed by the addition of ice-water. The resulting mixture was alkalinized with sodium carbonate and extracted with chloroform. The chloroform phase was dried over anhydrous magnesium sulfate and ditilled to remove the solvent. The residue was purified by silica gel column chromatography (solvent:a 30:1 dichloromethane/methanol mixture) and crystallized from ethyl acetate/n-hexane to give 0.21 g of the title compound as a white powder (yield: 65%).

m.p. (°C.): 128–132

NMR (400 MHz, δ, CDCl₃):

1.06(1H, m), 1.39(1H, m), 1.54(1H, m), 1.66(1H, m), 1.91(1H, m), 2.29(1H, m), 2.56(1H, m), 3.05(1H, m), 3.13(3H, d, J=4.8 Hz), 3.15(1H, m), 3.36(1H, m), 3.72(1H, m), 4.29(1H, dd, J=3.9, 11.5 Hz), 5.52(1H, t, J=5.7 Hz), 7.16(1H, dd, J=1.8, 9.5 Hz), 7.50–7.65(7H, m), 7.95(1H, dd, J=1.8, 7.7 Hz), 8.22(1H, dd, J=1.1, 7.3 Hz), 8.66(1H, d, J=8.6 Hz), 8.77(1H s)

EXAMPLE 68

2(2-Benzenesulfonamidoethoxy)-1-(imidazo[-1,2-a]-pyridin-6-yl)-N-methylcyclohexanecarbothioamide

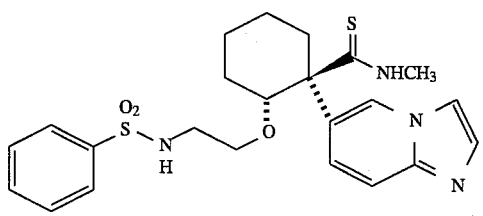

The title compound was prepared in the same manner as that of the Example 67 except that the compound prepared in the Preparative Example 27 was used as the starting compound.

m.p. (°C.): 109–112

(400 MHz, δ, CDCl₃):

1.08(1H, m), 1.37–1.79(4H, m), 1.99(1H, m), 1H, m), 2.57(1H, m), 3.05–3.25(2H, m), 3.14(3H, d, J=4.6 Hz), 3.40(1H, m), 3.78(1H, 4.32(1H, dd, J=3.8, 11.7 Hz), 5.29(1H, br), 7.18(1H, dd, J=1.8, 9.5 Hz), 7.47–7.66(7H, m), 7.83–7.89(2H, m), 8.80(1H, s)

EXAMPLE 69

2-(2-(1-Naphthalensulfonamido)ethoxyimino)-1-(imidazo[1,2-a]pyridin-6-yl)-N-methylcyclohexane-carbothioamide

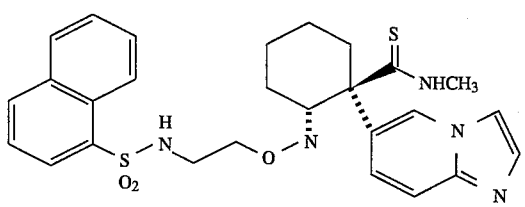

0.5 g of N-methyl-2-oxo-1-(imidazo[1,2-a]-pyridin- 6-yl-)cyclohexanecarbothioamide, 1.02 g of O-(2-(1-naphthalenesulfonamldo)ethyl)hydroxylamine and 0.96 g of pyridinium p-toluenesulfonate were added to 5 ml of pyridine. The obtained mixture was stirred at 80° C. for 16 hours, followed by the addition of a saturated aqueous solution of sodium hydrogencarbonate. The obtained mixture was extracted with chloroform. The chloroform phase was dried over anhydrous magnesium sulfate and distilled to remove the solvent. The residue was purified by silica gel column chromatography (solvent:a 30:1 ethyl acetate/methanol mixture) and crystallized from dichloromethane/ether to give 0.67 g of the title compound as a white solid (yield: 74%).

m.p. (°C.): 127–131

NMR (400 MHz, δ, CDCl₃):

1.48–1.80(3H, m), 1.86(1H, m), 2.12–2.36(2H, m), 2.88(1H, m), 3.03–3.14(2H, m), 3.24(1H, m), 3.26(3H, d, J=4.8 Hz), 3.96–4.08(2H, m), 5.29(1H, t, J=5.7 Hz), 6.94(1H, dd, J=1.8, 9.5 Hz), 7.38(1H, d, J=9.5 Hz), 7.52–7.68(5H, m), 7.94(1H, m), 7.97(1H, m), 8.09(1H, d, J=8.2 Hz), 8.16(1H, br d, J=5 Hz), 8.20(1H, dd, J=1.3, 7.3 Hz), 8.56(1H, m)

EXAMPLE 70

2-(2-(1-Naphthalenesulfonamido)ethylamino)-1-(imidazo[1,2-a]pyridin-6-yl)-N-methylcyclohexanecarbothioamide (L-form)

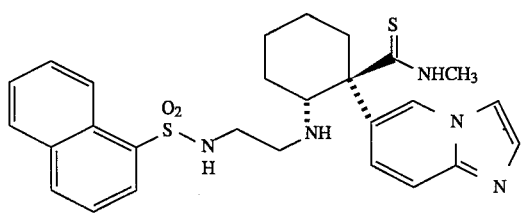

600 m of 1-(imidazo[1,2-a]pyridin-6-yl)-N-methyl-2-oxocyclohexanecarbothioamide and 2.09 g of 1-naphthalenesulfonylaminoethylamine were dissolved in ml of dichloromethane to form a solution. 2 ml of a 1M solution of titanium tetrachloride in dichloromethane was added to this solution in 30 minutes at room temperature. The obtained mixture was stirred overnight, followed by the addition of 1 ml of concentrated aqueous ammonia. The crystal thus precipitated was filtered out, followed by the washing with 10% methanol/dichloromethane. The filtrate was concentrated in a vacuum, followed by the addition of 10 ml of methanol. 200 mg of sodium cyanoborohydride was added to the mixture at room temperature. The obtained mixture was stirred for one hour and concentrate, in a vacuum, followed by the addition of a saturated aqueous solution of sodium hydrogencarbonate. The resulting mixture was extracted with chloroform. The chloroform phase was dried over anhydrous sodium sulfate and concentrated in a vacuum. The residue was purified by silica gel column chromatography (solvent: a 10:10:1 dichloromethane/ethyl acetate/methanol mixture) to give 280 mg of a lower-polarity diastereomer (L-form) and 350 mg of a higher-polarity diastereomer (M-form) each as a pale-yellow crystal.

m.p. (°C.): 185–186

NMR (400 MHz, δ, CDCl₃):

1.30–1.50(2H, m), 1.56–1.89(5H, m), 1.01–2.07(1H, m), 2.42–2.52(1H, m), 2.68–2.80(1H, m), 2.81–2.91(1H, m), 2.91–3.04(2H, m), 3.33(3H, d, J=4.8 Hz), 3.35–3.42(1H, m), 6.67–6.76(1H, m), 7.22(1H, dd, J=2, 9.6 Hz), 7.31(1H, d, J=1.2 Hz), 7.37–7.56(5H, m), 7.90(1H, d, J=8.4 Hz), 8.02(1H, d, J=7.2 Hz), 8.03(1H, s), 8.13(1H, dd, J=1.2, 7.2 Hz), 8.47(1H, d, J=8.8 Hz)

EXAMPLE 71

2-(2-(1-Naphthalenesulfonamido)ethylamino)-1-(imidazo[1,2-a]pyridin-6-yl-hexanecarbothioamide (M-form)

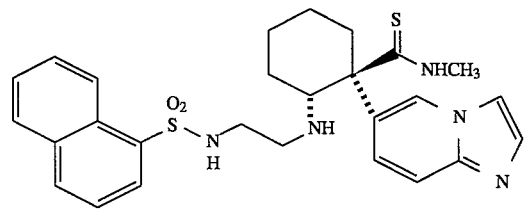

The title compound was prepared in a similar manner to that of the Example 70.

m.p. (°C.): 137–138

NMR (400 MHz, δ, CDCl₃):

1.10–1.22(1H, m), 1.33–1.70(5H, m), 1.79–1.86(1H, m), 2.28–2.35(1H, m), 2.44–2.62(2H, m), 2.78–2.86(1H, m), 2.95–3.01(2H, m), 3.16(3H, d, J=3.6 Hz), 3.49–3.54(1H, m), 5.44–5.52(1H, m), 7.17(1H, dd, J=2, 9.6Hz), 7.52–7.68(6H, m), 7.96(1H, dd, J=1.2, 8 Hz), 7.98–8.04(1H, m), 8.08(1H, d, J=8 Hz), 8.65(1H, d, J=8 Hz), 9.10(1H, s)

EXAMPLE 72

4.06 g of the compound obtained in Example 25 was dissolved with heat in 30 ml of a 75% aqueous ethanol solution. 0.52 ml of methane sulfonic acid was added to the solution. The mixture was stirred while cooled with ice for 30 minutes. Then precipitates were filtered and washed with water, dried in warm air at 100° C. overnight and 4.27 g of methane sulfonic acid salt of the starting compound was obtained in the form of white crystals. The melting point was 217–218 degree c.

1H-NMR (DMSO-d6, δppm)

1.22–1.34(1H, m), 1.38–1.46(2H, m), 1.56–1.64(2H, m), 2.10–2.22(2H, m), 2.33(3H, s), 2.74–2.80(1H, m), 2.91(3H, d, J=4.5Hz), 3.39(1H, dd, J=18.0, 6.0 Hz), 3.53(1H, dd, J=18.0, 6.5 Hz), 6.07(1H, s), 7.58(1H, dd, J=8.0, 7.5 Hz), 7.64–7.72(2H, m), 7.80(1H, d, J=7.5 Hz), 7.90(1H, d, J=9.5 Hz), 7.97(1H, dd, J=9.5, 1.5 Hz), 8.08(1H, dd, J=8.0, 1.5 Hz), 8.22–8.40(3H, m), 8.89(1H, s), 9.62(1H, brs), 14.3(1H, brs)

What is claimed is:

1. A cyclohexane derivative having formula (I) or a pharmacologically acceptable salt thereof:

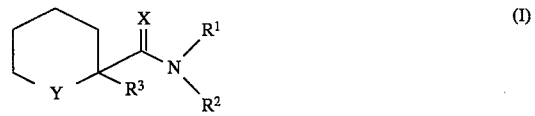

wherein $R^1$ and $R^2$ may be the same or different from each other and each represents hydrogen or lower alkyl; $R^3$ represents optionally substituted unidazopyridyl; X represents oxygen or sulfur; and Y represents a group represented by the following formula (1):

wherein p is 1; and J represents a group represented by the following formula (2):

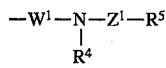  (2)

(wherein $R^4$ represents hydrogen or lower alkyl; $R^5$ represents optionally substituted aryl, optionally substituted arylalkyl, optionally substituted heteroaryl or optionally substituted heteroarylalkyl; $Z^1$ represents a group represented by formula —$SO_2$— or a group represented by formula —CO—; and $W^1$ represents a group represented by the following formula (3):

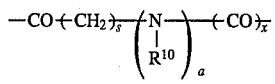  (3)

(wherein a and x are independent from each other and each an integer of 0 or 1; s is an integer of 0 to 6; and $R^{10}$ represents hydrogen or lower alkyl), a group represented by the following formula (4):

  (4)

(wherein $R^{11}$ represents hydrogen, lower alkyl, hydroxyalkyl, optionally substituted arylalkyl or optionally protected carboxyalkyl), or a group represented by the following formula (5):

  (5)

(wherein g is an integer of 0 to 6.

2. The cyclohexane derivative as claimed in claim 1, which has the formula (II) or a pharmacologically acceptable salt thereof:

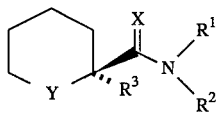  (II)

(wherein $R^1$, $R^2$, $R^3$, X and Y are each as defined above).

3. The cyclohexane derivative as claimed in claim 1, which has the formula (III), or a pharmacologically acceptable salt thereof:

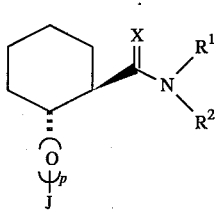  (III)

(wherein $R^1$, $R^2$, $R^3$, X, J and p are each as defined above).

4. The cyclohexane derivative as claimed in claim 1 having the formula (I) in which R1 is hydrogen atom, R2 is a C1–C6 alkyl, R3 is imidazopyridyl, X is sulfur, Y is =CH—O—J and J is —COCH2—NH—SO2-naphthyl or a pharmacologically acceptable salt thereof.

5. The cyclohexane derivative as claimed in claim 4, in which R2 is ethyl, or a pharmacologically acceptable salt thereof.

6. A pharmacological composition comprising a pharmacologically effective amount of the cyclohexane derivative or a pharmacologically acceptable salt thereof and a pharmacologically accetable carrier.

7. A method for preventing or treating a disease against which a potassium channel opening is efficacious by administering a pharmacologically effective amount of the cyclohexane derivative as defined in claim 1 or a pharmacologically acceptable salt thereof to human subject who will suffer or suffers the disease.

8. The method as claimed in claim 7, in which a bronchodilator action, a vasodilative action or an action of relaxing the smooth muscle of urinary bladder is efficacious against the disease.

9. The method as claimed in claim 7, in which the disease is asthma, hypertension, pollakisuria or urinary incontinence.

* * * * *

UNITED STATES PATENT AND TRADEMARK OFFICE
CERTIFICATE OF CORRECTION

PATENT NO. : 5,478,839
DATED : December 26, 1995
INVENTOR(S) : Kabasawa et al

Page 1 of 2

It is certified that error appears in the above-indentified patent and that said Letters Patent is hereby corrected as shown below:

Column 39, line 32, correct the spelling of "methylcyclohexane."
Column 39, line 33, correct the spelling of "carbothioamide".
Column 64, line 8, delete the hyphen "-" after "imidazo".
Column 71, line 41, delete the hyphen after "[" and before "1,2".
Column 72, line 13, insert a hyphen "-" after the "2" and beofre the "("
Column 74, line 59, correct the spelling of "imidazopyridyl"

UNITED STATES PATENT AND TRADEMARK OFFICE
CERTIFICATE OF CORRECTION

PATENT NO. : 5,478,839
DATED : December 26, 1995
INVENTOR(S) : Kabasawa et al

It is certified that error appears in the above-indentified patent and that said Letters Patent is hereby corrected as shown below:

Column 76, claim 3, delete the formula and insert the following formula:

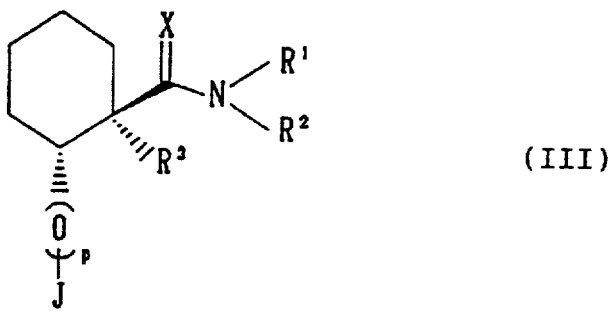

(III)

Signed and Sealed this

Seventh Day of January, 1997

Attest:

BRUCE LEHMAN

*Attesting Officer*     *Commissioner of Patents and Trademarks*